(12) United States Patent
Deng et al.

(10) Patent No.: US 12,410,142 B2
(45) Date of Patent: Sep. 9, 2025

(54) SUBSTITUTED IMIDAZOLE SALT COMPOUNDS, PREPARATION METHOD THEREOF, PHARMACEUTICAL COMPOSITION THEREOF AND APPLICATION THEREOF

(71) Applicant: Xiamen Vivohealths Technology Co., Ltd., Fujian (CN)

(72) Inventors: Xianming Deng, Fujian (CN); Shengcai Lin, Fujian (CN); Chensong Zhang, Fujian (CN)

(73) Assignee: Xiamen Vivohealths Technology Co., Ltd., Fujian (CN)

( * ) Notice: Subject to any disclaimer, the term of this patent is extended or adjusted under 35 U.S.C. 154(b) by 67 days.

(21) Appl. No.: 18/097,640

(22) Filed: Jan. 17, 2023

(65) Prior Publication Data
US 2023/0202986 A1 Jun. 29, 2023

Related U.S. Application Data

(62) Division of application No. 16/500,774, filed as application No. PCT/CN2018/081898 on Apr. 4, 2018, now Pat. No. 11,584,722.

(30) Foreign Application Priority Data

Apr. 7, 2017 (CN) .......................... 201710223125.4

(51) Int. Cl.
| | | |
|---|---|---|
| A61K 31/4164 | (2006.01) | |
| C07D 233/60 | (2006.01) | |
| C07D 233/61 | (2006.01) | |
| C07D 235/10 | (2006.01) | |
| C07D 235/12 | (2006.01) | |

(52) U.S. Cl.
CPC ......... *C07D 233/60* (2013.01); *C07D 233/61* (2013.01); *C07D 235/10* (2013.01); *C07D 235/12* (2013.01)

(58) Field of Classification Search
None
See application file for complete search history.

(56) References Cited

U.S. PATENT DOCUMENTS

| | | | |
|---|---|---|---|
| 4,150,967 A | 4/1979 | Luerssen et al. | |
| 8,592,585 B2 | 11/2013 | Chi et al. | |

FOREIGN PATENT DOCUMENTS

| | | | |
|---|---|---|---|
| BE | 696982 A | 10/1967 | |
| CN | 101698660 A | 4/2010 | |
| CN | 101983057 A | 3/2011 | |
| CN | 103547154 A | 1/2014 | |
| DE | 2706839 A1 | 8/1978 | |
| JP | 2009215200 A | 9/2009 | |
| WO | 2008006432 A1 | 1/2008 | |
| WO | 2009096905 A1 | 8/2009 | |
| WO | 2009123569 A1 | 10/2009 | |
| WO | 2009133923 A1 | 11/2009 | |
| WO | 2012149523 A1 | 11/2012 | |
| WO | 2014199352 A2 | 12/2014 | |
| WO | 2014199352 A3 | 12/2014 | |
| WO | 2018106922 A1 | 6/2018 | |

OTHER PUBLICATIONS

Boal et al., "Synthesis of Germanosilicate Molecular Sieves from Mono- and Di-Quaternary Ammonium OSDAs Constructed from Benzyl Imidazolium Derivatives: Stabilization of Large Micropore Volumes Including New Molecular Sieve CIT-13", Chemistry of Materials, 2016, pp. 2158-2164, vol. 28, No. 7.

Wu et al., "Phenolic hydroxyl-functionalized imidazolium ionic liquids: Highly efficient catalysts for the fixation of CO2 to cyclic carbonates", Jornal of Molecular Catalysis A: Chemical, 2016, pp. 1-8, vol. 418-419.

Yang et al., "Highly alkaline stable N1-alkyl substituted 2-methylimidazolium functionalized alkaline anion exchange membranes", Journal of Materials Chemistry A, 2015, pp. 8559-8565, vol. 3, No. 16.

Ganapathi et al., "Synthesis and Characterization of 1,2-Dimethyl Imidazolium Ionic Liquids and Their Catalytic Activities", 2015, pp. 2135-2141, vol. 45, No. 18.

Leal et al., "Palladium metal nanoparticles stabilized by ionophilic ligands in ionic liquids: synthesis and application in hydrogenation reactions", Catalysis Science & Technology, 2015, pp. 903-909, vol. 5, No. 2.

Xia et al., "The regioselectivity and synthetic mechanism of 1,2-benzimidazole squaraines: combined experimental and theoretical studies", RSC Advances, 2013, pp. 18055-18061, vol. 3, No. 39.

(Continued)

*Primary Examiner* — Samantha L Shterengarts
(74) *Attorney, Agent, or Firm* — MacMillan, Sobanski & Todd, LLC

(57) ABSTRACT

Disclosed in the invention are a type of compounds having aldolase selective inhibitory activity, a method for the preparation thereof, a pharmaceutical composition comprising the same, and use of these compounds in the manufacture of a medicament for inhibiting triglyceride and cholesterol synthesis, for reducing fatty acid synthesis, for preventing and/or treating obesity and type II diabetes, for preventing and/or treating tumor, for preventing and/or treating Parkinson's disease, for preventing and/or treating Alzheimer's disease or for prolonging the lifespan of mammals:

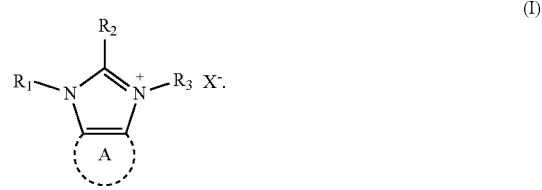

(I)

10 Claims, 9 Drawing Sheets

(56) References Cited

OTHER PUBLICATIONS

Kumar et al., "Convenient Syntheses of Bulky Group Containing Imidazolium Ionic Liquids", Journal of Heterocyclic Chemistry, 2011, pp. 370-374, vol. 49, No. 2.

Patil et al., "Synthesis, cytotoxicity and anitbacterial studies of symmetrically and non-symmetrically benzyl- or p-cyanobenzyl-substituted N-Heterocyclic carbene-silver complexes", 2010, pp. 781-793, vol. 24, No. 11.

International Search Report, Application No. PCT/CN2018/081898, dated Jul. 5, 2018.

European Supplementary Search Report, Application No. 18781729.1, dated Sep. 29, 2020.

The European Communication pursuant to Article 94(3) EPC, Application No. 18781729.1, dated Nov. 3, 2021.

Shackelford et al., "The LKB1-AMPK pathway: metabolism and growth control in tumour suppression", Nature Reviews/Cancer, 2009, vol. 9, pp. 563-575.

Grandjean et al., "Definition of a Novel Feed-Forward Mechanism for Glycolysis-HIF1a Signaling in Hypoxic Tumors Highlights Aldolase A as a Therapeutic Target", American Association for Cancer Research, 2016, vol. 76, No. 14, pp. 4259-4269.

Lew et al., "Targeting of Several Glycolytic Enzymes Using RNA Interference Reveals Aldolase Affects Cancer Cell Proliferation through a Non-glycolytic Mechanism", The Journal of Biological Chemistry, 2012, vol. 287, No. 51, pp. 42554-42563.

Bartelt et al., "Adipose tissue browning and metabolic health", Nature Reviews/Endocrinology, Advanced Online Publication, 2013, pp. 1-13.

Mishra et al., "Mitochondrial dynamics and inheritance during cell division, development and disease", Nature Reviews/Molecular Cell Biology, 2014, vol. 15, pp. 634-646.

Stenesen et al., "Adenosine Nucleotide Biosynthesis and AMPK Regulate Adult Life Span and Mediate the Longevity Benefit of Caloric Restriction in Flies", Cell Metabolism, 2013, vol. 17, pp. 101-112.

SUBSTITUTED IMIDAZOLE SALT COMPOUNDS, PREPARATION METHOD THEREOF, PHARMACEUTICAL COMPOSITION THEREOF AND APPLICATION THEREOF

TECHNICAL FIELD

The invention relates to the field of medicinal chemistry, and in particular to a type of compounds having aldolase selective inhibitory activity, a method for the preparation thereof, a pharmaceutical composition comprising the same, and use of these compounds in the manufacture of a medicament for reducing fatty acid synthesis, for inhibiting triglyceride and cholesterol synthesis, for preventing and/or treating obesity and type II diabetes, for preventing and/or treating tumor, for preventing and/or treating Parkinson's disease, for preventing and/or treating Alzheimer's disease or for prolonging the lifespan of mammals.

BACKGROUND ART

Adenosine 5'-monophosphate-activated protein kinase (AMPK) is an important molecule that regulates energy balance of cells and organisms (Nat. Rev. Mol. Cell Biol. 2012, 13, 251-262.). Because AMPK has versatile effects on carbohydrate, fat and cholesterol metabolism and biosynthesis, while these effects are closely related to many major diseases such as diabetes (Nat. Rev. Endocrinol. 2014, 10, 24-36.), Parkinson's disease and Alzheimer's disease (Nat. Rev. Mol. Cell Biol. 2014, 15, 634-646.), tumor (Nat. Cell Biol. 2011, 13, 1016-1023, and Annu Rev Genet. 2009, 43, 67-93.), and prolonging the lifespan of organisms (Curr. Biol. 2007, 17, 1646-1656, Cell Metab. 2013, 17, 101-112, and Nat. Commun. 2013, 4, 2192.), AMPK is one of the most attractive drug targets for treating major diseases. Although in academic circles using a number of methods many activators have been obtained with AMPK as a target and systematic studies have been carried out, the results show that AMPK as a direct target for drugs has many drawbacks, such as insufficient efficacy or low specificity. Therefore, there is an urgent need to develop a drug with a new mechanism of action to achieve the purpose of activating AMPK and treating related diseases.

Fructose-1,6-bisphosphate aldolase (abbreviated as FBP aldolase, also known as aldolase in the present invention, including aldolase A, aldolase B and aldolase C) —a novel regulator of AMPK, is an important metabolic enzyme in the process of sugar metabolism. In the glycolysis pathway, it catalyzes fructose 1,6-diphosphate (FBP) to produce glyceraldehyde 3-phosphate (G3P) and dihydroxyacetone phosphate (DHAP) (Eur. J. Biochem. 2000, 267, 1858-1868.), the latter undergoing multiple enzymatic reactions to produce pyruvic acid. At the same time, in the gluconeogenesis pathway, it can catalyze the reverse process of this reaction. In this process, aldolase plays a role that cannot be replaced by other metabolic enzymes. At this stage, the understanding of the function of aldolase is only limited to the nature of the metabolic enzyme itself. It has been reported that some mutants of aldolase may be related to lactose intolerance, but the specific mechanism is still unclear. It is worth mentioning that, in tumor tissues, the expression level of aldolase is significantly increased, which is likely to increase the level of Warburg effect and promote the development of tumor cells (J. Biol. Chem 2010, 285, 11983-11990, and Am. J. Physiol. Cell Physiol. 2011, 300, C1442-1455.). There is also evidence to demonstrate that knockdown of aldolase in tumor cells may directly lead to the cessation of tumor cell growth (J. Biol. Chem. 2012, 287, 42554-42563.).

As early as 1970, the researchers designed a number of fructose 1,6-diphosphate analogs that could not be converted by aldolase, which achieved inhibitory effect by competing with fructose 1,6-diphosphate in binding aldolase. However, these inhibitors do not have good cell permeability and cannot enter cells to play their role, resulting in their application being greatly limited. The only reported effective aldolase inhibitor at the physiological level is TDZD-8 (Cancer Res. 2016, 76, 4259-4269.), but this inhibitor has a clear non-aldolase target, kinase GSK3.

Aldolase can directly regulate the activation of AMPK, so it can be used as an important target for the regulation of AMPK. Aldolase inhibitors can significantly activate AMPK by inhibiting the activity of intracellular aldolase, and can be used for the prevention and treatment of related diseases caused by low AMPK level.

SUMMARY OF INVENTION

In order to find new aldolase inhibitors, after extensive and in-depth research, the inventors of the present invention have designed and synthesized a series of polysubstituted imidazole salt derivatives having novel structures, high safety and high activity, and have studied aldolase inhibitory activity and effect on AMPK signaling pathway of this novel type of derivatives.

The present invention provides a compound having the general formula:

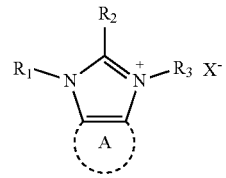

or a stereoisomer thereof, a prodrug thereof, a pharmaceutically acceptable salt thereof or a pharmaceutically acceptable solvate thereof.

More specifically, the present invention provides compounds having the general formulas (I, II):

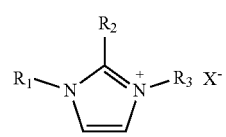

I

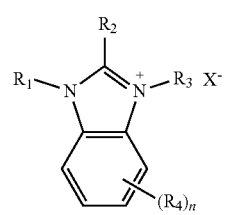

II

The definitions of substituents and symbols are described in detail below.

One object of the present invention is to provide a compound having aldolase inhibitory activity and a stereoisomer thereof, a prodrug thereof, a pharmaceutically acceptable salt thereof or a pharmaceutically acceptable solvate thereof.

Another object of the present invention is to provide a method for the preparation of the above compound.

Another object of the present invention is to provide a pharmaceutical composition comprising the above compound.

Another object of the present invention is to provide use of the above compound and the pharmaceutical composition comprising the compound in the manufacture of a medicament having aldolase inhibitory activity.

Another object of the present invention is to provide use of the above compound and the pharmaceutical composition comprising the compound in the manufacture of a medicament for inhibiting cholesterol synthesis, for lowering fatty acid synthesis, for preventing and/or treating obesity, for preventing and/or treating diabetes, for preventing and/or treating tumor, for preventing and/or treating Parkinson's disease, for preventing and/or treating Alzheimer's disease or for prolonging the lifespan of mammals.

DETAILED DESCRIPTION OF THE PREFERRED EMBODIMENT(S)

Figure 1:
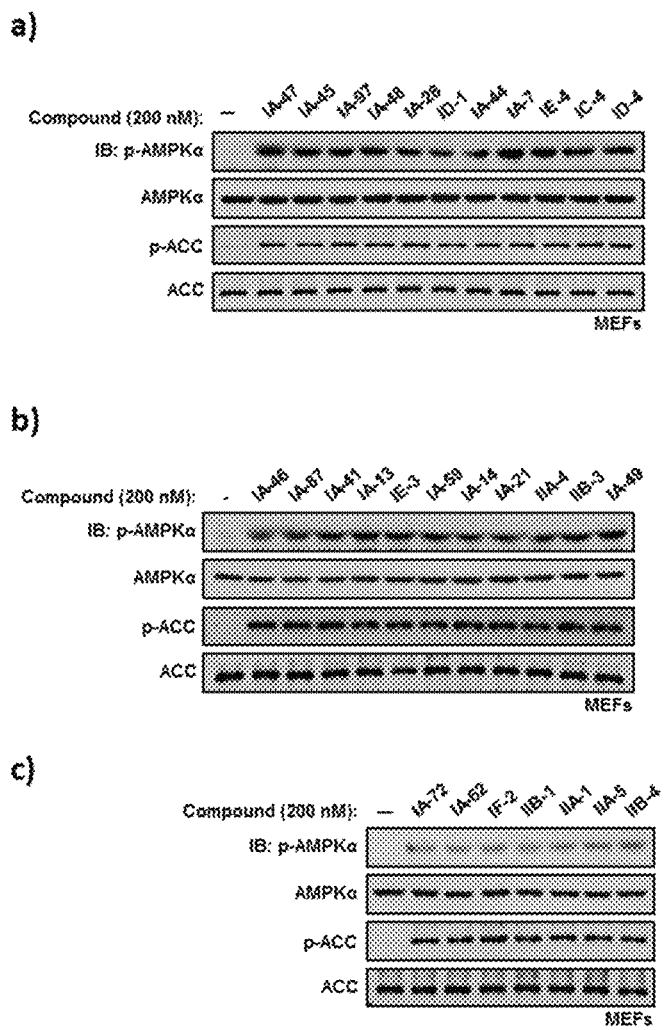
FIG. 1 shows that the compounds significantly inhibit aldolase activity in mouse embryonic fibroblasts (MEFs). The results in panels a), b) and c) showed that the tested compounds at 200 nM could inhibit aldolase activity in MEFs cells to different extents, thereby activating AMPK, and promoting phosphorylation of AMPK (p-AMPK) and phosphorylation of its downstream substrate ACC1/ACC2 (p-ACC) to different extents.

Specific Modes for Carrying Out the Invention

Various specific embodiments, modes and examples are described herein, including exemplary embodiments and definitions, to understand the claimed invention. While the following detailed description sets forth specific preferred embodiments, those skilled in the art will appreciate that these embodiments are illustrative only, and that the present invention can be practiced in other ways. For the purpose of determining infringement, the scope of the present invention will cover any one or more of the appended claims, including equivalents thereof, and elements or limitations equivalent to those recited.

The present invention is achieved by the following technical solutions.

In one aspect, the present invention provides a compound having the general formula:

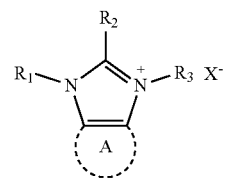

or a stereoisomer thereof, a prodrug thereof, a pharmaceutically acceptable salt thereof or a pharmaceutically acceptable solvate thereof, wherein, R1 is selected from C1-C24 alkyl, C1-C24 oxygen-containing alkyl, C1-C24 fluorine-containing alkyl, C1-C24 fluorine- and oxygen-containing alkyl;

R2 is selected from H, C1-C6 alkyl, C3-C6 cycloalkyl;

R3 is selected from:

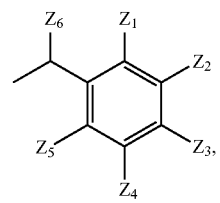

wherein Z1, Z2, Z3, Z4, Z5 each are independently selected from:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-di-isopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z2 and Z3 may form an oxygen-containing substituted or unsubstituted five- or six-membered ring; the substituent may be selected from the same substituents as Z1;

Z4 and Z5 may form a nitrogen-containing substituted or unsubstituted five- or six-membered ring; the substituent may be selected from the same substituents as Z1;

Z6 is selected from H, C1-C3 alkyl, C3-C6 cycloalkyl;

2)

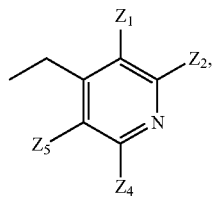

wherein Z2, Z3, Z4, Z5 are defined the same as in 1);

3)

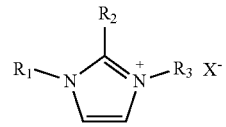

wherein Z2, Z3, Z4, Z5 are defined the same as in 1);

4)

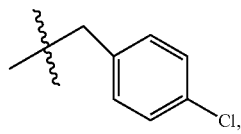

wherein Z2, Z3, Z4, Z5 are defined the same as in 1);

Ring A is absent or optionally substituted benzene ring, in the case where the benzene ring is substituted, the substituent is one or more substituents selected from: halogen, nitro, cyano, C1-C3 alkyl, C1-C3 alkoxy, C1-C3 oxygen-containing alkyl, C1-C3 fluorine-containing alkyl, C1-C3 fluorine-containing alkoxy; preferably, the substituent is 1 or 2 substituents selected from: halogen, nitro, C1-C3 alkoxy; more preferably, the substituent is 1 or 2 substituents selected from: F, Cl, nitro, methoxy;

X– is an anion of a pharmaceutically acceptable inorganic or organic acid salt;

However, the following compounds are excluded:

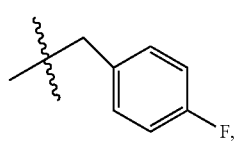 [SMILES: *Cc1ccc(F)cc1]

compounds a, b, c, d, e, f, g, h, i, j, k, l, m:

compound a: R1 is C16H33-, R2 is CH3-, R3 is

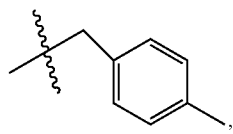 [SMILES: *Cc1ccc(C)cc1]

X– is Br–;

compound b: R1 is C16H33-, R2 is CH3-, R3 is

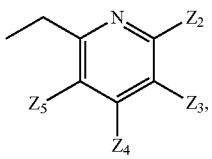

X– is Br–;

compound c: R1 is C16H33-, R2 is CH3-, R3 is

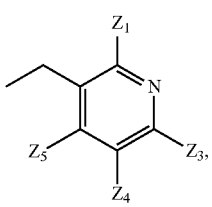

X– is Br–;

compound d: R1 is C16H33-, R2 is CH3-, R3 is

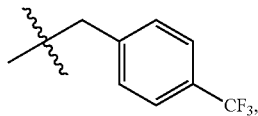

X- is Br-;

compound e: R1 is C16H33-, R2 is CH3-, R3 is

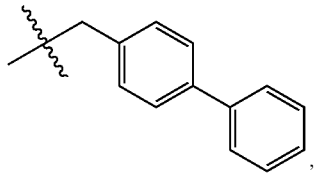 [SMILES: *Cc1ccc(-c2ccccc2)cc1]

X- is Br-;

compound f: R1 is C4H9-, R2 is CH3-, R3 is

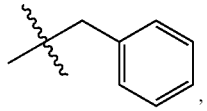 [SMILES: *Cc1ccccc1]

X- is I-;

compound g: R1 is C8H17-, R2 is CH3-, R3 is

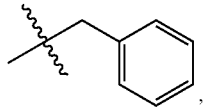

X- is I-;

compound h: R1 is C12H25-, R2 is CH3-, R3 is

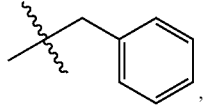

X- is I-;

compound i: R1 is C14H29-, R2 is CH3-, R3 is

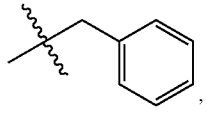 [SMILES: *Cc1ccccc1]

X- is I-;

compound j: R1 is C16H33-, R2 is CH3-, R3 is

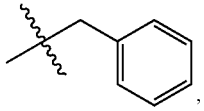

X- is I-;

compound k: R1 is C18H37-, R2 is CH3-, R3 is

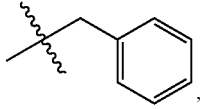

X- is I-;

compound l: R1 is C20H41-, R2 is CH3-, R3 is

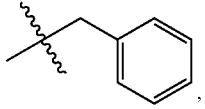

X is I-.

compound m: R1 is C22H45-, R2 is CH3-, R3 is

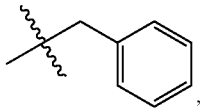

X is I-.

In some embodiments, R1 is selected from C1-C24 alkyl.
In some embodiments, R1 is selected from C1-C22 alkyl.
In some embodiments, R2 is selected from H, C1-C4 alkyl, C3 cycloalkyl.
In some embodiments, R2 is selected from H, methyl, ethyl, isopropyl, t-butyl, cyclopropyl.
In some embodiments, R3 is

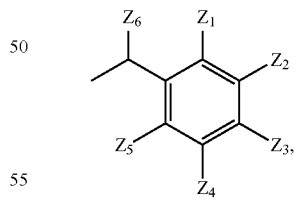

wherein any two of Z1, Z2, Z3, Z4, Z5 each are independently selected from the following groups, the rest being H:
H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl; preferably Z6 is H or methyl.

In some embodiments, R3 is

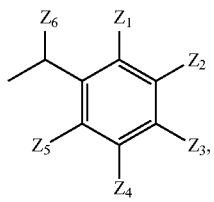

wherein one of Z1, Z2, Z3, Z4, Z5 is independently selected from the following groups, the rest being H:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl; preferably Z6 is H or methyl.

In some embodiments, Ring A is a substituted benzene ring, the substituent is 1 or 2 substituents selected from: halogen, nitro, C1-C3 alkoxy; more preferably, the substituent is 1 or 2 substituents selected from: F, Cl, nitro, methoxy.

In some embodiments, the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate.

In a second aspect, the present invention provides a compound of Formula I, a stereoisomer thereof, a prodrug thereof, a pharmaceutically acceptable salt thereof or a pharmaceutically acceptable solvate thereof,

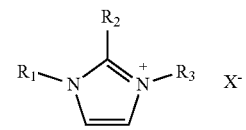

I wherein:

R1 is selected from C1-C24 alkyl, C1-C24 oxygen-containing alkyl, C1-C24 fluorine-containing alkyl, C1-C24 fluorine- and oxygen-containing alkyl;

R2 is selected from C1-C6 alkyl, C3-C6 cycloalkyl;

R3 is selected from

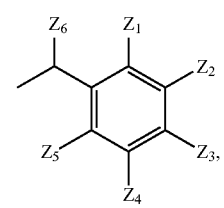

wherein Z1, Z2, Z3, Z4, Z5 each are independently selected from:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z2 and Z3 may form an oxygen-containing substituted or unsubstituted five- or six-membered ring; the substituent may be selected from the same substituents as Z1;

Z4 and Z5 may form a nitrogen-containing substituted or unsubstituted five- or six-membered ring; the substituent may be selected from the same substituents as Z1;

Z6 is selected from H, C1-C3 alkyl, C3-C6 cycloalkyl;

2)

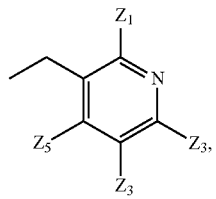

wherein Z2, Z3, Z4, Z5 are defined the same as in 1);

3)

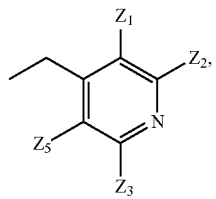

wherein Z2, Z3, Z4, Z5 are defined the same as in 1);

4)

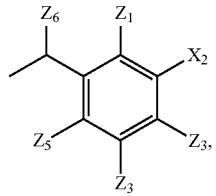

wherein Z2, Z3, Z4, Z5 are defined the same as in 1);
X− is an anion of a pharmaceutically acceptable inorganic or organic acid salt.

In some embodiments, R1 is selected from C1-C24 alkyl.
In some embodiments, R1 is selected from C1-C22 alkyl.
In some embodiments, R2 is selected from H, C1-C4 alkyl, C3 cycloalkyl.
In some embodiments, R2 is selected from H, methyl, ethyl, isopropyl, t-butyl, cyclopropyl.

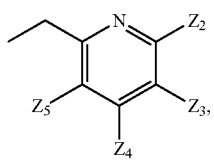

In some embodiments, R3 is Z4, wherein any two of Z1, Z2, Z3, Z4, Z5 each are independently selected from the following groups, the rest being H:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl.

In some embodiments, R3 is

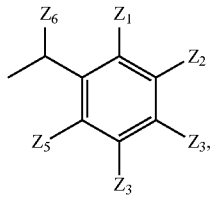

wherein any two of Z1, Z2, Z4, Z5 each are independently selected from the following groups, the rest and Z3 being H:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl; preferably Z6 is H.

In some embodiments, R3 is

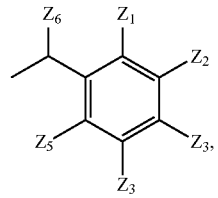

wherein Z1, Z5, or Z2, Z4, or Z1, Z4 in Z1, Z2, Z3, Z4, Z5 each are independently selected from the following groups, the rest being H:

H, F, Cl, Br, I, nitro, cyano;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl; preferably Z6 is H or methyl.

In some embodiments, R3 is

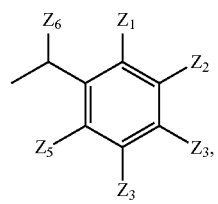

wherein one of Z1, Z2, Z3, Z4, Z5 is independently selected from the following groups, the rest being H:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl; preferably Z6 is H or methyl.

In some embodiments, the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate.

In a third aspect, the present invention provides the following compounds:

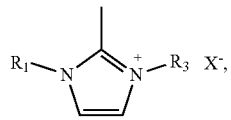
IA

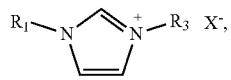
IB

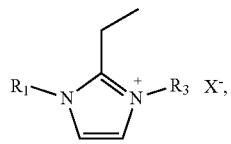
IC

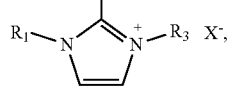
ID

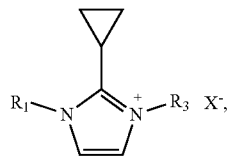
IE

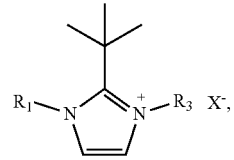
IF wherein, R1, R3 and X– are as defined above,
or a stereoisomer thereof, a prodrug thereof, a pharmaceutically acceptable salt thereof or a pharmaceutically acceptable solvate thereof.

In a fourth aspect, the present invention provides a compound of Formula II, a stereoisomer thereof, a prodrug thereof, a pharmaceutically acceptable salt thereof or a pharmaceutically acceptable solvate thereof:

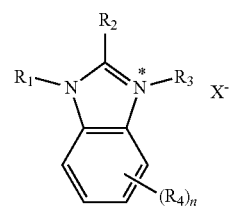
II wherein:
R1 is selected from C1-C24 alkyl, C1-C24 oxygen-containing alkyl, C1-C24 fluorine-containing alkyl, C1-C24 fluorine- and oxygen-containing alkyl;
R2 is selected from C1-C6 alkyl, C3-C6 cycloalkyl;
R3 is selected from

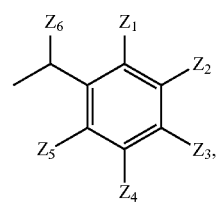

wherein Z1, Z2, Z3, Z4, Z5 each are independently selected from:
H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z2 and Z3 may form an oxygen-containing substituted or unsubstituted five- or six-membered ring; the substituent may be selected from the same substituents as Z1;

Z4 and Z5 may form a nitrogen-containing substituted or unsubstituted five- or six-membered ring; the substituent may be selected from the same substituents as Z1;

Z6 is selected from H, C1-C3 alkyl, C3-C6 cycloalkyl;

2)

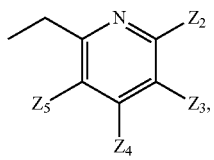

wherein Z2, Z3, Z4, Z5 are defined the same as in 1);

3)

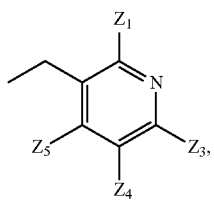

wherein Z2, Z3, Z4, Z5 are defined the same as in 1);

4)

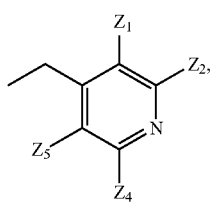

wherein Z2, Z3, Z4, Z5 are defined the same as in 1);

n is selected from 0, 1, 2;

4 independently is selected from H, halogen, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido, C1-C3 alkyl, C1-C3 alkoxy, C1-C3 oxygen-containing alkyl, C1-C3 fluorine-containing alkyl, C1-C3 fluorine-containing alkoxy;

X– is an anion of a pharmaceutically acceptable inorganic or organic acid salt.

In some embodiments, R1 is selected from C1-C24 alkyl.
In some embodiments, R1 is selected from C1-C16 alkyl.
In some embodiments, R1 is C16 alkyl.
In some embodiments, R2 is selected from H, C1-C4 alkyl, C3 cycloalkyl.
In some embodiments, R2 is selected from H, methyl, ethyl, isopropyl, t-butyl, cyclopropyl.
In some embodiments, R2 is methyl.
In some embodiments, R3 is

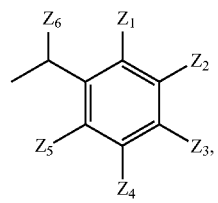

wherein any two of Z1, Z2, Z3, Z4, Z5 each are independently selected from the following groups, the rest being H:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl; preferably Z6 is H.

In some embodiments, R3 is

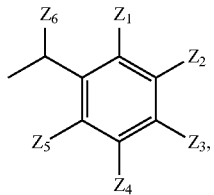

wherein any two of Z1, Z2, Z4, Z5 each are independently selected from the following groups, the rest and Z3 being H:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from is H, C1-C3 alkyl, C3-C6 cycloalkyl; preferably Z6 is H.

In some embodiments, R3 is

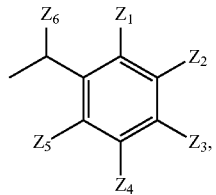

wherein Z1, Z5 in Z1, Z2, Z3, Z4, Z5 each are independently selected from the following groups, the rest being H:

H, F, Cl, Br, I, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

C1-C3 alkyl, C1-C3 alkoxy, C1-C3 oxygen-containing alkyl, C1-C3 fluorine-containing alkyl, C1-C3 fluorine-containing alkoxy;

Z6 is selected from H, C1-C3 alkyl, C3-C6 cycloalkyl.

In some embodiments, n is selected from 0, 1.

In some embodiments, R4 independently is selected from H, halogen, nitro, C1-C3 alkyl, C1-C3 alkoxy.

In some embodiments, R4 independently is selected from H, halogen, nitro, C1-C3 alkoxy.

In some embodiments, R4 independently is selected from H, F, Cl, nitro, methoxy.

In some embodiments, the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate.

In a fifth aspect, the present invention provides the following compounds:

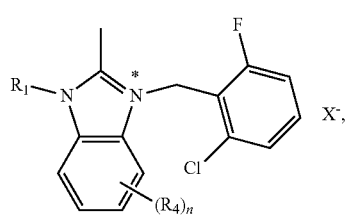

IIA

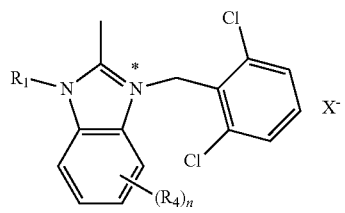

IIB

R1, R4, n and X− are as defined above,
or a stereoisomer thereof, a prodrug thereof, a pharmaceutically acceptable salt thereof or a pharmaceutically acceptable solvate thereof.

In the present invention, the pharmaceutically acceptable salt is an inorganic acid salt or an organic acid salt, wherein, the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate.

Unless otherwise indicated, the above groups and substituents have the ordinary meanings in the field of medicinal chemistry.

The term "C1-C24 alkyl" refers to any straight-chain or branched-chain group having 1 to 24 carbon atoms, such as methyl, ethyl, n-propyl, isopropyl, n-butyl, isobutyl, t-butyl, sec-butyl, n-pentyl, tert-amyl, n-hexyl and the following straight-chain or branched-chain alkyl: C7 alkyl, C8 alkyl, C9 alkyl, C10 alkyl, C11 alkyl, C12 alkyl, C13 alkyl, C14 alkyl, C15 alkyl, C16 alkyl, C17 alkyl, C18 alkyl, C19 alkyl, C20 alkyl, C21 alkyl, C22 alkyl, C23 alkyl, C24 alkyl and the like.

Moreover, the term "C1-C24 alkyl" includes straight-chain or branched-chain groups having a number of carbon atoms within intervals of any two integers in the range of 1 to 24 as endpoints. For example, "C1-C24 alkyl" includes C1-C22 alkyl, C1-C16 alkyl, C1-C4 alkyl, C2-C24 alkyl, C2-C16 alkyl, C6-C24 alkyl, C6-C16 alkyl, and etc. The above list is by way of example only and is not limiting the intervals.

The term "C1-C22 alkyl" refers to any straight-chain or branched-chain group having 1 to 22 carbon atoms, such as methyl, ethyl, n-propyl, isopropyl, n-butyl, isobutyl, t-butyl, sec-butyl, n-pentyl, tert-amyl, n-hexyl and the following straight-chain or branched-chain alkyl: C7 alkyl, C8 alkyl, C9 alkyl, C10 alkyl, C11 alkyl, C12 alkyl, C13 alkyl, C14 alkyl, C15 alkyl, C16 alkyl, C17 alkyl, C18 alkyl, C19 alkyl, C20 alkyl, C21 alkyl, C22 alkyl and the like.

The term "C1-C6 alkyl" refers to any straight-chain or branched-chain group having 1 to 6 carbon atoms, such as methyl, ethyl, n-propyl, isopropyl, n-butyl, isobutyl, t-butyl, sec-butyl, n-pentyl, tert-amyl, n-hexyl and the like.

The term "C1-C4 alkyl" refers to any straight-chain or branched-chain group having 1 to 4 carbon atoms, such as methyl, ethyl, n-propyl, isopropyl, n-butyl, isobutyl, t-butyl, sec-butyl and the like.

It should be noted that "oxygen-containing alkyl" refers to a group in which alkyl skeleton is substituted by one or more alkoxy groups, for example, methoxyethyl, methoxyethoxymethyl and the like.

For example, "C1-C24 oxygen-containing alkyl" refers to a group in which C1-C24 alkyl is substituted by one or more alkoxy groups, for example, methoxy C1-C24 alkyl, methoxyethoxy C1-C24 alkyl and the like.

Or, "C1-C3 oxygen-containing alkyl" refers to a group in which C1-C3 alkyl is substituted by one or more alkoxy groups, for example, methoxy C1-C3 alkyl, methoxyethoxy C1-C3 alkyl and the like.

"Fluorine-containing alkyl" refers to a group in which alkyl skeleton is substituted by one or more fluoro groups, for example, monofluoromethyl, difluoroethyl, trifluoromethyl and the like.

"C1-C24 fluorine-containing alkyl" refers to a group in which C1-C24 alkyl skeleton is substituted by one or more fluoro groups, e.g., C1-C24 alkyl substituted by 1-3 fluoro groups.

The term "C3-C6 cycloalkyl" refers to a 3-to 6-membered all-carbon monocyclic ring that may contain zero, one or more double bonds, but does not have a fully conjugated π-electron system. Examples of cycloalkyl include, but are not limited to, cyclopropyl, cyclobutyl, cyclopentyl, cyclopentenyl, cyclohexyl, cyclohexenyl, cyclohexadienyl.

The term "cyano" refers to —CN residue.

The term "nitro" refers to —NO2 group.

The terms "alkoxy", "cycloalkoxy" and derivatives thereof refer to any of the above-mentioned alkyl (for example, C1-C24 alkyl, C1-C6 alkyl and the like), cycloalkyl (for example, C3-C6 cycloalkyl), which is attached to the remainder of molecules through oxygen atom (—O—).

From all of the above description, it will be apparent to those skilled in the art that any group whose name is a compound name, for example, "fluorine-containing oxygen-containing alkyl" shall mean a moiety constructed from a derived moiety, such as the oxygen-containing alkyl substituted by the fluoro, wherein the alkyl is as defined above.

The term "oxygen-containing substituted or unsubstituted five- or six-membered ring" or "nitrogen-containing substituted or unsubstituted five- or six-membered ring" refers to five- or six-membered saturated or partially unsaturated carbon ring, wherein one or more carbon atoms are replaced by oxygen or nitrogen. Non-limiting examples are, for example, pyran, pyrrolidine, pyrroline, imidazoline, imidazolidine, pyrazolidine, pyrazoline, dihydrofuran, tetrahydrofuran, 1,3-dioxolan, piperidine, piperazine, morpholine, tetrahydropyrrole, etc.

In the above definitions of Z1, Z2, Z3, Z4, Z5 for R3, the expression "wherein, Z1, Z5, or Z2, Z4, or Z1, Z4 in Z1, Z2, Z3, Z4, Z5 each are independently selected from the following groups, the rest being H: (1) H, F, Cl, Br, I, nitro, cyano; (2) C1-C3 alkyl, C1-C3 alkoxy, C1-C3 oxygen-containing alkyl, C1-C3 fluorine-containing alkyl, C1-C3 fluorine-containing alkoxy" is meant that: "Z1, Z5 each are independently selected from" includes that Z1, Z5 each are independently any combination of any groups listed in "(1) H, F, Cl, Br, I, nitro, cyano; (2) C1-C3 alkyl, C1-C3 alkoxy, C1-C3 oxygen-containing alkyl, C1-C3 fluorine-containing alkyl, C1-C3 fluorine-containing alkoxy", "Z2, Z4 each are independently selected from" includes that Z2, Z4 each are independently any combination of any groups listed in "(1) H, F, Cl, Br, I, nitro, cyano; (2) C1-C3 alkyl, C1-C3 alkoxy, C1-C3 oxygen-containing alkyl, C1-C3 fluorine-containing alkyl, C1-C3 fluorine-containing alkoxy", "Z1, Z4 each are independently selected from" includes that Z1, Z4 each are independently any combination of any groups listed in "(1) H, F, Cl, Br, I, nitro, cyano; (2) C1-C3 alkyl, C1-C3 alkoxy, C1-C3 oxygen-containing alkyl, C1-C3 fluorine-containing alkyl, C1-C3 fluorine-containing alkoxy".

As used herein, unless otherwise indicated, the term "prodrug" refers to a derivative that can be hydrolyzed, oxidized or otherwise reacted under biological conditions (in vitro or in vivo) to provide a compound of the invention. Prodrugs can become active compounds only by carrying out the reaction under biological conditions, or they are inactive in their non-reacted form. Prodrugs can be generally prepared using known methods, for example, those methods described in Burger's Medicinal Chemistry and Drug Discovery (1995) 172-178, 949-982 (Manfred E. Wolff, ed. 5th edition).

As used herein, examples of the term "pharmaceutically acceptable salts of the compounds of formula (I)" are organic acid addition salts formed from organic acids that form pharmaceutically acceptable anions, including but not limited to formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate. Suitable inorganic acid salts may also be formed, including but not limited to hydrochloride, hydrobromide, hydroiodide, nitrate, bicarbonate and carbonate, sulfate or phosphate and the like.

Pharmaceutically acceptable salts can be obtained using standard procedures well known in the art, for example, by reacting a sufficient amount of a basic compound with a suitable acid that provides a pharmaceutically acceptable anion.

The term "treatment" as used herein generally refers to obtaining the desired pharmacological and/or physiological effect. The effect may be preventive according to complete or partial prevention of disease or its symptoms; and/or may be therapeutic according to partial or complete stabilization or cure of disease and/or side effects due to the disease. The term "treatment" as used herein encompasses any treatment on a patient's disease, including: (a) preventing the disease or symptom that occurs in a patient who is susceptible to the disease or symptom but not yet diagnosed to suffer from the disease; (b) suppressing symptoms of the disease, i.e., stopping its development; or (c) relieving symptoms of the disease, i.e., causing degeneration of the disease or symptom.

According to a specific embodiment of the present invention relating to the compound, a stereoisomer thereof, a prodrug thereof, or a pharmaceutically acceptable salt thereof or a pharmaceutically acceptable solvate thereof, the compound is one of the compounds described in the examples below.

In another aspect, the present invention provides a pharmaceutical composition comprising the compound, a stereoisomer thereof, a prodrug thereof, or a pharmaceutically acceptable salt thereof or pharmaceutically acceptable solvate thereof according to any one of the above embodiments, and a pharmaceutically acceptable carrier, diluent or excipient.

Methods for preparing a pharmaceutical composition comprising a certain amount of an active ingredient, are known or are obvious for a person skilled in the art according to the contents as disclosed in the invention. For example, as described in REMINGTON'S PHARMACEUTICAL SCIENCES, Martin, E. W., ed., Mack Publishing Company, 19th ed. (1995), methods for preparing a pharmaceutical composition comprise incorporating a suitable pharmaceutically acceptable excipient, carrier, diluent, etc.

The known methods for preparing a pharmaceutical preparation according to the invention include the conventional mixing, dissolving or freeze-drying methods. The compound according to the invention can be used to prepare into a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, or pressed into a table. For the treatment by oral administration, an active compound may be combined with one or more excipients, and be used in a form of a deglutible tablet, a buccal tablet, a troche, a capsule, an elixir, a suspension, a syrup, a wafer, etc. The composition and preparation shall comprise at least 0.1% of an active compound. The ratio of the composition to the preparation can be varied certainly, and the composition may account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc; a lubricant, such as magnesium stearate; and a sweeting agent, such as sucrose, fructose, lactose or aspartame; or a flavoring agent, such as peppermint, winter green oil or cherry flavor. When the unit dosage form is a capsule, in addition to the above types of materials, it may comprise a liquid carrier, such as vegetable oil or polyethylene glycol.

Various other materials may be present as a coating or change the physical form of a solid unit dosage form in other manners. For example, a tablet, a pill or a capsule may be coated with gelatin, wax, shellac or sugar etc. A syrup or elixir may comprise an active compound, sucrose or fructose as a sweeting agent, methyl p-hydroxybenzoate or propyl p-hydroxybenzoate as preservative, a dye and a flavoring agent (such as a cherry flavor or an orange flavor). Certainly, any material for preparing any unit dosage form should be pharmaceutically acceptable and be substantively not toxic in its applied amount. In addition, an active compound may be incorporated into a sustained release preparation and a sustained release device.

An active compound may also be administered intravenously or intraperitoneally by infusion or injection. An aqueous solution of an active compound or a salt thereof may be prepared, optionally, by mixing it with a non-toxic surfactant. A dispersible formulation in glycerol, liquid polyethylene glycol, glycerin triacetate and a mixture thereof and in oil may also be prepared. Under the common conditions of storage and use, the preparations may comprise a preservative in order to suppress the growth of microbes.

A pharmaceutical dosage form suitable for injection or infusion may include a sterile aqueous solution or a dispersible formulation or a sterile powder comprising an active ingredient (optionally encapsulated into a liposome) of an immediate preparation such as a solvent or a dispersible formulation suitable for sterile injection or infusion. Under all the conditions, the final dosage form shall be sterile, liquid and stable under the production and storage conditions. A liquid carrier may be a solution or a liquid disperse medium, including, for example, water, ethanol, polyols (such as glycerol, propylene glycol, and liquid macrogol, etc), vegetable oil, a non-toxic glyceride and a suitable mixture thereof. A suitable fluidity may be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal, etc). In many conditions, an isotonizing agent, such as sugar, buffer agent or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation method is vacuum drying and freeze drying techniques, which will result in the production of the powder of the active ingredient and any other desired ingredient present in the previous sterile filtration solution.

A useful solid carrier includes crushed solid (such as talc, clay, microcrystalline cellulose, silicon dioxide, and aluminum oxide etc). A useful liquid carrier includes water, ethanol or ethylene glycol or water-ethanol/ethylene glycol mixture, in which the compound of the invention may be dissolved or dispersed in an effective amount, optionally, with the aid of a non-toxic surfactant. An adjuvant (such as a flavor) and an additional antimicrobial agent may be added to optimize the property for a given use.

A thickener (such as synthetic polymer, fatty acid, fatty acid salt and ester, fatty alcohol, modified cellulose or modified inorganic material) may also be used with a liquid carrier to form a coatable paste, gel, ointment, soap and the like, and be directly applied to the skin of a user.

A therapeutically effective amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation may be present in a unit dosage form, which is a physical dispersion unit comprising a unit dose, suitable for administration to a human body and other mammalian body. A unit dosage form may be capsule (s) or tablet(s). Depending on the particular treatment involved, the amount of an active ingredient in a unit dose may be varied or adjusted between about 0.1 and about 1000 mg or more.

In addition, the present invention further includes use of various new drug dosage forms such as milk liposomes, microspheres and nanospheres, for example, medicaments prepared with the use of a particulate dispersion system including polymeric micelles, nanoemulsions, submicroemulsions, microcapsules, microspheres, liposomes and niosomes (also known as nonionic surfactant vesicles), etc.

In another aspect, the present invention further provides a preparation method of the compound according to any of the above embodiments, comprising the following steps:

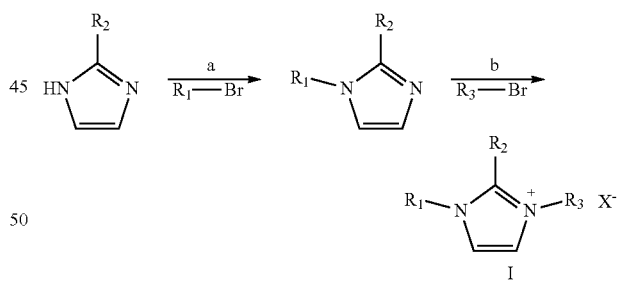

reaction conditions: (a) substitution reaction of brominated hydrocarbons; (b) substitution reaction of brominated hydrocarbons or

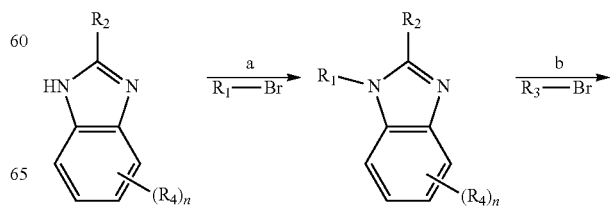

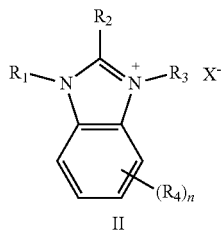

reaction conditions: (a) substitution reaction of brominated hydrocarbons under alkaline condition (such as sodium hydride, sodium t-butoxide and the like); (b) substitution reaction of brominated hydrocarbons.

In another aspect, the present invention further provides use of the compound according to any one of the above embodiments, a stereoisomer thereof, a prodrug thereof, or a pharmaceutically acceptable salt thereof or a pharmaceutically acceptable solvate thereof, and a pharmaceutical composition comprising the compound in the manufacture of a medicament for inhibiting cholesterol synthesis, for lowering fatty acid synthesis, for preventing and/or treating obesity, for preventing and/or treating diabetes, for preventing and/or treating tumor, for preventing and/or treating Parkinson's disease, for preventing and/or treating Alzheimer's disease or for prolonging the lifespan of mammals.

EXPERIMENTAL SECTION

Regarding the examples described below, the compounds of the present invention are synthesized using the methods described herein or other methods well known in the art.

General Methods of Purification and Analysis

Thin layer chromatography was carried out on a silica gel GF254 precoated plate (Qingdao Marine Chemical Plant). Column chromatography was carried out by silica gel (300-400 mesh, Yantai Zhihuangwu Silica Gel Development Reagent Factory) under medium pressure or by a pre-packed silica gel cartridge (ISCO or Welch) with the use of an ISCO Combiflash Rf200 rapid purification system. The ingredient was developed by UV light (k: 254 nm) or iodine vapor. When necessary, the compound was prepared by preparative HPLC and purified by a Waters Symmetry C18 (19×50 mm, 5 μm) column or a Waters X Terra RP 18 (30×150 mm, 5 μm) column, wherein a Waters preparative HPLC 600 equipped with a 996 Waters PDA detector and Micromass mod. ZMD single quadrupole mass spectrometry (electrospray ionization, cationic mode) were used. Method 1: Phase A: 0.1% TFA/MeOH 95/5; Phase B: MeOH/H2O 95/5. Gradient: proceeding at 10 to 90% B for 8 min, keeping at 90% B for 2 min; flow rate 20 mL/min. Method 2: Phase A: 0.05% NH4OH/MeOH 95/5; Phase B: MeOH/H2O 95/5. Gradient: proceeding at 10 to 100% B for 8 min, keeping at 100% B for 2 min. Flow rate 20 mL/min.

1H-NMR spectra were recorded in DMSO-d6 or CDCl3 via a Bruker Avance 600 spectrometer (for 1H) operated at 600 MHz. The residual solvent signal was used as a reference (δ=2.50 or 7.27 ppm). Chemical shift (δ) was reported in parts per million (ppm) and coupling constant (J) in Hz. The following abbreviations were used for peak splitting: s=single; br. s.=wide signal; d=double; t=triple; m=multiple; dd=double double.

Electrospray (ESI) mass spectra were obtained via a Finnigan LCQ ion trap.

Unless otherwise indicated, all final compounds were homogeneous (with purity not less than 95%), as determined by high performance liquid chromatography (HPLC). HPLC-UV-MS analysis for evaluation of compound purity was performed by combining an ion trap MS device and an HPLC system SSP4000 (Thermo Separation Products) equipped with an autosampler LC Pal (CTC Analytics) and a UV6000LP diode array detector (UV detection 215-400 nm). Device control, data acquisition and processing were performed with Xcalibur 1.2 software (Finnigan). HPLC chromatography was carried out at room temperature and a flow rate of 1 mL/min using a Waters X Terra RP 18 column (4.6×50 mm; 3.5 μm). Mobile phase A was ammonium acetate 5 mM buffer (pH 5.5 with acetic acid): acetonitrile 90:10, mobile phase B was ammonium acetate 5 mM buffer (pH 5.5 with acetic acid): acetonitrile 10:90; proceeding at a gradient of 0 to 100% B for 7 min and then keeping at 100% B for 2 min before rebalancing.

Reagent purification was carried out in accordance with the book Purification of Laboratory Chemicals (Perrin, D. D., Armarego, W. L. F. and Perrins Eds, D. R.; Pergamon Press: Oxford, 1980). Petroleum ether was 60-90° C. fraction, ethyl acetate, methanol, dichloromethane were all analytically pure.

Mode of Carrying Out the Invention

The embodiments of the present invention are described in detail below by way of specific examples, but in any case they cannot be construed as limiting the present invention.

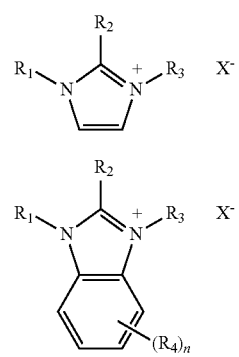

The above compounds of formulas were divided into two types for preparation.

The Compound of Formula I:

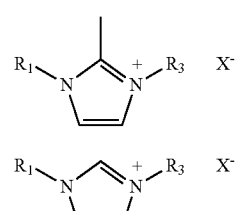

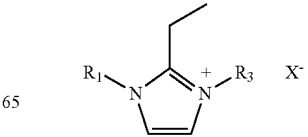

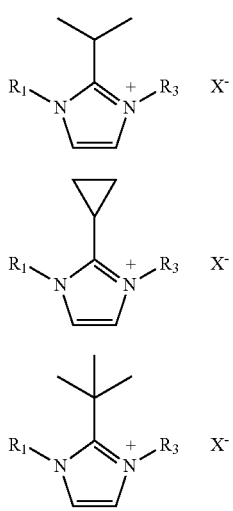

Synthetic Scheme I of Compound IA

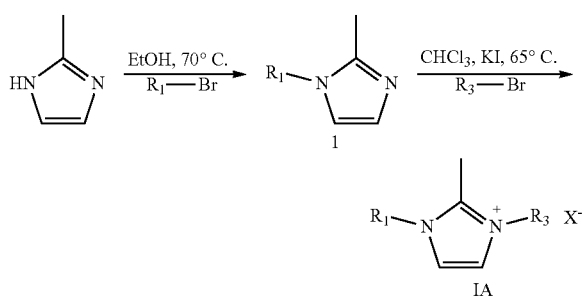

Preparation of Compound 1

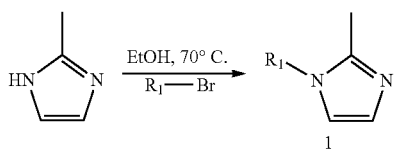

Compound 2-methylimidazole (821 mg, 10 mmol) was dissolved in 10 mL of ethanol, brominated alkane was added to the solution (12 mmol) and then stirred in an oil bath at 70° C., until complete reaction of 2-methylimidazole (LC-MS tracking). After the reaction stopped, the system was concentrated, and subjected to silica gel column chromatography (dichloromethane/methanol), to obtain compound 1-alkyl-2-methylimidazole (1).

Preparation of Compound IA

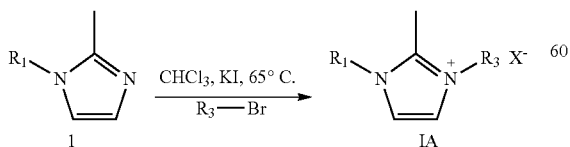

Polysubstituted benzyl bromide (0.23 mmol) and optional KI (74.7 mg, 0.462 mmol) were dissolved successively in 1.5 mL of chloroform, stirred in an oil bath at 65° C. under airtight conditions for 20 min, compound 1 (0.154 mmol) was then added to the system, followed by further stirring in an oil bath at 65° C. under airtight conditions until complete reaction (LC-MS tracking). After the reaction stopped, the system was filtered, the filtrate was concentrated, and subjected to silica gel column chromatography (dichloromethane/methanol), to obtain compound IA.

The implementation of the synthetic scheme I of compound IA is described as follows.

Compound IA-1:

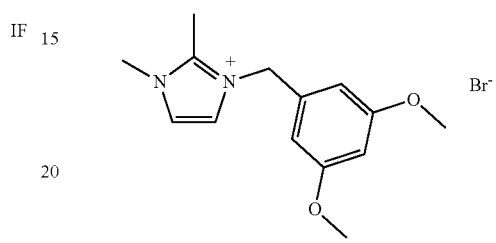

2-Methylimidazole (328.4 mg, 4 mmol) as raw material B (Appendix 1) was dissolved in 4 mL of ethanol, bromomethane (455.7 mg, 4.8 mmol) as raw material A (Appendix 1) was added to the solution, and the system was stirred in an oil bath at 70° C. for 10 h. Then, the system was concentrated, and subjected to silica gel column chromatography (dichloromethane/methanol=20/1), to obtain compound 1,2-dimethylimidazole (150.8 mg, 39.2%).

3,5-Dimethoxybenzyl bromide (46.2 mg, 0.2 mmol) as raw material C (Appendix 1) and optional KI (49.8 mg, 0.3 mmol) (CAS: 7681-11-0, Energy, Shanghai) were dissolved successively in 1.5 mL of chloroform, stirred in an oil bath at 65° C. under airtight conditions for 20 min, 1,2-dimethylimidazole (10 mg, 0.1 mmol) was then added to the system, followed by further stirring in an oil bath at 65° C. under airtight conditions for 6 h. After the reaction stopped, the system was filtered, the filtrate was concentrated, and subjected to silica gel column chromatography (dichloromethane/methanol=12/1), to obtain compound IA-1 (29.5 mg, 90.2%).

2. Compounds IA-2~IA-98 could be synthesized by a similar method. Please see the corresponding raw materials in Appendix 1.

3. Compounds IB, IC, ID, IE, IF each could be synthesized by a similar method, with the corresponding raw materials listed in Appendix 1.

Synthetic Scheme II of Compound IA

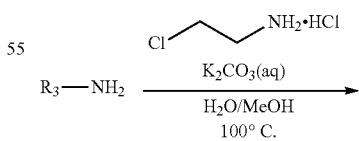

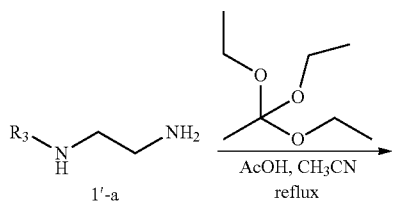

-continued

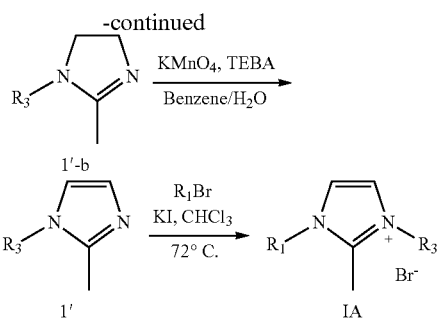

1'-b

IA

Preparation of Compound 1'-a

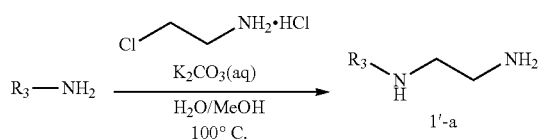

α-Substituted benzyl amine (10 mmol) was dissolved in 8 mL of methanol and 2 mL of water, and stirred in an oil bath at 100° C.; 2-chloroethylamine hydrochloride (580 mg, 5 mmol) was dissolved in 8 mL of water, adjusted with saturated potassium carbonate solution to pH=7, slowly added dropwise to the above solution, stirred in an oil bath at 100° C. for 3 h, and then the reaction was stopped. The reaction system was cooled to room temperature, 20 mL of 2N aqueous solution of sodium hydroxide and 50 mL of dichloromethane were added under the condition of rapid stirring, followed by liquid-liquid separation, and the aqueous phase was extracted by dichloromethane (3×40 mL), the organic phase was collected, washed with saturated sodium chloride solution, dried with anhydrous sodium sulfate and concentrated. The obtained product was subjected to silica gel column chromatography (dichloromethane/methanol) to obtain compound 1'-a (1.99 mmol).

Preparation of Compound 1'-b

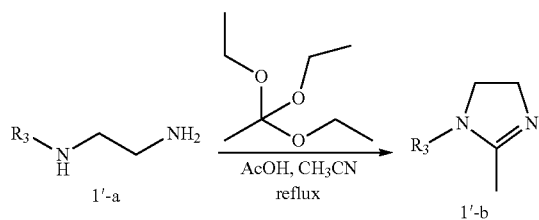

The obtained compound 1'-a was completely dissolved in 12 mL of acetonitrile, triethyl orthoacetate (388 μL, 2.12 mmol) and acetic acid (122 μL, 2.12 mmol) were added dropwise thereto, followed by refluxing and stirring under nitrogen protection for 3.5 h, and then the reaction was stopped. The reaction system was cooled to room temperature, concentrated, and dissolved with 2N aqueous solution of sodium hydroxide (20 mL) and dichloromethane (2×40 mL), followed by extraction and liquid-liquid separation, the organic phase was collected, washed with saturated sodium chloride solution, dried with anhydrous sodium sulfate and concentrated, to obtain compound 1'-b (1.94 mmol).

Preparation of Compound 1'

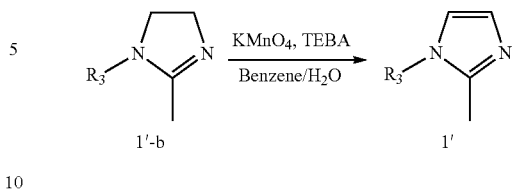

Compound 1'-b (0.8 mmol) was dissolved in benzene (3 mL), potassium permanganate (188 mg, 1.19 mmol) was dissolved in water (6 mL), the two phases were mixed, benzyltriethyl ammonium bromide (10.9 mg, 0.04 mmol) was added thereto, followed by stirring vigorously at room temperature for 4 h, and then the reaction was stopped. The reaction system was diluted with dichloromethane, filtered with diatomaceous earth, rinsed with dichloromethane (100 mL) and water (100 mL), the filtrate was subjected to liquid-liquid separation, the organic phase was collected, washed with saturated sodium chloride solution, dried with anhydrous sodium sulfate and concentrated, to obtain compound 1' (0.43 mmol).

Preparation of Compound IA

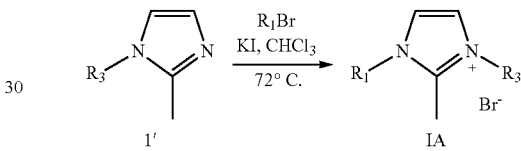

Brominated alkane (0.75 mmol) and optional KI (187 mg, 1.13 mmol) were dissolved in 2 mL of chloroform, and stirred in an oil bath at 72° C. under sealed condition for half an hour, then compound 1' (0.43 mmol) was dissolved in 1 mL of chloroform and added to the above system, followed by further stirring in an oil bath at 72° C. for 12 h, and then the reaction was stopped. The system was filtered, concentrated, subjected to silica gel column chromatography (dichloromethane/methanol), purified by reverse phase preparative HPLC (using 0.35% trifluoroacetic acid-containing aqueous solution and methanol as mobile phase), and vacuum concentrated to obtain compound I (0.086 mmol).

Compounds IB, IC, ID, IE, IF each could be synthesized by a similar method.

The implementation of the synthetic scheme II of compound IA is described as follows.

Compound IA-99:

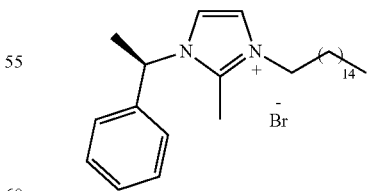

R(+)-α-methylbenzyl amine (1211.8 mg, 10 mmol) (CAS: 3886-69-9, Bide, Shanghai) was dissolved in 8 mL of methanol and 2 mL of water, and stirred in an oil bath at 100° C.; 2-chloroethylamine hydrochloride (580 mg, 5 mmol) (CAS: 870-24-6, Bide, Shanghai) was dissolved in 8 mL of water, adjusted with saturated potassium carbonate solution to pH=7, slowly added dropwise to the above solution, stirred in an oil bath at 100° C. for 3 h, and then the reaction was stopped. The reaction system was cooled to room temperature, 20 mL of 2N aqueous solution of sodium hydroxide and 50 mL of dichloromethane were added under the condition of rapid stirring, followed by liquid-liquid separation, the aqueous phase was extracted by dichloromethane (3×40 mL), the organic phase was collected, washed with saturated sodium chloride solution, dried with anhydrous sodium sulfate and concentrated. The obtained product was subjected to silica gel column chromatography (dichloromethane/methanol=10/1) to obtain compound

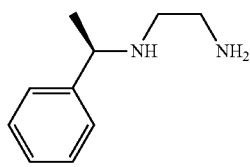

(327 mg, 40%).
Compound

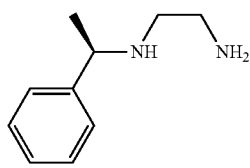

(1.99 mmol, 327 mg) was dissolved in 12 mL of acetonitrile, triethyl orthoacetate (388 μL, 2.12 mmol) (CAS: 78-39-7, Meryer, Shanghai) and acetic acid (122 μL, 2.12 mmol) were added dropwise thereto, followed by refluxing and stirring under nitrogen protection for 3.5 h, and then the reaction was stopped. The reaction system was cooled to room temperature, concentrated, and dissolved with 2N aqueous solution of sodium hydroxide (20 mL) and dichloromethane (2×40 mL), followed by extraction and liquid-liquid separation, the organic phase was collected, washed with saturated sodium chloride solution, dried with anhydrous sodium sulfate and concentrated, to obtain compound

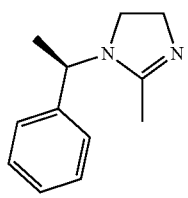

(365 mg, 97%).
Compound

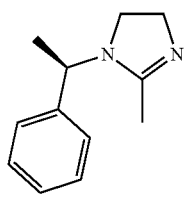

(0.8 mmol, 150 mg) was dissolved in benzene (3 mL), potassium permanganate (1.19 mmol, 188 mg) (CAS: 7722-64-7, Hangzhou Xiaoshan, Zhejiang) were dissolved in water (6 mL), the two phases were mixed, benzyltriethyl ammonium bromide (0.04 mmol, 10.9 mg) (CAS: 5197-95-5, Macklin, Shanghai) was added thereto, followed by stirring vigorously at room temperature for 4 h, and then the reaction was stopped. The reaction system was diluted with dichloromethane, filtered with diatomaceous earth, rinsed with dichloromethane (100 mL) and water (100 mL), the filtrate was subjected to liquid-liquid separation, the organic phase was collected, washed with saturated sodium chloride solution, dried with anhydrous sodium sulfate and concentrated, to obtain compound

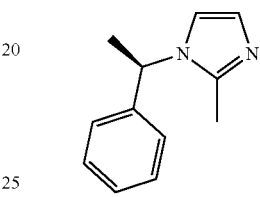

(80 mg, 53.7%).

1-Bromohexadecane (0.75 mmol, 229.8 mg) (CAS: 112-82-3, Macklin, Shanghai) and optional KI (187 mg, 1.13 mmol) (CAS: 7681-11-0, Energy, Shanghai) were dissolved in 2 mL of chloroform, stirred in an oil bath at 72° C. under sealed condition for half an hour, then compound

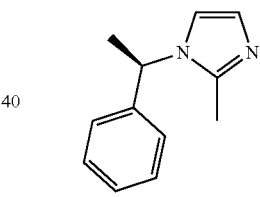

(0.37 mmol, 70 mg) was dissolved in 1 mL of chloroform and added to the above system, followed by further stirring in an oil bath at 72° C. for 12 h, and then the reaction was stopped. The system was filtered, concentrated, subjected to silica gel column chromatography (dichloromethane/methanol=40/1), purified by reverse phase preparative HPLC (using 0.35% trifluoroacetic acid-containing aqueous solution and methanol as mobile phase), and vacuum concentrated to obtain compound

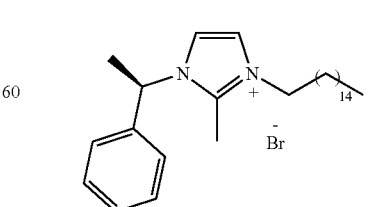

(42.4 mg, 22.9%).

2. Compound IA-100:

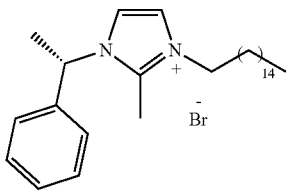

Using compound (S)-(−)-α-methylbenzyl amine (CAS: 2627-86-3, Bide, Shanghai) as starting raw material, compound IA-100 was synthesized by a method similar to that for the synthesis of IA-99.

3. Compound IA-101:

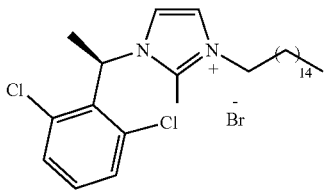

Using compound (R)-1-(2,6-dichlorophenyl)ethylamine hydrochloride (CAS: 1131737-05-7, Efebio, Shanghai) as starting raw material, compound IA-101 was synthesized by a method similar to that for the synthesis of IA-99.

4. Compound IA-102:

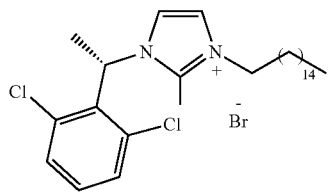

Using compound (S)-1-(2,6-dichlorophenyl)ethylamine hydrochloride (CAS: 121443-79-6, Efebio, Shanghai) as starting raw material, compound IA-102 was synthesized by a method similar to that for the synthesis of IA-99.

TABLE 1

Structure and characterization of compounds IA-IF

| No. | Structure | 1H NMR and/or MS data |
|---|---|---|
| IA-1 | 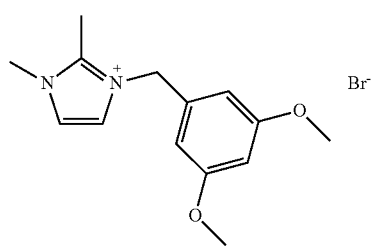 | 1H NMR (600 MHz, Chloroform-d) δ 7.49 (d, J = 2.1 Hz, 1H), 7.40 (d, J = 2.1 Hz, 1H), 6.46 (d, J = 2.2 Hz, 2H), 6.41 (d, J = 2.2 Hz, 1H), 5.36 (s, 2H), 3.93 (s, 3H), 3.77 (s, 6H), 2.79 (s, 3H). MS (ESI) m/z: 247 [M + H]+ |
| IA-2 | 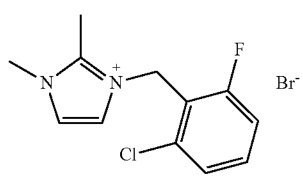 | 1H NMR (600 MHz, Chloroform-d) δ 7.69 (d, J = 2.2 Hz, 1H), 7.40 (td, J = 8.3, 6.0 Hz, 1H), 7.33-7.27 (m, 1H), 7.18 (d, J = 2.1 Hz, 1H), 7.15-7.08 (m, 1H), 5.52 (d, J = 1.7 Hz, 2H), 4.01 (s, 3H), 2.92 (s, 3H). MS (ESI) m/z: 240 [M + H]+ |
| IA-3 | 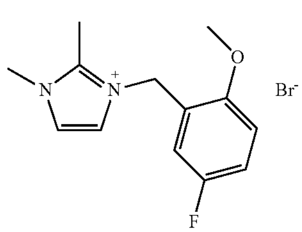 | 1H NMR (600 MHz, Chloroform-d) δ 7.53 (d, J = 2.2 Hz, 1H), 7.27 (d, J = 2.1 Hz, 1H), 7.21 (dd, J = 8.1, 3.1 Hz, 1H), 7.05 (ddd, J = 9.1, 7.9, 3.1 Hz, 1H), 6.85 (dd, J = 9.1, 4.2 Hz, 1H), 5.33 (s, 2H), 3.96 (s, 3H), 3.81 (s, 3H), 2.85 (s, 3H). MS (ESI) m/z: 235 [M + H]+ |

TABLE 1-continued

Structure and characterization of compounds IA-IF

| No. | Structure | 1H NMR and/or MS data |
|---|---|---|
| IA-4 | 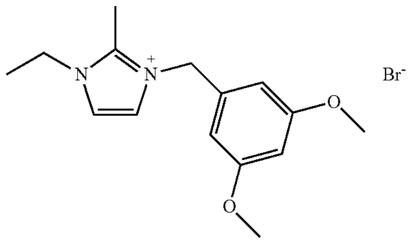 | 1H NMR (600 MHz, Chloroform-d) δ 7.47 (d, J = 2.2 Hz, 1H), 7.43 (d, J = 2.2 Hz, 1H), 6.46 (d, J = 2.3 Hz, 2H), 6.39 (s, 1H), 5.38 (s, 2H), 4.24 (q, J = 7.3 Hz, 2H), 3.75 (s, 6H), 2.78 (s, 3H), 1.49 (t, J = 7.3 Hz, 3H). MS (ESI) m/z: 261 [M + H]+ |
| IA-5 | 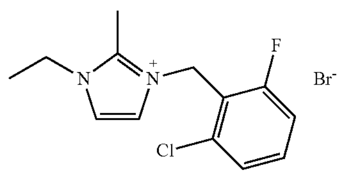 | 1H NMR (600 MHz, Chloroform-d) δ 7.70 (d, J = 2.2 Hz, 1H), 7.44-7.34 (m, 1H), 7.28 (dt, J = 8.1, 1.1 Hz, 1H), 7.20 (d, J = 2.1 Hz, 1H), 7.10 (ddd, J = 9.4, 8.3, 1.1 Hz, 1H), 5.54 (d, J = 1.8 Hz, 2H), 4.35 (q, J = 7.3 Hz, 2H), 2.93 (s, 3H), 1.49 (t, J = 7.3 Hz, 3H). MS (ESI) m/z: 254 [M + H]+ |
| IA-6 | 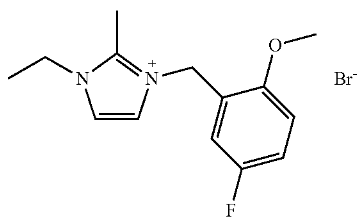 | 1H NMR (600 MHz, Chloroform-d) δ 7.48 (d, J = 2.2 Hz, 1H), 7.28 (d, J = 2.2 Hz, 1H), 7.22 (dd, J = 8.1, 3.1 Hz, 1H), 7.04 (ddd, J = 9.2, 7.9, 3.1 Hz, 1H), 6.85 (dd, J = 9.1, 4.3 Hz, 1H), 5.34 (s, 2H), 4.27 (q, J = 7.3 Hz, 2H), 3.80 (s, 3H), 2.85 (s, 3H), 1.49 (t, J = 7.4 Hz, 3H). MS (ESI) m/z: 249 [M + H]+ |
| IA-7 | 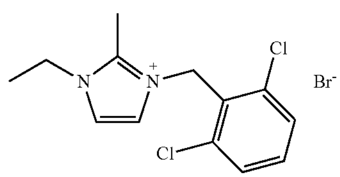 | 1H NMR (600 MHz, Chloroform-d) δ 7.45 (d, J = 7.9 Hz, 2H), 7.41-7.36 (m, 2H), 6.92 (s, 1H), 5.53 (s, 2H), 4.41-4.09 (m, 2H), 2.84 (s, 3H), 1.49 (d, J = 5.8 Hz, 3H). MS (ESI) m/z: 270 [M + H]+ |
| IA-8 | 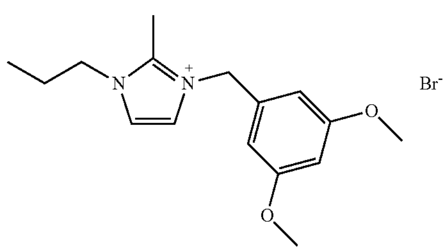 | 1H NMR (600 MHz, DMSO-d6) δ 7.81-7.63 (m, 1H), 7.55 (s, 2H), 6.50 (s, 1H), 6.45 (d, J = 2.3 Hz, 1H), 5.31 (s, 2H), 4.04-3.95 (m, 2H), 3.73 (s, 3H), 2.54 (s, 6H), 1.75 (p, J = 7.4 Hz, 2H), 0.86 (td, J = 7.5, 2.4 Hz, 3H). MS (ESI) m/z: 275 [M + H]+. |
| IA-9 | 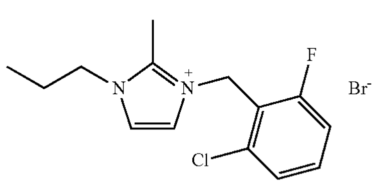 | 1H NMR (600 MHz, DMSO-d6) δ 7.72 (d, J = 2.2 Hz, 1H), 7.56 (td, J = 8.2, 6.3 Hz, 1H), 7.49-7.43 (m, 2H), 7.38 (t, J = 9.0 Hz, 1H), 5.51 (s, 2H), 4.11 (t, J = 7.2 Hz, 2H), 2.69 (s, 3H), 1.73 (dt, J = 14.5, 7.2 Hz, 2H), 0.84 (t, J = 7.4 Hz, 3H). MS (ESI) m/z: 268 [M + H]+. |
| IA-10 | 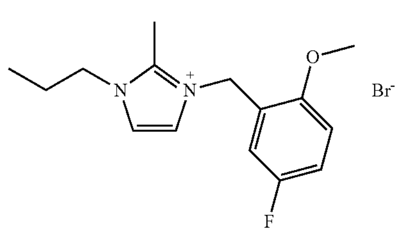 | 1H NMR (600 MHz, DMSO-d6) δ 7.68 (s, 1H), 7.58 (s, 1H), 7.10 (s, 3H), 5.29 (s, 2H), 4.09 (t, J = 7.5 Hz, 2H), 3.79 (s, 3H), 2.66 (s, 3H), 1.76 (q, J = 7.4 Hz, 2H), 0.89-0.81 (m, 3H). MS (ESI) m/z: 263 [M + H]+. |

TABLE 1-continued

Structure and characterization of compounds IA-IF

| No. | Structure | 1H NMR and/or MS data |
|---|---|---|
| IA-11 | 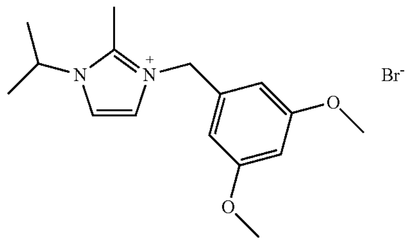 | 1H NMR (600 MHz, Chloroform-d) δ 7.42 (d, J = 2.3 Hz, 1H), 7.34 (d, J = 2.3 Hz, 1H), 6.51 (d, J = 2.3 Hz, 2H), 6.42 (s, 1H), 5.43 (s, 2H), 4.70 (p, J = 6.7 Hz, 1H), 3.78 (s, 6H), 2.87 (s, 3H), 1.56 (d, J = 6.7 Hz, 6H). MS (ESI) m/z: 275 [M + H]+. |
| IA-12 | 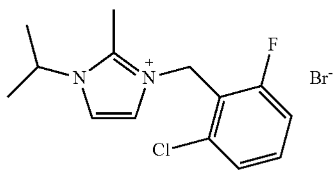 | 1H NMR (600 MHz, Chloroform-d) δ 7.48 (d, J = 2.4 Hz, 1H), 7.40 (td, J = 8.4, 6.2 Hz, 1H), 7.31 (d, J = 8.2 Hz, 1H), 7.26 (s, 1H), 7.12 (t, J = 8.8 Hz, 1H), 5.60 (d, J = 1.6 Hz, 2H), 4.83 (p, J = 6.6 Hz, 1H), 3.02 (s, 3H), 1.57 (d, J = 6.7 Hz, 6H). MS (ESI) m/z: 268 [M + H]+. |
| IA-13 | 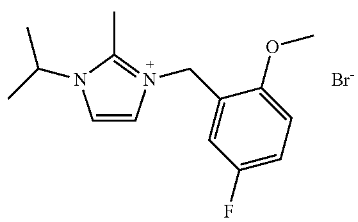 | 1H NMR (600 MHz, Chloroform-d) δ 7.36 (d, J = 2.3 Hz, 1H), 7.31 (d, J = 2.3 Hz, 1H), 7.23 (dd, J = 8.1, 3.1 Hz, 1H), 7.07 (ddd, J = 9.1, 7.9, 3.1 Hz, 1H), 6.87 (dd, J = 9.0, 4.2 Hz, 1H), 5.38 (s, 2H), 4.77 (p, J = 6.7 Hz, 1H), 3.82 (s, 3H), 2.93 (s, 3H), 1.57 (d, J = 6.6 Hz, 6H). MS (ESI) m/z: 263 [M + H]+. |
| IA-14 | 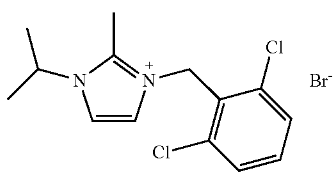 | 1H NMR (600 MHz, Chloroform-d) δ 7.46 (dd, J = 7.9, 2.7 Hz, 2H), 7.38 (s, 1H), 7.29 (s, 1H), 6.95 (d, J = 23.4 Hz, 1H), 5.57 (d, J = 19.5 Hz, 2H), 4.30 (s, 1H), 2.94 (d, J = 33.3 Hz, 3H), 1.57 (s, 6H). MS (ESI) m/z: 284 [M + H]+ |
| IA-15 | 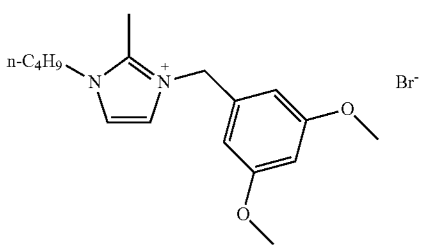 | 1H NMR (600 MHz, Chloroform-d) δ 7.48 (d, J = 2.1 Hz, 1H), 7.45 (d, J = 2.1 Hz, 1H), 6.44 (d, J = 2.2 Hz, 2H), 6.36 (t, J = 2.2 Hz, 1H), 5.40 (s, 2H), 4.14 (t, J = 7.5 Hz, 2H), 3.72 (s, 6H), 2.75 (s, 3H), 1.76 (tt, J = 9.4, 6.8 Hz, 2H), 1.36-1.30 (m, 2H), 0.89 (t, J = 7.3 Hz, 3H). MS (ESI) m/z: 289 [M + H]+. |
| IA-16 | 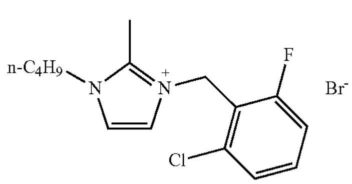 | 1H NMR (600 MHz, Chloroform-d) δ 7.61 (d, J = 2.1 Hz, 1H), 7.39 (td, J = 8.2, 6.1 Hz, 1H), 7.29 (dt, J = 8.1, 1.1 Hz, 1H), 7.20 (d, J = 2.1 Hz, 1H), 7.14-7.08 (m, 1H), 5.56 (d, J = 1.6 Hz, 2H), 4.27 (t, J = 7.5 Hz, 2H), 2.93 (s, 3H), 1.86-1.72 (m, 2H), 1.40-1.35 (m, 2H), 0.93 (t, J = 7.3 Hz, 3H). MS (ESI) m/z: 282 [M + H]+. |
| IA-17 | 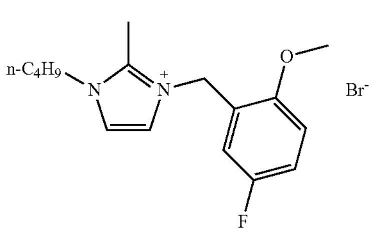 | 1H NMR (600 MHz, Chloroform-d) δ 7.48 (d, J = 2.2 Hz, 1H), 7.30 (d, J = 2.3 Hz, 1H), 7.24 (dd, J = 8.1, 3.1 Hz, 1H), 7.03 (td, J = 8.5, 3.1 Hz, 1H), 6.83 (dd, J = 9.1, 4.2 Hz, 1H), 5.36 (s, 2H), 4.20 (t, J = 7.5 Hz, 2H), 3.78 (s, 3H), 2.84 (s, 3H), 1.78 (p, J = 7.7 Hz, 2H), 1.35 (dd, J = 15.5, 7.8 Hz, 2H), 0.90 (t, J = 7.3 Hz, 3H). MS (ESI) m/z: 277 [M + H]+. |

TABLE 1-continued

Structure and characterization of compounds IA-IF

| No. | Structure | 1H NMR and/or MS data |
|---|---|---|
| IA-18 | 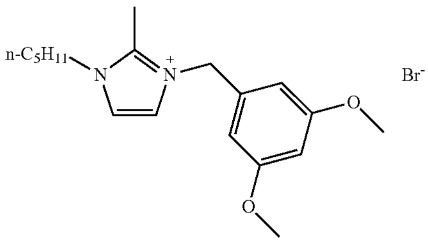 | 1H NMR (600 MHz, Chloroform-d) δ 7.48 (d, J = 2.1 Hz, 1H), 7.44 (d, J = 2.1 Hz, 1H), 6.42 (d, J = 2.2 Hz, 2H), 6.33 (s, 1H), 5.39 (s, 2H), 4.13-4.10 (m, 2H), 3.70 (s, 6H), 2.72 (s, 3H), 1.76 (p, J = 7.5 Hz, 2H), 1.29-1.23 (m, 4H), 0.81 (t, J = 6.8 Hz, 3H). MS (ESI) m/z: 303 [M + H]+. |
| IA-19 | 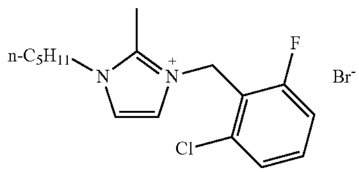 | 1H NMR (600 MHz, Chloroform-d) δ 7.58 (dt, J = 5.0, 2.3 Hz, 1H), 7.36 (td, J = 5.8, 2.8 Hz, 1H), 7.25-7.21 (m, 1H), 7.13 (s, 1H), 7.09-7.02 (m, 1H), 5.48 (s, 2H), 4.19-4.16 (m, 2H), 2.89-2.84 (m, 3H), 1.81-1.69 (m, 2H), 1.30-1.21 (m, 4H), 0.80-0.78 (m, 3H). MS (ESI) m/z: 296 [M + H]+. |
| IA-20 | 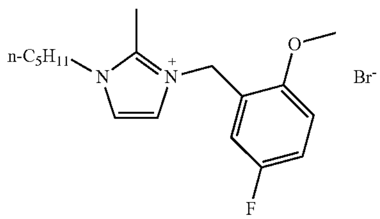 | 1H NMR (600 MHz, Chloroform-d) δ 7.44 (d, J = 2.2 Hz, 1H), 7.30 (d, J = 2.2 Hz, 1H), 7.22 (dd, J = 8.1, 3.1 Hz, 1H), 7.06 (ddd, J = 9.0, 7.9, 3.1 Hz, 1H), 6.86 (dd, J = 9.1, 4.2 Hz, 1H), 5.38 (s, 2H), 4.22-4.18 (m, 2H), 3.81 (s, 3H), 2.86 (s, 3H), 1.89-1.79 (m, 2H), 1.38-1.29 (m, 4H), 0.91-0.86 (m, 3H). MS (ESI) m/z: 291 [M + H]+. |
| IA-21 | 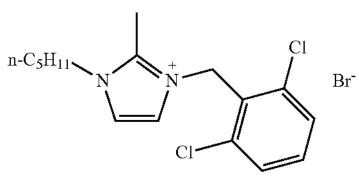 | 1H NMR (600 MHz, Chloroform-d) δ 7.45 (d, J = 8.5 Hz, 2H), 7.39 (d, J = 7.1 Hz, 1H), 7.33 (s, 1H), 6.91 (s, 1H), 5.52 (s, 2H), 4.13 (t, J = 7.3 Hz, 2H), 2.81 (s, 3H), 1.84-1.72 (m, 2H), 1.43-1.18 (m, 4H), 0.88 (t, J = 7.1 Hz, 3H). MS (ESI) m/z: 312 [M + H]+ |
| IA-22 | 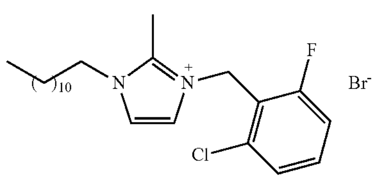 | 1H NMR (600 MHz, Chloroform-d) δ 7.51 (d, J = 2.2 Hz, 1H), 7.44 (td, J = 8.3, 6.1 Hz, 1H), 7.34 (dd, J = 8.2, 1.1 Hz, 1H), 7.22 (d, J = 2.2 Hz, 1H), 7.15 (ddd, J = 9.4, 8.3, 1.1 Hz, 1H), 5.57 (d, J = 1.6 Hz, 2H), 4.36-4.16 (m, 2H), 2.98 (s, 3H), 1.86 (td, J = 8.6, 5.0 Hz, 2H), 1.31-1.21 (m, 18H), 0.89 (t, J = 7.1 Hz, 3H). MS (ESI) m/z: 394 [M + H]+. |
| IA-23 | 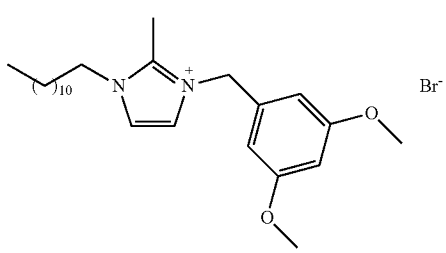 | 1H NMR (600 MHz, Chloroform-d) δ 7.90 (s, 2H), 6.45 (s, 1H), 6.34 (s, 2H), 5.25 (s, 2H), 4.09 (s, 2H), 3.77 (s, 6H), 2.63 (s, 3H), 1.81 (t, J = 7.1 Hz, 2H), 1.34-1.20 (m, 18H), 0.88 (t, J = 6.9 Hz, 3H). MS (ESI) m/z: 402 [M + H]+ |
| IA-24 | 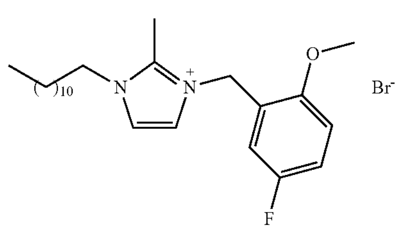 | 1H NMR (600 MHz, DMSO-d6) δ 7.71 (d, J = 2.2 Hz, 1H), 7.60 (d, J = 2.2 Hz, 1H), 7.27-7.16 (m, 2H), 7.12-7.07 (m, 1H), 5.30 (s, 2H), 4.12 (t, J = 7.4 Hz, 2H), 3.80 (s, 3H), 2.66 (s, 3H), 1.73 (t, J = 7.0 Hz, 2H), 1.32-1.18 (m, 18H), 0.85 (d, J = 7.2 Hz, 3H). MS (ESI) m/z: 390 [M + H]+ |

TABLE 1-continued

Structure and characterization of compounds IA-IF

| No. | Structure | 1H NMR and/or MS data |
|---|---|---|
| IA-25 | 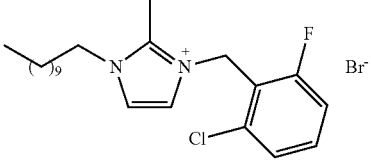 | 1H NMR (600 MHz, DMSO-d6) δ 7.71 (d, J = 1.9 Hz, 1H), 7.60 (d, J = 1.9 Hz, 1H), 7.26-7.16 (m, 2H), 7.13-7.06 (m, 1H), 5.30 (d, J = 1.5 Hz, 2H), 4.14-4.07 (m, 2H), 3.80 (d, J = 1.5 Hz, 3H), 2.66 (d, J = 1.5 Hz, 3H), 1.73 (q, J = 7.3 Hz, 2H), 1.28-1.19 (m, 16H), 0.86 (td, J = 7.0, 1.5 Hz, 3H). MS (ESI) m/z: 380 [M + H]+ |
| IA-26 | 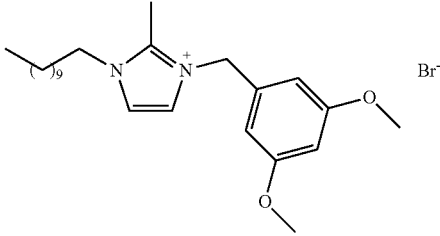 | 1H NMR (600 MHz, Chloroform-d) δ 7.52 (d, J = 2.1 Hz, 1H), 7.42 (d, J = 2.1 Hz, 1H), 6.51 (d, J = 2.2 Hz, 2H), 6.42 (t, J = 2.2 Hz, 1H), 5.46 (s, 2H), 4.16 (t, 2H), 3.78 (s, 6H), 2.81 (s, 3H), 1.87-1.80 (m, 2H), 1.28-1.23 (m, 16H), 0.87 (t, J = 7.1 Hz, 3H). MS (ESI) m/z: 388 [M + H]+ |
| IA-27 | 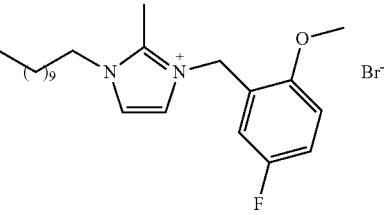 | 1H NMR (600 MHz, DMSO-d6) δ 7.71 (d, J = 2.2 Hz, 1H), 7.60 (d, J = 2.1 Hz, 1H), 7.27-7.18 (m, 2H), 7.10 (dd, J = 9.0, 4.4 Hz, 1H), 5.30 (s, 2H), 4.12 (t, J = 7.3 Hz, 2H), 3.80 (s, 3H), 2.51 (t, J = 1.9 Hz, 3H), 1.77-1.64 (m, 2H), 1.28-1.20 (m, 16H), 0.85 (t, 3H). MS (ESI) m/z: 376 [M + H]+ |
| IA-28 | 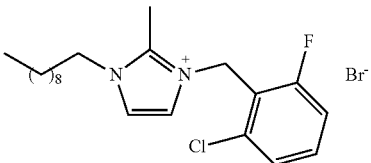 | 1H NMR (600 MHz, DMSO-d6) δ 7.73 (d, J = 2.2 Hz, 1H), 7.57 (td, J = 8.3, 6.1 Hz, 1H), 7.50-7.46 (m, 2H), 7.39 (ddd, J = 9.6, 8.3, 1.1 Hz, 1H), 5.53 (d, J = 1.2 Hz, 2H), 4.13 (t, J = 7.3 Hz, 2H), 2.70 (s, 3H), 1.72 (t, J = 7.3 Hz, 2H), 1.30-1.20 (m, 14H), 0.86 (t, J = 7.0 Hz, 3H). MS (ESI) m/z: 366 [M + H]+ |
| IA-29 | 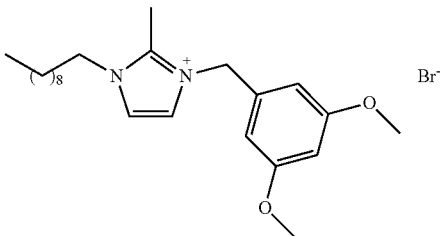 | 1H NMR (600 MHz, DMSO-d6) δ 7.78 (d, J = 2.1 Hz, 1H), 7.76 (d, J = 2.1 Hz, 1H), 6.51 (t, J = 2.3 Hz, 1H), 6.47 (d, J = 2.2 Hz, 2H), 5.33 (s, 2H), 4.12 (t, J = 7.4 Hz, 2H), 3.74 (s, 6H), 2.64 (s, 3H), 1.73 (p, J = 7.6 Hz, 2H), 1.31-1.15 (m, 14H), 0.85 (d, J = 7.1 Hz, 3H). MS (ESI) m/z: 374 [M + H]+ |
| IA-30 | 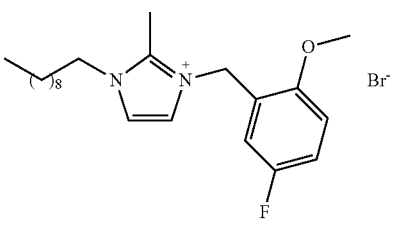 | 1H NMR (600 MHz, Chloroform-d) δ 7.26 (d, J = 2.1 Hz, 1H), 7.23 (d, J = 2.0 Hz, 1H), 7.12-7.05 (m, 2H), 6.88 (dd, J = 8.9, 4.2 Hz, 1H), 5.24 (s, 2H), 4.09 (t, J = 7.6 Hz, 2H), 3.81 (s, 3H), 2.72 (s, 3H), 1.80 (t, J = 7.1 Hz, 2H), 1.34-1.23 (m, 14H), 0.88 (t, J = 7.0 Hz, 3H). MS (ESI) m/z: 362 [M + H]+ |
| IA-31 | 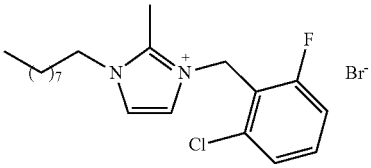 | 1H NMR (600 MHz, Chloroform-d) δ 7.58 (d, J = 2.2 Hz, 1H), 7.42 (dd, J = 8.3, 6.1 Hz, 1H), 7.32 (dt, J = 8.2, 1.1 Hz, 1H), 7.21 (d, J = 2.3 Hz, 1H), 7.13 (ddd, J = 9.4, 8.4, 1.1 Hz, 1H), 5.56 (d, J = 1.6 Hz, 2H), 4.29-4.19 (m, 2H), 2.96 (s, 3H), 1.90-1.75 (m, 2H), 1.29-1.14 (m, 12H), 0.86 (t, J = 7.1 Hz, 3H). MS (ESI) m/z: 352 [M + H]+ |

TABLE 1-continued

Structure and characterization of compounds IA-IF

| No. | Structure | 1H NMR and/or MS data |
|---|---|---|
| IA-32 | 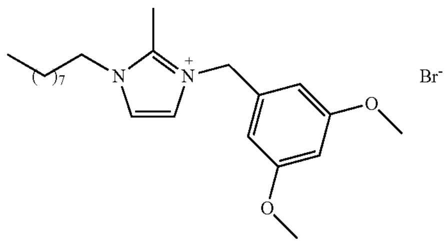 | 1H NMR (600 MHz, DMSO-d6) δ 7.78 (d, J = 2.1 Hz, 1H), 7.76 (d, J = 2.2 Hz, 1H), 6.51 (t, J = 2.2 Hz, 1H), 6.47 (d, J = 2.3 Hz, 2H), 5.33 (s, 2H), 4.12 (t, J = 7.4 Hz, 2H), 3.74 (s, 6H), 2.63 (s, 3H), 1.83-1.61 (m, 2H), 1.28-1.15 (m, 12H), 0.86 (t, J = 7.0 Hz, 3H). MS (ESI) m/z: 360 [M + H]+ |
| IA-33 | 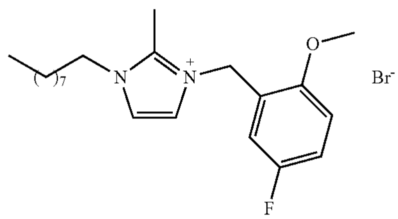 | 1H NMR (600 MHz, Chloroform-d) δ 7.47 (d, J = 2.2 Hz, 1H), 7.34 (d, J = 2.2 Hz, 1H), 7.27 (dd, J = 8.2, 3.1 Hz, 1H), 7.08-7.04 (m, 1H), 6.86 (dd, J = 9.1, 4.2 Hz, 1H), 5.40 (s, 2H), 4.21 (t, 2H), 3.81 (s, 3H), 2.86 (s, 3H), 1.86-1.75 (m, 2H), 1.35-1.17 (m, 12H), 0.85 (t, J = 7.0 Hz, 3H). MS (ESI) m/z: 348 [M + H]+ |
| IA-34 | 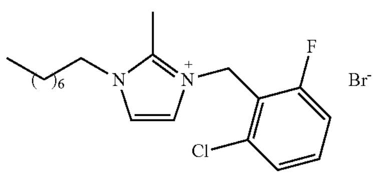 | 1H NMR (600 MHz, Chloroform-d) δ 7.59 (d, J = 2.2 Hz, 1H), 7.42 (td, J = 8.3, 6.1 Hz, 1H), 7.32-7.28 (m, 1H), 7.21 (d, J = 2.2 Hz, 1H), 7.13 (ddd, J = 9.4, 8.4, 1.1 Hz, 1H), 5.55 (d, J = 1.5 Hz, 2H), 4.40-4.17 (m, 2H), 2.95 (s, 3H), 1.86-1.80 (m, 2H), 1.27-1.16 (m, 10H), 0.85 (t, J = 7.1 Hz, 3H). MS (ESI) m/z: 338 [M + H]+ |
| IA-35 | 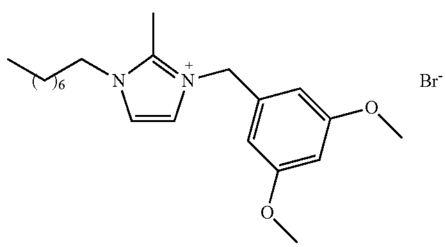 | 1H NMR (600 MHz, Chloroform-d) δ 7.52 (s, 1H), 7.43 (d, J = 2.1 Hz, 1H), 6.50 (s, 2H), 6.41 (d, J = 2.7 Hz, 1H), 5.45 (s, 2H), 4.16 (d, J = 7.2 Hz, 2H), 3.78 (q, J = 3.4, 2.7 Hz, 6H), 2.81-2.79 (m, 3H), 1.82 (q, J = 7.1 Hz, 2H), 1.32-1.18 (m, 10H), 0.86 (dq, J = 11.2, 4.0 Hz, 3H). MS (ESI) m/z: 346 [M + H]+ |
| IA-36 | 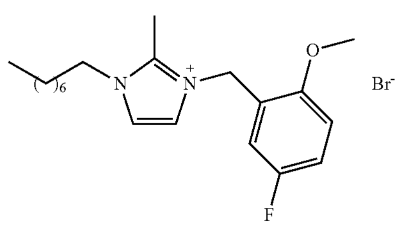 | 1H NMR (600 MHz, Chloroform-d) δ 7.49-7.46 (m, 1H), 7.34 (d, J = 2.1 Hz, 1H), 7.29-7.25 (m, 1H), 7.04 (ddd, J = 9.1, 7.9, 3.1 Hz, 1H), 6.85 (dd, J = 9.0, 4.3 Hz, 1H), 5.39 (s, 2H), 4.20 (t, J = 7.5 Hz, 2H), 3.80 (s, 3H), 2.85 (s, 3H), 1.81 (p, J = 7.5 Hz, 2H), 1.29-1.15 (m, 10H), 0.83 (t, J = 7.0 Hz, 3H). MS (ESI) m/z: 334 [M + H]+ |
| IA-37 | 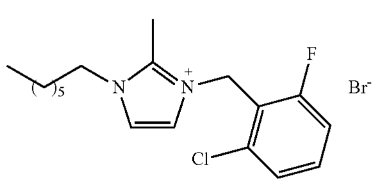 | 1H NMR (600 MHz, DMSO-d6) δ 7.72 (d, J = 2.3 Hz, 1H), 7.58 (td, J = 8.3, 6.2 Hz, 1H), 7.50-7.48 (m, 2H), 7.40 (ddd, J = 9.6, 8.3, 1.1 Hz, 1H), 5.52 (d, J = 1.2 Hz, 2H), 4.13 (t, J = 7.3 Hz, 2H), 2.69 (s, 3H), 1.72 (p, J = 7.4 Hz, 2H), 1.32-1.19 (m, 8H), 0.86 (t, J = 6.9 Hz, 3H). MS (ESI) m/z: 324 [M + H]+ |
| IA-38 | 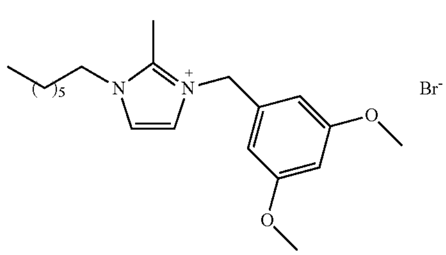 | 1H NMR (600 MHz, DMSO-d6) δ 7.76 (d, J = 2.1 Hz, 1H), 7.75 (d, J = 2.1 Hz, 1H), 6.51 (t, J = 2.3 Hz, 1H), 6.46 (d, J = 2.3 Hz, 2H), 5.32 (s, 2H), 4.12 (t, J = 7.4 Hz, 2H), 3.74 (s, 6H), 2.63 (s, 3H), 1.74 (p, J = 7.4 Hz, 2H), 1.30-1.22 (m, 8H), 0.86 (t, J = 6.9 Hz, 3H). MS (ESI) m/z: 332 [M + H]+ |

TABLE 1-continued

Structure and characterization of compounds IA-IF

| No. | Structure | 1H NMR and/or MS data |
|---|---|---|
| IA-39 | 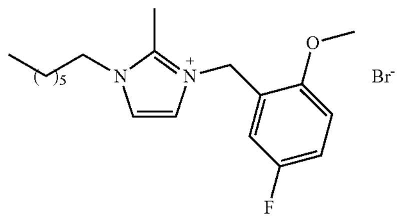 | 1H NMR (600 MHz, DMSO-d6) δ 7.71 (d, J = 2.1 Hz, 1H), 7.60 (d, J = 2.2 Hz, 1H), 7.26-7.21 (m, 1H), 7.20 (dd, J = 8.9, 3.1 Hz, 1H), 7.10 (dd, J = 9.1, 4.4 Hz, 1H), 5.30 (s, 2H), 4.12 (t, J = 7.3 Hz, 2H), 3.80 (s, 3H), 2.66 (s, 3H), 1.77-1.70 (m, 2H), 1.30-1.23 (m, 8H), 0.86 (t, J = 6.9 Hz, 3H). MS (ESI) m/z: 320 [M + H]+ |
| IA-40 | 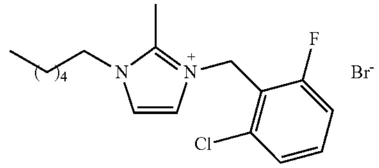 | 1H NMR (600 MHz, DMSO-d6) δ 7.73 (d, J = 2.2 Hz, 1H), 7.57 (td, J = 8.3, 6.2 Hz, 1H), 7.49 (td, J = 3.5, 3.1, 1.1 Hz, 2H), 7.39 (ddd, J = 9.7, 8.4, 1.1 Hz, 1H), 5.53 (d, J = 1.2 Hz, 2H), 4.14 (t, J = 7.3 Hz, 2H), 2.69 (s, 3H), 1.80-1.65 (m, 2H), 1.26 (s, 6H), 0.86 (t, 3H). MS (ESI) m/z: 310 [M + H]+ |
| IA-41 | 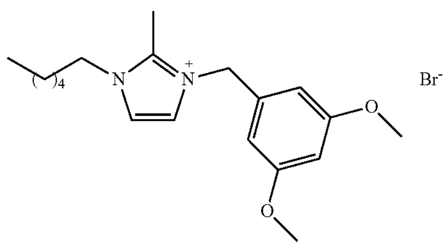 | 1H NMR (600 MHz, Chloroform-d) δ 7.27 (s, 1H), 7.24 (s, 1H), 6.47 (t, J = 2.1 Hz, 1H), 6.35 (d, J = 2.2 Hz, 2H), 5.28 (s, 2H), 4.11 (t, J = 7.6 Hz, 2H), 3.80 (s, 6H), 2.66 (s, 3H), 1.84 (t, J = 7.3 Hz, 2H), 1.38-1.28 (m, 6H), 0.91 (td, J = 6.9, 5.8, 3.0 Hz, 3H). MS (ESI) m/z: 318 [M + H]+ |
| IA-42 | 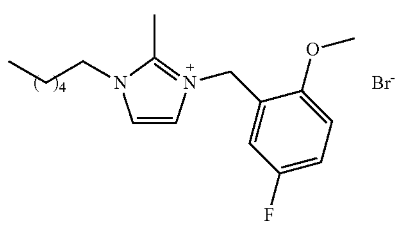 | 1H NMR (600 MHz, DMSO-d6) δ 7.71 (d, J = 2.1 Hz, 1H), 7.60 (d, J = 2.2 Hz, 1H), 7.24 (td, J = 8.7, 3.2 Hz, 1H), 7.20 (dd, J = 8.9, 3.2 Hz, 1H), 7.10 (dd, J = 9.0, 4.4 Hz, 1H), 5.30 (s, 2H), 4.12 (t, J = 7.4 Hz, 2H), 3.80 (s, 3H), 2.67 (s, 3H), 1.73 (p, J = 7.4 Hz, 2H), 1.31-1.20 (m, 6H), 0.89-0.84 (m, 3H). MS (ESI) m/z: 306 [M + H]+ |
| IA-43 | 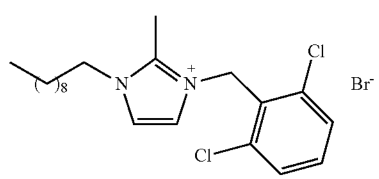 | 1H NMR (600 MHz, Chloroform-d) δ 7.60 (d, J = 2.3 Hz, 1H), 7.45 (d, J = 1.9 Hz, 1H), 7.44 (s, 1H), 7.40 (dd, J = 9.3, 6.7 Hz, 1H), 6.95 (d, J = 2.2 Hz, 1H), 5.64 (s, 2H), 4.29 (t, J = 7.5 Hz, 2H), 3.02 (s, 3H), 1.88-1.82 (m, 2H), 1.31-1.20 (m, 14H), 0.86 (t, J = 7.0 Hz, 3H). MS (ESI) m/z: 383 [M + H]+ |
| IA-44 | 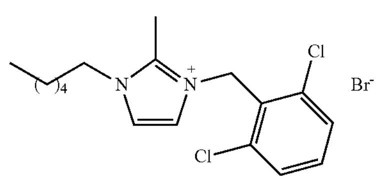 | 1H NMR (600 MHz, Chloroform-d) δ 7.61 (d, J = 2.2 Hz, 1H), 7.46-7.43 (m, 2H), 7.40 (dd, J = 9.3, 6.6 Hz, 1H), 6.95 (d, J = 2.2 Hz, 1H), 5.63 (s, 2H), 4.28 (t, J = 7.5 Hz, 2H), 3.01 (s, 3H), 1.85 (p, J = 7.5 Hz, 2H), 1.31-1.23 (m, 6H), 0.87-0.84 (m, 3H). MS (ESI) m/z: 327 [M + H]+ |
| IA-45 | 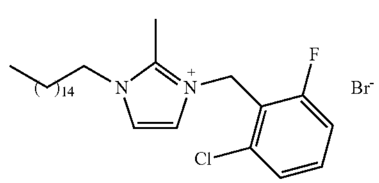 | 1H NMR (600 MHz, Chloroform-d) δ 7.60 (d, J = 2.2 Hz, 1H), 7.42 (td, J = 8.3, 6.1 Hz, 1H), 7.31 (d, J = 8.1 Hz, 1H), 7.21 (d, J = 2.1 Hz, 1H), 7.13 (t, J = 8.8 Hz, 1H), 5.56 (d, J = 1.4 Hz, 2H), 4.25 (t, J = 7.6 Hz, 2H), 2.95 (s, 3H), 1.83 (t, J = 7.5 Hz, 2H), 1.36-1.19 (m, 26H), 0.86 (t, J = 7.0 Hz, 3H). MS (ESI) m/z: 451 [M + H]+. |

TABLE 1-continued

Structure and characterization of compounds IA-IF

| No. | Structure | 1H NMR and/or MS data |
|---|---|---|
| IA-46 | 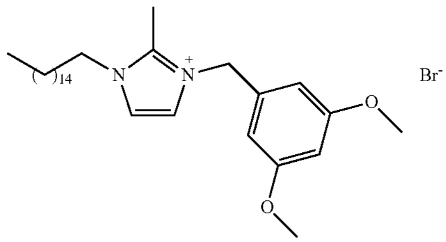 | 1H NMR (600 MHz, Chloroform-d) δ 7.38 (d, J = 2.1 Hz, 1H), 7.28 (d, J = 2.1 Hz, 1H), 6.43 (d, J = 2.3 Hz, 2H), 6.37 (t, J = 2.3 Hz, 1H), 5.38 (s, 2H), 4.08 (t, J = 7.6 Hz, 2H), 3.73 (s, 6H), 2.75 (s, 3H), 1.78 (t, J = 7.4 Hz, 2H), 1.18 (m, 26H), 0.81 (t, J = 6.9 Hz, 3H). MS (ESI) m/z: 458 [M + H]+. |
| IA-47 | 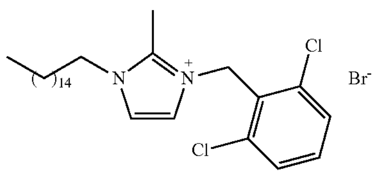 | 1H NMR (600 MHz, Chloroform-d) δ 7.50 (d, J = 2.3 Hz, 1H), 7.49-7.45 (m, 2H), 7.41 (dd, J = 9.0, 7.1 Hz, 1H), 6.97 (d, J = 2.2 Hz, 1H), 5.65 (s, 2H), 4.30 (t, J = 7.5 Hz, 2H), 3.04 (s, 3H), 1.88 (p, J = 7.4 Hz, 2H), 1.40-1.20 (m, 26H), 0.89 (t, J = 7.0 Hz, 3H). MS (ESI) m/z: 467 [M + H]+. |
| IA-48 | 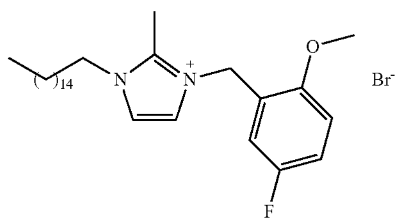 | 1H NMR (600 MHz, Chloroform-d) δ 7.36 (d, J = 2.0 Hz, 1H), 7.28 (t, J = 2.1 Hz, 3H), 7.20 (dt, J = 8.1, 2.1 Hz, 1H), 7.11 (td, J = 8.8, 8.3, 2.6 Hz, 1H), 6.89 (dd, J = 9.1, 4.1 Hz, 1H), 5.40 (s, 2H), 4.21 (t, J = 7.6 Hz, 2H), 3.85 (d, J = 1.5 Hz, 3H), 2.90 (d, J = 1.5 Hz, 3H), 1.87 (p, J = 7.5 Hz, 2H), 1.36-1.21 (m, 26H), 0.96-0.85 (m, 3H). MS (ESI) m/z: 446 [M + H]+. |
| IA-49 | 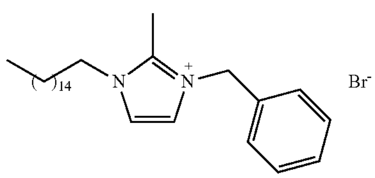 | 1H NMR (600 MHz, Chloroform-d) δ 7.47-7.40 (m, 3H), 7.28-7.21 (m, 4H), 5.34 (s, 2H), 4.11 (t, J = 7.5 Hz, 2H), 2.66 (s, 3H), 1.83 (t, J = 7.2 Hz, 2H), 1.40-1.20 (m, 26H), 0.90 (t, J = 7.0 Hz, 3H). MS (ESI) m/z: 398[M + H]+. |
| IA-50 | 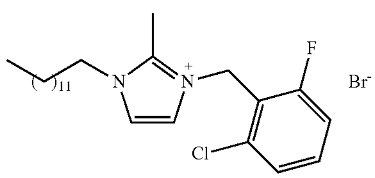 | 1H NMR (600 MHz, DMSO-d6) δ 7.72 (d, J = 2.2 Hz, 1H), 7.58 (td, J = 8.3, 6.2 Hz, 1H), 7.50-7.47 (m, 2H), 7.41-7.37 (m, 1H), 5.52 (s, 2H), 4.13 (t, J = 7.3 Hz, 2H), 2.69 (s, 3H), 1.75-1.69 (m, 2H), 1.26-1.23 (m, 20H), 0.86 (t, J = 7.0 Hz, 3H). MS(ESI) m/z: 409[M + H]+. |
| IA-51 | 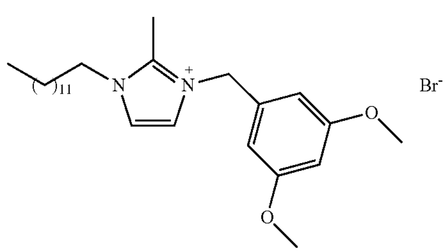 | 1H NMR (600 MHz, DMSO-d6) δ 7.77 (d, J = 2.1 Hz, 1H), 7.75 (d, J = 2.1 Hz, 1H), 6.50 (t, J = 2.2 Hz, 1H), 6.47 (d, J = 2.2 Hz, 2H), 5.33 (s, 2H), 4.12 (t, J = 7.4 Hz, 2H), 3.74 (s, 6H), 2.63 (s, 3H), 1.75-1.70 (m, 2H), 1.25-1.23 (m, 20H), 0.85 (t, J = 7.0 Hz, 3H). MS(ESI) m/z: 416[M + H]+. |
| IA-52 | 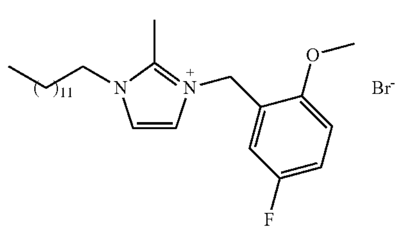 | 1H NMR (600 MHz, DMSO-d6) δ 7.70 (d, J = 2.2 Hz, 1H), 7.60 (d, J = 2.1 Hz, 1H), 7.23 (td, J = 8.7, 3.2 Hz, 1H), 7.19 (dd, J = 8.9, 3.1 Hz, 1H), 7.10 (dd, J = 9.0, 4.4 Hz, 1H), 5.30 (s, 2H), 4.12 (t, J = 7.4 Hz, 2H), 3.80 (s, 3H), 2.66 (s, 3H), 1.76-1.70 (m, 2H), 1.26-1.23 (m, 20H), 0.86 (t, J = 7.0 Hz, 3H). MS(ESI) m/z: 404[M + H]+. |

TABLE 1-continued

Structure and characterization of compounds IA-IF

| No. | Structure | 1H NMR and/or MS data |
|---|---|---|
| IA-53 | 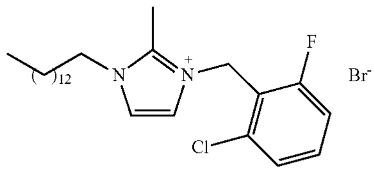 | 1H NMR (600 MHz, DMSO-d6) δ 7.73 (d, J = 2.2 Hz, 1H), 7.58 (td, J = 8.3, 6.2 Hz, 1H), 7.50-7.48 (m, 2H), 7.39 (ddd, J = 9.6, 8.4, 1.0 Hz, 1H), 5.52 (s, 2H), 4.13 (t, J = 7.3 Hz, 2H), 2.70 (s, 3H), 1.74-1.69 (m, 2H), 1.28-1.23 (m, 22H), 0.86 (t, J = 7.0 Hz, 3H). MS(ESI) m/z: 423[M + H]+. |
| IA-54 | 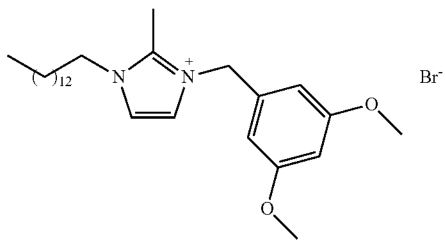 | 1H NMR (600 MHz, DMSO-d6) δ 7.77 (d, J = 2.1 Hz, 1H), 7.75 (d, J = 2.1 Hz, 1H), 6.51 (t, J = 2.2 Hz, 1H), 6.47 (d, J = 2.2 Hz, 2H), 5.33 (s, 2H), 4.12 (t, J = 7.4 Hz, 2H), 3.74 (s, 6H), 2.63 (s, 3H), 1.76-1.69 (m, 2H), 1.26-1.23 (m, 22H), 0.86 (t, J = 7.0 Hz, 3H). MS(ESI) m/z: 430[M + H]+. |
| IA-55 | 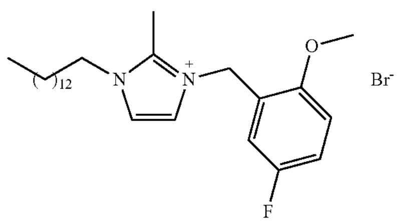 | 1H NMR (600 MHz, DMSO-d6) δ 7.71 (d, J = 2.2 Hz, 1H), 7.60 (d, J = 2.2 Hz, 1H), 7.24 (td, J = 8.7, 3.2 Hz, 1H), 7.19 (dd, J = 8.9, 3.1 Hz, 1H), 7.10 (dd, J = 9.1, 4.4 Hz, 1H), 5.30 (s, 2H), 4.12 (t, J = 7.4 Hz, 2H), 3.80 (s, 3H), 2.66 (s, 3H), 1.76-1.69 (m, 2H), 1.26-1.22 (m, 22H), 0.86 (t, J = 7.0 Hz, 3H). MS(ESI) m/z: 418[M + H]+. |
| IA-56 | 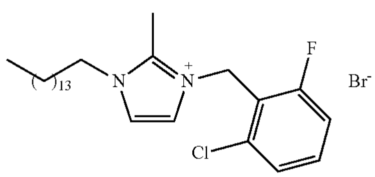 | 1H NMR (600 MHz, DMSO-d6) δ 7.72 (d, J = 2.2 Hz, 1H), 7.60-7.56 (m, 1H), 7.48 (d, J = 8.0 Hz, 2H), 7.39 (t, J = 9.1 Hz, 1H), 5.52 (s, 2H), 4.13 (t, J = 7.3 Hz, 2H), 2.70 (s, 3H), 1.72 (s, 2H), 1.26-1.22 (m, 24H), 0.86 (t, J = 7.0 Hz, 3H). MS(ESI) m/z: 437[M + H]+. |
| IA-57 | 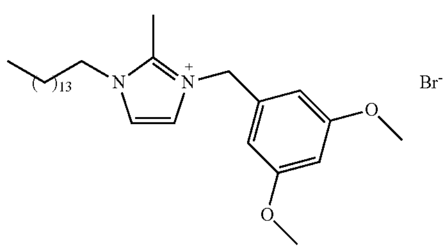 | 1H NMR (600 MHz, DMSO-d6) δ 7.76 (m, 1H), 7.75 (m, 1H), 6.51 (s, 1H), 6.47 (s, 2H), 5.33 (s, 2H), 4.12 (t, J = 7.4 Hz, 2H), 3.74 (s, 6H), 2.63 (s, 3H), 1.73 (s, 2H), 1.25-1.22 (m, 24H), 0.86 (t, J = 7.0 Hz, 3H). MS(ESI) m/z: 444[M + H]+. |
| IA-58 | 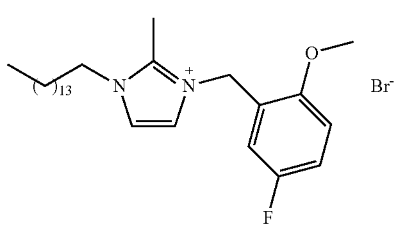 | 1H NMR (600 MHz, DMSO-d6) δ 7.71 (d, J = 2.1 Hz, 1H), 7.60 (d, J = 2.1 Hz, 1H), 7.23 (dd, J = 10.2, 7.3 Hz, 1H), 7.20 (d, J = 9.1 Hz, 1H), 7.10 (dd, J = 9.2, 4.4 Hz, 1H), 5.30 (s, 2H), 4.12 (t, J = 7.4 Hz, 2H), 3.80 (s, 3H), 2.66 (s, 3H), 1.73 (m, 2H), 1.26-1.22 (m, 24H), 0.86 (t, J = 7.0 Hz, 3H). MS(ESI) m/z: 432[M + H]+. |
| IA-59 | 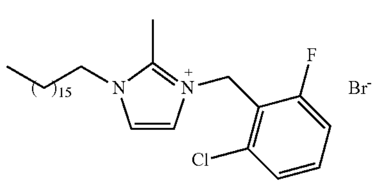 | 1H NMR (600 MHz, DMSO-d6) δ 7.72 (d, J = 2.2 Hz, 1H), 7.58 (td, J = 8.3, 6.2 Hz, 1H), 7.50-7.47 (m, 2H), 7.41-7.38 (m, 1H), 5.52 (s, 2H), 4.13 (t, J = 7.3 Hz, 2H), 2.70 (s, 3H), 1.75-1.69 (m, 2H), 1.25-1.22 (m, 28H), 0.86 (t, J = 7.0 Hz, 3H). MS(ESI) m/z: 465[M + H]+. |

TABLE 1-continued

Structure and characterization of compounds IA-IF

| No. | Structure | 1H NMR and/or MS data |
|---|---|---|
| IA-60 | 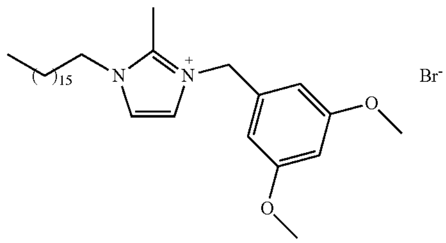 | 1H NMR (600 MHz, DMSO-d6) δ 7.76 (s, 1H), 7.75 (s, 1H), 6.51 (s, 1H), 6.46 (d, J = 2.3 Hz, 2H), 5.32 (s, 2H), 4.11 (t, J = 7.4 Hz, 2H), 3.74 (s, 6H), 2.63 (s, 3H), 1.73 (s, 2H), 1.25-1.22 (m, 28H), 0.86 (t, J = 7.0 Hz, 3H). MS(ESI) m/z: 472[M + H]+. |
| IA-61 | 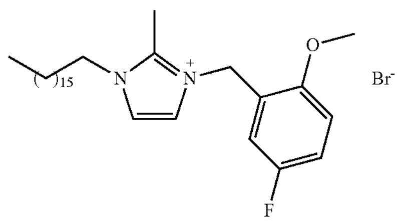 | 1H NMR (600 MHz, DMSO-d6) δ 7.70 (d, J = 2.1 Hz, 1H), 7.59 (d, J = 2.2 Hz, 1H), 7.22 (d, J = 8.8 Hz, 1H), 7.19 (d, J = 8.7 Hz, 1H), 7.10 (dd, J = 8.9, 4.3 Hz, 1H), 5.29 (s, 2H), 4.11 (t, J = 7.3 Hz, 2H), 3.80 (s, 3H), 2.66 (s, 3H), 1.73 (m, 2H), 1.25-1.22 (m, 28H), 0.86 (t, J = 7.0 Hz, 3H). MS(ESI) m/z: 460[M + H]+. |
| IA-62 | 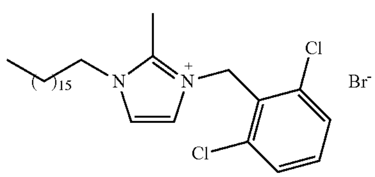 | 1H NMR (600 MHz, DMSO-d6) δ 7.71 (d, J = 2.2 Hz, 1H), 7.65 (s, 1H), 7.64 (s, 1H), 7.56 (dd, J = 8.7, 7.5 Hz, 1H), 7.22 (d, J = 2.2 Hz, 1H), 5.57 (s, 2H), 4.15 (t, J = 7.2 Hz, 2H), 2.75 (s, 3H), 1.75-1.69 (m, 2H), 1.27-1.22 (m, 28H), 0.85 (t, J = 7.0 Hz, 3H). MS(ESI) m/z: 481[M + H]+. |
| IA-63 | 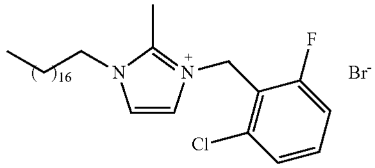 | 1H NMR (600 MHz, DMSO-d6) δ 7.74 (d, J = 2.2 Hz, 1H), 7.58 (td, J = 8.3, 6.2 Hz, 1H), 7.48 (dd, J = 5.1, 3.0 Hz, 2H), 7.41-7.37 (m, 1H), 5.53 (s, 2H), 4.14 (t, J = 7.3 Hz, 2H), 2.70 (s, 3H), 1.74-1.69 (m, 2H), 1.26-1.23 (m, 30H), 0.86 (t, J = 7.0 Hz, 3H). MS(ESI) m/z: 479[M + H]+. |
| IA-64 | 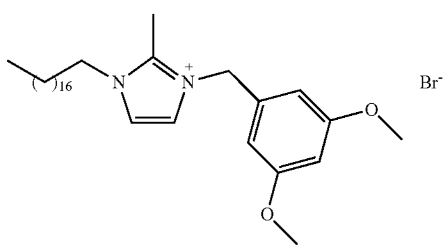 | 1H NMR (600 MHz, DMSO-d6) δ 7.76 (d, J = 2.1 Hz, 1H), 7.74 (d, J = 2.1 Hz, 1H), 6.51 (t, J = 2.2 Hz, 1H), 6.46 (d, J = 2.2 Hz, 2H), 5.32 (s, 2H), 4.11 (t, J = 7.3 Hz, 2H), 3.74 (s, 6H), 2.62 (s, 3H), 1.73 (dd, J = 14.3, 7.1 Hz, 2H), 1.25-1.23 (m, 30H), 0.86 (t, J = 7.0 Hz, 3H). MS(ESI) m/z: 486[M + H]+. |
| IA-65 | 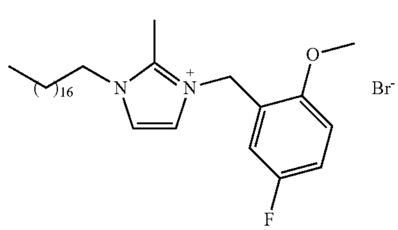 | 1H NMR (600 MHz, DMSO-d6) δ 7.72 (d, J = 2.1 Hz, 1H), 7.61 (d, J = 2.1 Hz, 1H), 7.24 (dt, J = 8.7, 4.3 Hz, 1H), 7.22-7.19 (m, 1H), 7.10 (dd, J = 9.0, 4.4 Hz, 1H), 5.31 (s, 2H), 4.12 (t, J = 7.4 Hz, 2H), 3.80 (s, 3H), 2.66 (s, 3H), 1.73 (dd, J = 14.4, 7.3 Hz, 2H), 1.25-1.22 (m, 30H), 0.86 (t, J = 7.0 Hz, 3H). MS(ESI) m/z: 474[M + H]+. |
| IA-66 | 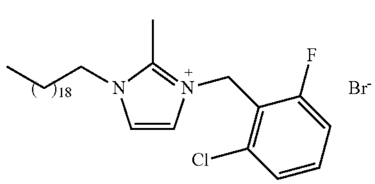 | 1H NMR (600 MHz, DMSO-d6) δ 7.68 (d, J = 2.2 Hz, 1H), 7.56 (td, J = 8.3, 6.2 Hz, 1H), 7.46 (d, J = 8.1 Hz, 1H), 7.44 (d, J = 2.1 Hz, 1H), 7.37 (ddd, J = 9.6, 8.5, 1.0 Hz, 1H), 5.50 (s, 2H), 4.12 (t, J = 7.3 Hz, 2H), 2.68 (s, 3H), 1.71 (dd, J = 14.3, 7.3 Hz, 2H), 1.23-1.20 (m, 34H), 0.83 (t, J = 7.0 Hz, 3H). MS(ESI) m/z: 507[M + H]+. |

TABLE 1-continued

Structure and characterization of compounds IA-IF

| No. | Structure | 1H NMR and/or MS data |
|---|---|---|
| IA-67 | 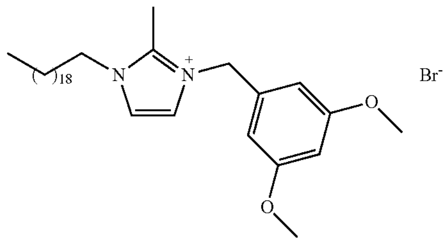 | 1H NMR (600 MHz, DMSO-d6) δ 7.72 (d, J = 2.1 Hz, 1H), 7.71 (d, J = 2.1 Hz, 1H), 6.49 (t, J = 2.2 Hz, 1H), 6.44 (d, J = 2.2 Hz, 2H), 5.31 (s, 2H), 4.10 (t, J = 7.3 Hz, 2H), 3.72 (s, 6H), 2.60 (s, 3H), 1.72 (dd, J = 14.3, 7.2 Hz, 2H), 1.22-1.20 (m, 34H), 0.83 (t, J = 7.0 Hz, 3H). MS(ESI) m/z: 514[M + H]+. |
| IA-68 | 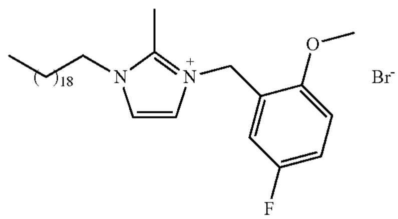 | 1H NMR (600 MHz, DMSO-d6) δ 7.66 (d, J = 2.2 Hz, 1H), 7.56 (d, J = 2.2 Hz, 1H), 7.23-7.20 (m, 1H), 7.18 (dd, J = 8.8, 3.1 Hz, 1H), 7.08 (dd, J = 9.0, 4.4 Hz, 1H), 5.28 (s, 2H), 4.10 (t, J = 7.3 Hz, 2H), 3.78 (s, 3H), 2.64 (s, 3H), 1.71 (dd, J = 14.3, 7.2 Hz, 2H), 1.22-1.20 (m, 34H), 0.83 (t, J = 7.0 Hz, 3H). MS(ESI) m/z: 502[M + H]+. |
| IA-69 | 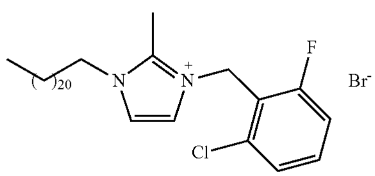 | 1H NMR (600 MHz, DMSO-d6) δ 7.68 (s, 1H), 7.56 (d, J = 5.8 Hz, 1H), 7.47 (d, J = 8.2 Hz, 1H), 7.44 (s, 1H), 7.37 (t, J = 8.8 Hz, 1H), 5.50 (s, 2H), 4.11 (d, J = 6.9 Hz, 2H), 2.68 (s, 3H), 1.67 (d, J = 38.5 Hz, 2H), 1.24-1.20 (m, 38H), 0.83 (t, J = 6.9 Hz, 3H). MS(ESI) m/z: 535[M + H]+. |
| IA-70 | 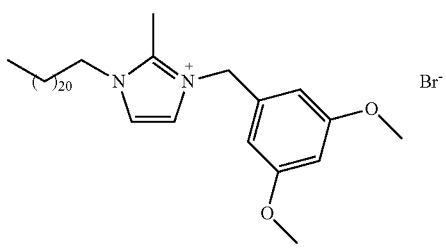 | 1H NMR (600 MHz, DMSO-d6) δ 7.73 (d, J = 2.1 Hz, 1H), 7.71 (d, J = 2.1 Hz, 1H), 6.48 (t, J = 2.2 Hz, 1H), 6.44 (d, J = 2.2 Hz, 2H), 5.31 (s, 2H), 4.10 (t, J = 7.3 Hz, 2H), 3.72 (s, 6H), 2.60 (s, 3H), 1.73-1.69 (m, 2H), 1.22-1.21 (m, 38H), 0.83 (t, J = 7.0 Hz, 3H). MS(ESI) m/z: 542[M + H]+. |
| IA-71 | 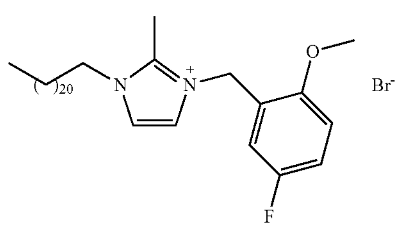 | 1H NMR (600 MHz, DMSO-d6) δ 7.73 (d, J = 2.1 Hz, 1H), 7.71 (d, J = 2.1 Hz, 1H), 6.48 (t, J = 2.2 Hz, 1H), 6.44 (d, J = 2.2 Hz, 2H), 5.31 (s, 2H), 4.10 (t, J = 7.3 Hz, 2H), 3.72 (s, 6H), 2.60 (s, 3H), 1.73-1.69 (m, 2H), 1.22-1.21 (m, 38H), 0.83 (t, J = 7.0 Hz, 3H). MS(ESI) m/z: 530[M + H]+. |
| IA-72 | 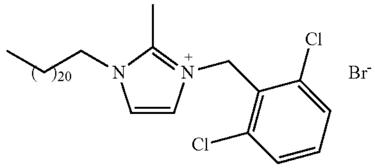 | 1H NMR (600 MHz, DMSO-d6) δ 7.71 (d, J = 2.2 Hz, 1H), 7.65 (s, 1H), 7.64 (s, 1H), 7.56 (dd, J = 8.7, 7.5 Hz, 1H), 7.22 (d, J = 2.2 Hz, 1H), 5.57 (s, 2H), 4.16 (t, J = 7.3 Hz, 2H), 2.76 (s, 3H), 1.75-1.69 (m, 2H), 1.25-1.22 (m, 38H), 0.85 (t, J = 7.0 Hz, 3H). MS(ESI) m/z: 551[M + H]+. |
| IA-73 | 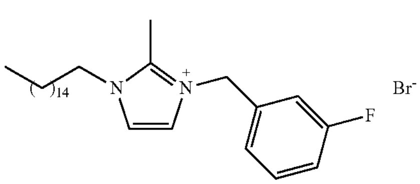 | 1H NMR (600 MHz, Methanol-d4) δ 7.66 (d, J = 2.1 Hz, 1H), 7.59 (d, J = 2.2 Hz, 1H), 7.48 (td, J = 8.0, 5.9 Hz, 1H), 7.22-7.11 (m, 3H), 5.49 (s, 2H), 4.22 (t, J = 7.5 Hz, 2H), 2.70 (s, 3H), 1.88 (t, J = 7.4 Hz, 2H), 1.43-1.26 (m, 26H), 0.92 (t, J = 7.0 Hz, 3H). MS (ESI) m/z: 416 [M + H]+. |

TABLE 1-continued

Structure and characterization of compounds IA-IF

| No. | Structure | 1H NMR and/or MS data |
|---|---|---|
| IA-74 | 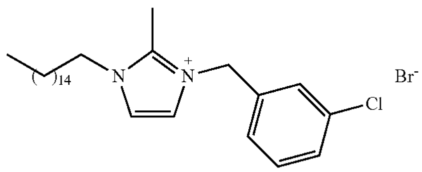 | 1H NMR (600 MHz, Methanol-d4) δ 7.66 (d, J = 2.2 Hz, 1H), 7.60 (d, J = 2.2 Hz, 1H), 7.48-7.40 (m, 3H), 7.31 (dt, J = 7.2, 1.9 Hz, 1H), 5.48 (s, 2H), 4.22 (t, J = 7.5 Hz, 2H), 2.70 (s, 2H), 1.87 (q, J = 7.1 Hz, 2H), 1.46-1.26 (m, 26H), 0.92 (t, J = 7.0 Hz, 3H). MS (ESI) m/z: 433 [M + H]+. |
| IA-75 | 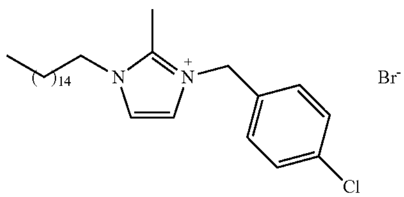 | 1H NMR (600 MHz, Methanol-d4) δ 7.64 (d, J = 2.2 Hz, 1H), 7.57 (d, J = 2.1 Hz, 1H), 7.48-7.45 (m, 2H), 7.39-7.35 (m, 2H), 5.45 (s, 2H), 4.23-4.19 (m, 2H), 2.69 (s, 3H), 1.87 (p, J = 7.3 Hz, 2H), 1.44-1.25 (m, 26H), 0.92 (t, J = 7.0 Hz, 3H). MS (ESI) m/z: 433 [M + H]+. |
| IA-76 | 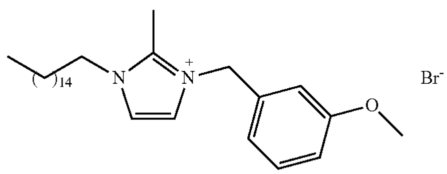 | 1H NMR (600 MHz, Methanol-d4) δ 7.63 (d, J = 2.0 Hz, 1H), 7.57 (d, J = 2.2 Hz, 1H), 7.36 (t, J = 7.9 Hz, 1H), 6.98 (dd, J = 8.3, 2.4 Hz, 1H), 6.93 (t, J = 1.8 Hz, 1H), 6.89 (d, J = 7.6 Hz, 1H), 5.42 (s, 2H), 4.21 (t, J = 7.4 Hz, 2H), 3.82 (s, 3H), 2.69 (s, 3H), 1.87 (t, J = 7.2 Hz, 2H), 1.31 (s, 26H), 0.92 (t, J = 6.9 Hz, 3H). MS (ESI) m/z: 428 [M + H]+ |
| IA-77 | 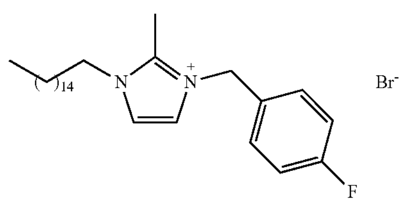 | 1H NMR (600 MHz, Methanol-d4) δ 7.63 (d, J = 2.2 Hz, 1H), 7.55 (d, J = 2.2 Hz, 1H), 7.46-7.42 (m, 2H), 7.22-7.15 (m, 2H), 5.44 (s, 2H), 4.23-4.18 (m, 2H), 2.71 (s, 3H), 1.87 (t, J = 7.4 Hz, 2H), 1.45-1.23 (m, 26H), 0.92 (t, J = 7.0 Hz, 3H). MS (ESI) m/z: 416 [M + H]+ |
| IA-78 | 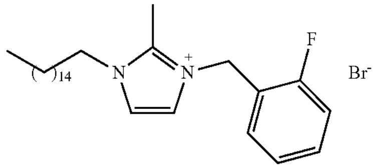 | 1H NMR (600 MHz, Methanol-d4) δ 7.61 (d, J = 2.1 Hz, 1H), 7.53 (d, J = 2.2 Hz, 1H), 7.50 (tdd, J = 7.7, 5.4, 1.7 Hz, 1H), 7.46 (td, J = 7.6, 1.7 Hz, 1H), 7.30 (td, J = 7.5, 1.1 Hz, 1H), 7.24 (ddd, J = 10.5, 8.3, 1.1 Hz, 1H), 5.50 (s, 2H), 4.20 (t, J = 7.4 Hz, 2H), 2.73 (s, 3H), 1.86 (p, J = 7.4 Hz, 2H), 1.44-1.25 (m, 26H), 0.92 (t, J = 7.0 Hz, 3H). MS (ESI) m/z: 416 [M + H]+ |
| IA-79 | 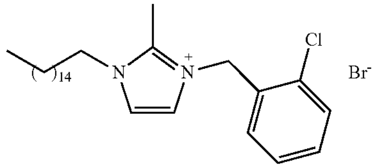 | 1H NMR (600 MHz, Methanol-d4) δ 7.63 (d, J = 2.2 Hz, 1H), 7.56 (dd, J = 7.9, 1.4 Hz, 1H), 7.46 (dtd, J = 24.1, 7.5, 1.5 Hz, 2H), 7.41 (d, J = 2.2 Hz, 1H), 7.34 (dd, J = 7.5, 1.7 Hz, 1H), 5.53 (s, 2H), 4.23 (t, J = 7.4 Hz, 2H), 2.73 (s, 3H), 1.88 (p, J = 7.5 Hz, 2H), 1.45-1.20 (m, 26H), 0.92 (t, J = 7.0 Hz, 3H). MS (ESI) m/z: 433 [M + H]+ |
| IA-80 | 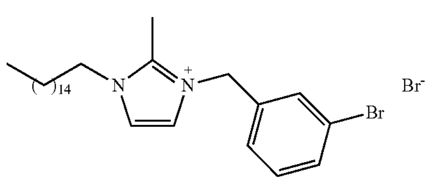 | 1H NMR (600 MHz, Methanol-d4) δ 7.65 (d, J = 2.2 Hz, 1H), 7.59 (dd, J = 5.7, 1.7 Hz, 2H), 7.55 (d, J = 1.9 Hz, 1H), 7.39 (t, J = 7.8 Hz, 1H), 7.35-7.31 (m, 1H), 5.45 (s, 2H), 4.21 (t, J = 7.4 Hz, 2H), 2.69 (s, 3H), 1.88 (t, J = 7.2 Hz, 2H), 1.43-1.25 (m, 26H), 0.92 (t, J = 6.9 Hz, 3H). MS (ESI) m/z: 477 [M + H]+ |
| IA-81 | 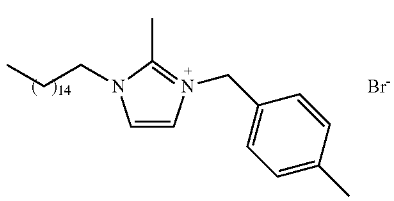 | 1H NMR (600 MHz, Methanol-d4) δ 7.59 (d, J = 2.2 Hz, 1H), 7.50 (d, J = 2.2 Hz, 1H), 7.32 (d, J = 8.6 Hz, 2H), 7.02-6.97 (m, 2H), 5.35 (s, 2H), 4.19 (t, J = 7.4 Hz, 2H), 3.83 (s, 3H), 2.69 (s, 3H), 1.85 (t, J = 7.2 Hz, 2H), 1.31 (s, 26H), 0.92 (t, J = 6.9 Hz, 3H). MS (ESI) m/z: 412 [M + H]+ |

TABLE 1-continued

Structure and characterization of compounds IA-IF

| No. | Structure | 1H NMR and/or MS data |
|---|---|---|
| IA-82 | 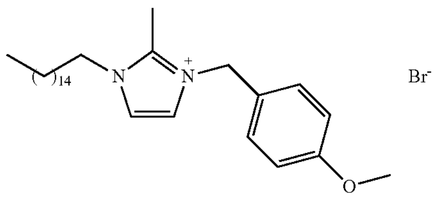 | 1H NMR (600 MHz, Methanol-d4) δ 7.59 (d, J = 2.3 Hz, 1H), 7.50 (d, J = 2.2 Hz, 1H), 7.32 (d, J = 2.1 Hz, 1H), 7.31 (d, J = 2.3 Hz, 1H), 7.00 (s, 1H), 6.99 (s, 1H), 5.35 (s, 2H), 4.22-4.15 (m, 2H), 3.83 (s, 3H), 2.69 (s, 3H), 1.85 (p, J = 7.5 Hz, 2H), 1.43-1.25 (m, 26H), 0.92 (t, J = 7.0 Hz, 3H). MS (ESI) m/z: 428 [M + H]+ |
| IA-83 | 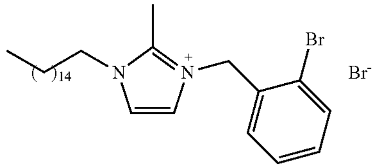 | 1H NMR (600 MHz, Methanol-d4) δ 7.74 (d, J = 8.0 Hz, 1H), 7.64 (d, J = 2.2 Hz, 1H), 7.49 (t, J = 7.6 Hz, 1H), 7.40 (t, J = 7.8 Hz, 1H), 7.37-7.31 (m, 2H), 5.52 (s, 2H), 4.24 (t, J = 7.4 Hz, 2H), 2.75 (d, J = 1.4 Hz, 3H), 1.89 (p, J = 7.2 Hz, 2H), 1.43-1.26 (m, 26H), 0.92 (t, J = 6.9 Hz, 3H). MS (ESI) m/z: 477 [M + H]+ |
| IA-84 | 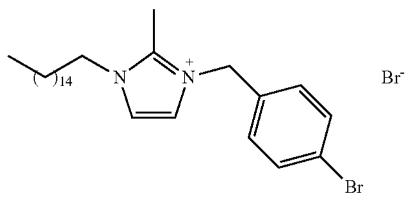 | 1H NMR (600 MHz, Methanol-d4) δ 7.65-7.60 (m, 3H), 7.57 (d, J = 2.1 Hz, 1H), 7.29 (d, J = 8.2 Hz, 2H), 5.42 (s, 2H), 4.20 (t, J = 7.5 Hz, 2H), 2.68 (s, 3H), 1.87 (p, J = 7.3 Hz, 2H), 1.45-1.25 (m, 26H), 0.92 (t, J = 6.9 Hz, 3H). MS (ESI) m/z: 477 [M + H]+ |
| IA-85 | 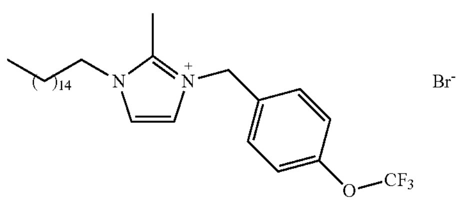 | 1H NMR (600 MHz, Methanol-d4) δ 7.65 (d, J = 2.1 Hz, 1H), 7.59 (d, J = 2.1 Hz, 1H), 7.50 (d, J = 8.4 Hz, 2H), 7.37 (d, J = 8.2 Hz, 2H), 5.50 (s, 2H), 4.21 (t, J = 7.5 Hz, 2H), 2.71 (s, 3H), 1.88 (t, J = 7.4 Hz, 2H), 1.43-1.25 (m, 26H), 0.92 (t, J = 6.9 Hz, 3H). MS (ESI) m/z: 482 [M + H]+ |
| IA-86 | 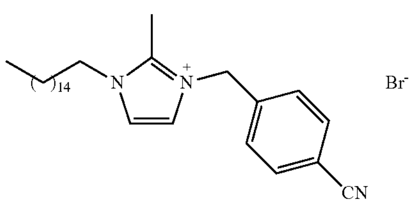 | 1H NMR (600 MHz, Methanol-d4) δ 7.83 (d, J = 8.2 Hz, 2H), 7.70 (d, J = 2.2 Hz, 1H), 7.64 (d, J = 2.2 Hz, 1H), 7.55 (d, J = 8.0 Hz, 2H), 5.60 (s, 2H), 4.24 (t, J = 7.5 Hz, 2H), 2.71 (s, 3H), 1.90 (t, J = 7.5 Hz, 2H), 1.46-1.27 (m, 26H), 0.94 (t, J = 6.9 Hz, 3H). MS (ESI) m/z: 423 [M + H]+ |
| IA-87 | 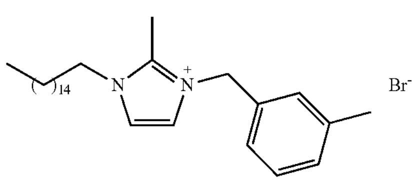 | 1H NMR (600 MHz, Methanol-d4) δ 7.62 (d, J = 2.2 Hz, 1H), 7.55 (d, J = 2.2 Hz, 1H), 7.33 (t, J = 7.6 Hz, 1H), 7.24 (d, J = 7.6 Hz, 1H), 7.17 (s, 1H), 7.12 (d, J = 7.7 Hz, 1H), 5.39 (s, 2H), 4.20 (t, J = 7.4 Hz, 2H), 2.67 (s, 3H), 2.37 (s, 3H), 1.87 (p, J = 7.3 Hz, 2H), 1.41-1.27 (m, 26H), 0.92 (t, J = 7.0 Hz, 3H). MS (ESI) m/z: 412[M + H]+ |
| IA-88 | 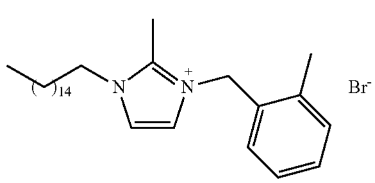 | 1H NMR (600 MHz, Methanol-d4) δ 7.63 (d, J = 2.2 Hz, 1H), 7.35-7.31 (m, 3H), 7.27 (td, J = 7.1, 6.6, 2.3 Hz, 1H), 7.01 (d, J = 7.6 Hz, 1H), 5.46 (s, 2H), 4.28-4.19 (m, 2H), 2.69 (s, 3H), 2.36 (s, 3H), 1.96-1.84 (m, 2H), 1.45-1.26 (m, 26H), 0.92 (t, J = 7.0 Hz, 3H). MS (ESI) m/z: 412 [M + H]+ |
| IA-89 | 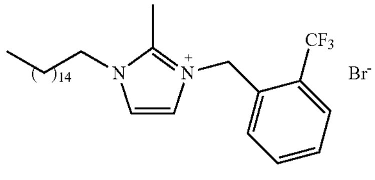 | 1H NMR (600 MHz, Methanol-d4) δ 7.88 (dd, J = 7.8, 1.2 Hz, 1H), 7.75-7.71 (m, 1H), 7.69 (d, J = 2.2 Hz, 1H), 7.65 (t, J = 7.7 Hz, 1H), 7.44 (d, J = 2.2 Hz, 1H), 7.24 (d, J = 7.8 Hz, 1H), 5.66 (s, 2H), 4.29-4.20 (m, 2H), 2.66 (s, 3H), 1.98-1.86 (m, 2H), 1.49-1.24 (m, 26H), 0.92 (t, J = 7.0 Hz, 3H). MS (ESI) m/z: 466 [M + H]+ |

TABLE 1-continued

Structure and characterization of compounds IA-IF

| No. | Structure | 1H NMR and/or MS data |
|---|---|---|
| IA-90 | 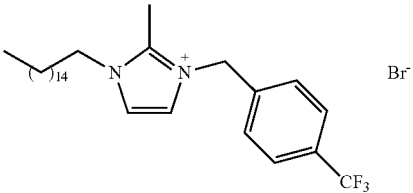 | 1H NMR (600 MHz, Methanol-d4) δ 7.74 (d, J = 8.0 Hz, 2H), 7.65 (d, J = 2.0 Hz, 1H), 7.60 (d, J = 2.1 Hz, 1H), 7.52 (d, J = 8.0 Hz, 2H), 5.55 (s, 2H), 4.19 (t, J = 7.5 Hz, 2H), 2.67 (s, 3H), 1.86 (t, J = 7.3 Hz, 2H), 1.45-1.19 (m, 26H), 0.89 (t, J = 6.9 Hz, 3H). MS (ESI) m/z: 466 [M + H]+ |
| IA-91 | 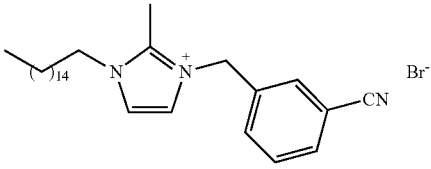 | 1H NMR (600 MHz, Methanol-d4) δ 7.77 (dd, J = 7.5, 1.6 Hz, 1H), 7.75-7.71 (m, 1H), 7.68-7.65 (m, 1H), 7.65-7.60 (m, 2H), 7.58 (d, J = 2.1 Hz, 1H), 5.51 (s, 2H), 4.18 (t, J = 7.5 Hz, 2H), 2.68 (d, J = 1.4 Hz, 3H), 1.86 (t, J = 7.4 Hz, 2H), 1.46-1.22 (m, 26H), 0.90 (t, J = 6.9 Hz, 3H). MS (ESI) m/z: 423 [M + H]+ |
| IA-92 | 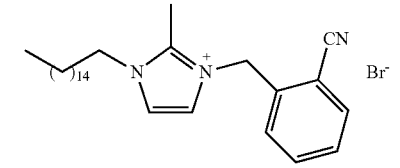 | 1H NMR (600 MHz, Methanol-d4) δ 7.86 (dd, J = 7.7, 1.4 Hz, 1H), 7.77 (td, J = 7.8, 1.4 Hz, 1H), 7.64 (d, J = 2.2 Hz, 1H), 7.62 (td, J = 7.7, 1.2 Hz, 1H), 7.53-7.51 (m, 1H), 7.43 (d, J = 2.2 Hz, 1H), 5.65 (s, 2H), 4.25-4.19 (m, 2H), 2.75 (s, 3H), 1.85 (q, J = 7.4 Hz, 2H), 1.46-1.23 (m, 26H), 0.94-0.87 (m, 3H). MS (ESI) m/z: 423 [M + H]+ |
| IA-93 | 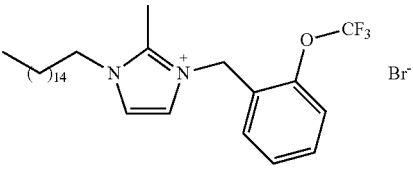 | 1H NMR (600 MHz, Methanol-d4) δ 7.63 (d, J = 2.2 Hz, 1H), 7.56 (ddd, J = 8.7, 6.3, 3.1 Hz, 1H), 7.48-7.40 (m, 4H), 5.51 (s, 2H), 4.20 (t, J = 7.4 Hz, 2H), 2.68 (s, 3H), 1.84 (t, J = 7.4 Hz, 2H), 1.43-1.25 (m, 26H), 0.90 (t, J = 6.8 Hz, 3H). MS (ESI) m/z: 482 [M + H]+ |
| IA-94 | 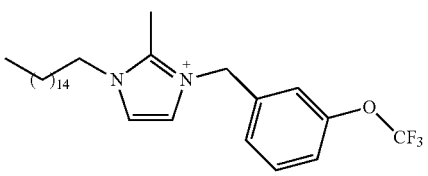 | 1H NMR (600 MHz, Methanol-d4) δ 7.67 (d, J = 2.2 Hz, 1H), 7.61 (d, J = 2.1 Hz, 1H), 7.58 (t, J = 8.0 Hz, 1H), 7.41-7.30 (m, 3H), 5.54 (s, 2H), 4.27-4.18 (m, 2H), 2.71 (s, 3H), 1.88 (p, J = 7.4 Hz, 2H), 1.44-1.23 (m, 26H), 0.92 (t, J = 7.0 Hz, 3H). MS (ESI) m/z: 482 [M + H]+ |
| IA-95 | 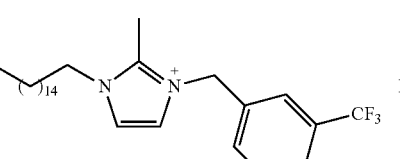 | 1H NMR (600 MHz, Methanol-d4) δ 7.75 (d, J = 7.8 Hz, 1H), 7.71 (s, 1H), 7.70-7.65 (m, 2H), 7.62 (dd, J = 11.2, 4.9 Hz, 2H), 5.57 (d, J = 2.2 Hz, 2H), 4.22 (t, J = 7.5 Hz, 2H), 2.71 (d, J = 2.0 Hz, 3H), 1.88 (t, J = 7.4 Hz, 2H), 1.45-1.26 (m, 26H), 0.92 (t, J = 7.0 Hz, 3H). MS (ESI) m/z: 466 [M + H]+ |
| IA-96 | 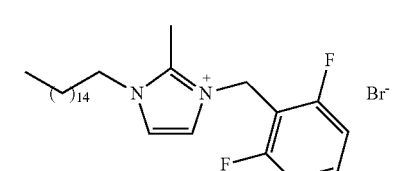 | 1H NMR (600 MHz, Methanol-d4) δ 7.58 (d, J = 2.2 Hz, 1H), 7.57-7.51 (m, 1H), 7.50 (d, J = 2.0 Hz, 1H), 7.13 (t, J = 8.3 Hz, 2H), 5.51 (s, 2H), 4.16 (t, J = 7.5 Hz, 2H), 2.73 (s, 3H), 1.81 (s, 2H), 1.41-1.23 (m, 26H), 0.90 (t, J = 6.9 Hz, 3H). MS (ESI) m/z: 434 [M + H]+ |
| IA-97 | 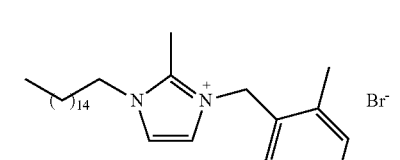 | 1H NMR (600 MHz, Methanol-d4) δ 7.49 (t, J = 1.7 Hz, 1H), 7.27 (t, J = 7.6 Hz, 1H), 7.18 (d, J = 7.6 Hz, 2H), 6.70 (t, J = 1.7 Hz, 1H), 5.39 (s, 2H), 4.20 (t, J = 7.4 Hz, 2H), 2.82 (d, J = 1.3 Hz, 3H), 2.30 (s, 6H), 1.85 (s, 2H), 1.43-1.25 (m, 26H), 0.89 (td, J = 7.0, 1.4 Hz, 3H). MS (ESI) m/z: 426 [M + H]+ |

TABLE 1-continued

Structure and characterization of compounds IA-IF

| No. | Structure | 1H NMR and/or MS data |
|---|---|---|
| IA-98 | 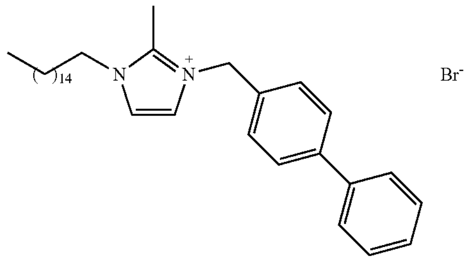 | 1H NMR (600 MHz, Methanol-d4) δ 7.67-7.63 (m, 1H), 7.62 (d, J = 7.9 Hz, 4H), 7.60 (d, J = 2.1 Hz, 1H), 7.50 (t, J = 7.7 Hz, 1H), 7.43 (t, J = 7.6 Hz, 2H), 7.35 (t, J = 7.4 Hz, 1H), 7.31 (dd, J = 7.8, 1.6 Hz, 1H), 5.50 (s, 2H), 4.18 (t, J = 7.4 Hz, 2H), 2.70 (s, 3H), 1.83 (t, J = 7.4 Hz, 2H), 1.39-1.18 (m, 26H), 0.89 (t, J = 6.9 Hz, 3H). MS (ESI) m/z: 474 [M + H]+. |
| IA-99 | 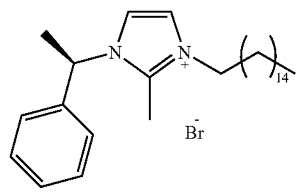 | 1H NMR (600 MHz, Chloroform-d) δ 7.49-7.44 (m, 2H), 7.43-7.38 (m, 2H), 7.38-7.35 (m, 1H), 7.23-7.18 (m, 2H), 5.77 (q, J = 6.9 Hz, 1H), 4.13 (t, J = 7.5 Hz, 2H), 2.62 (s, 3H), 1.92 (d, J = 6.8 Hz, 3H), 1.80 (q, J = 6.9 Hz, 2H), 1.34-1.22 (m, 26H), 0.89 (t, J = 7.0 Hz, 3H). MS (ESI) m/z: 412 [M + H]+. |
| IA-100 | 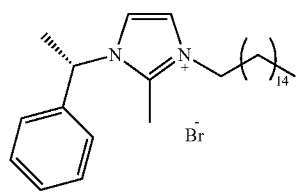 | 1H NMR (600 MHz, Chloroform-d) δ 7.40 (dq, J = 14.1, 7.1 Hz, 5H), 7.19 (d, J = 7.3 Hz, 2H), 5.68 (d, J = 7.2 Hz, 1H), 4.11 (t, J = 7.3 Hz, 2H), 2.59 (s, 3H), 1.92 (d, J = 5.6 Hz, 3H), 1.82 (d, J = 11.3 Hz, 2H), 1.38-1.22 (m, 26H), 0.90 (t, J = 7.0 Hz, 3H). MS (ESI) m/z: 412 [M + H]+. |
| IA-101 | 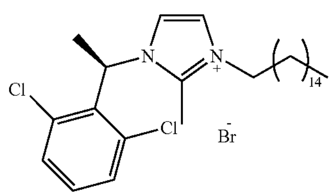 | MS (ESI) m/z: 481 [M + H]+. |
| IA-102 | 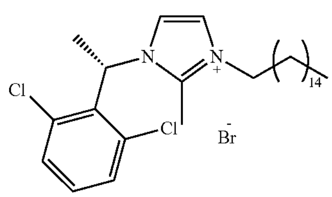 | MS (ESI) m/z: 481 [M + H]+. |
| IB-1 | 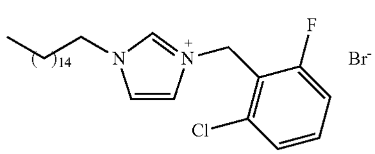 | 1H NMR (600 MHz, Chloroform-d) δ 10.74 (s, 1H), 7.43 (td, J = 8.2, 6.0 Hz, 1H), 7.33 (d, J = 8.1 Hz, 1H), 7.28 (s, 1H), 7.17-7.12 (m, 2H), 5.80 (s, 2H), 4.41 (t, J = 7.4 Hz, 2H), 1.94 (p, J = 7.3 Hz, 2H), 1.35-1.23 (m, 26H), 0.89 (t, J = 7.0 Hz, 3H). MS (ESI) m/z: 437 [M + H]+. |
| IB-2 | 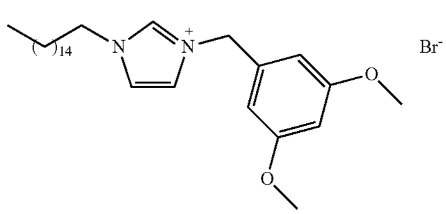 | 1H NMR (600 MHz, Chloroform-d) δ 10.15 (d, J = 1.6 Hz, 1H), 7.47 (t, J = 1.8 Hz, 1H), 7.37 (t, J = 1.9 Hz, 1H), 6.70 (d, J = 2.2 Hz, 2H), 6.42 (t, J = 2.3 Hz, 1H), 5.50 (s, 2H), 4.32-4.22 (m, 2H), 3.79 (s, 6H), 1.90 (t, J = 7.4 Hz, 2H), 1.44-1.16 (m, 26H), 0.86 (t, J = 7.0 Hz, 3H). MS (ESI) m/z: 444 [M + H]+. |

TABLE 1-continued

Structure and characterization of compounds IA-IF

| No. | Structure | 1H NMR and/or MS data |
|---|---|---|
| IB-3 | 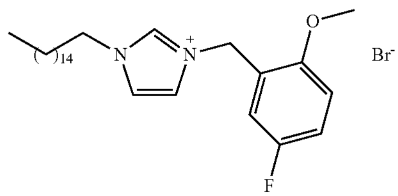 | 1H NMR (600 MHz, Chloroform-d) δ 10.10 (d, J = 1.8 Hz, 1H), 7.50-7.45 (m, 2H), 7.43 (t, J = 1.9 Hz, 1H), 7.06 (td, J = 8.5, 3.1 Hz, 1H), 6.87 (dd, J = 9.1, 4.1 Hz, 1H), 5.53 (s, 2H), 4.33 (t, J = 7.5 Hz, 2H), 3.90 (s, 3H), 1.95-1.89 (m, 2H), 1.55-1.05 (m, 26H), 0.87 (t, J = 7.0 Hz, 3H). MS (ESI) m/z: 432 [M + H]+. |
| IC-1 | 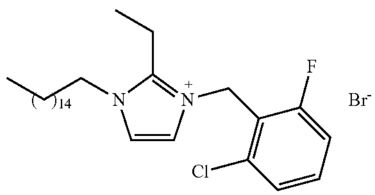 | 1H NMR (600 MHz, Chloroform-d) δ 7.67 (d, J = 2.0 Hz, 1H), 7.45 (q, J = 7.7 Hz, 1H), 7.34 (d, J = 8.1 Hz, 1H), 7.24 (s, 1H), 7.15 (t, J = 8.8 Hz, 1H), 5.60 (s, 2H), 4.26 (t, J = 7.6 Hz, 2H), 3.33 (q, J = 7.6 Hz, 2H), 1.90 (p, J = 7.7 Hz, 2H), 1.35-1.19 (m, 29H), 0.88 (t, J = 6.8 Hz, 3H). MS (ESI) m/z: 465 [M + H]+. |
| IC-2 | 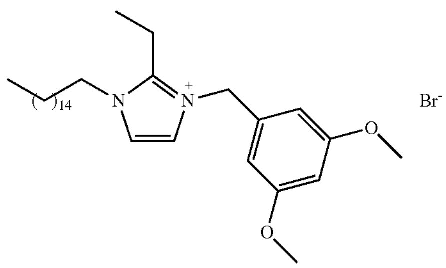 | 1H NMR (600 MHz, Chloroform-d) δ 7.55 (d, J = 2.1 Hz, 1H), 7.47 (d, J = 2.1 Hz, 1H), 6.52 (d, J = 2.1 Hz, 2H), 6.43 (t, J = 2.3 Hz, 1H), 5.48 (s, 2H), 4.17 (t, J = 7.7 Hz, 2H), 3.80 (s, 6H), 3.23 (q, J = 7.7 Hz, 2H), 1.89 (t, J = 7.6 Hz, 2H), 1.26 (m, 26H), 1.19 (t, J = 7.7 Hz, 3H), 0.88 (t, J = 7.0 Hz, 3H). MS (ESI) m/z: 472 [M + H]+. |
| IC-3 | 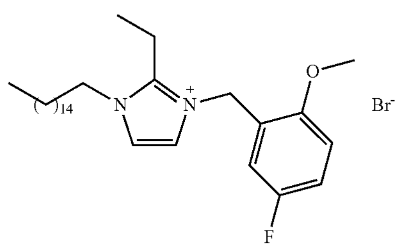 | 1H NMR (600 MHz, Chloroform-d) δ 7.45 (s, 1H), 7.33-7.30 (m, 1H), 7.19 (dd, J = 8.0, 3.1 Hz, 1H), 7.12 (ddd, J = 9.0, 7.8, 2.9 Hz, 1H), 6.90 (dd, J = 9.0, 4.2 Hz, 1H), 5.42 (s, 2H), 4.21 (t, J = 7.5 Hz, 2H), 3.85 (s, 3H), 3.29 (q, J = 7.5 Hz, 2H), 1.91 (t, J = 7.4 Hz, 2H), 1.29 (m, 29H), 0.90 (t, J = 7.0 Hz, 3H). MS (ESI) m/z: 460 [M + H]+. |
| IC-4 | 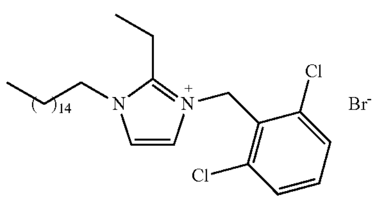 | 1H NMR (600 MHz, Chloroform-d) δ 7.73 (d, J = 2.1 Hz, 1H), 7.46 (d, J = 6.8 Hz, 2H), 7.43 (dd, J = 9.4, 6.4 Hz, 1H), 6.92 (d, J = 2.0 Hz, 1H), 5.66 (s, 2H), 4.31 (t, J = 7.5 Hz, 2H), 3.38 (q, J = 7.6 Hz, 2H), 1.90 (p, J = 7.5 Hz, 2H), 1.43-1.16 (m, 29H), 0.87 (t, J = 6.9 Hz, 3H). MS (ESI) m/z: 481[M + H]+. |
| ID-1 | 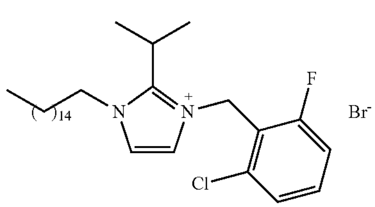 | 1H NMR (600 MHz, Chloroform-d) δ 7.47 (td, J = 8.1, 5.6 Hz, 2H), 7.37 (d, J = 8.1 Hz, 1H), 7.17 (t, J = 8.8 Hz, 1H), 7.05 (s, 1H), 5.53 (s, 2H), 4.22 (t, J = 7.5 Hz, 2H), 3.85-3.73 (m, 1H), 1.86 (t, J = 7.3 Hz, 2H), 1.55 (d, J = 7.0 Hz, 6H), 1.27 (m, 26H), 0.90 (t, J = 7.0 Hz, 3H). MS (ESI) m/z: 479 [M + H]+. |

TABLE 1-continued

Structure and characterization of compounds IA-IF

| No. | Structure | 1H NMR and/or MS data |
|---|---|---|
| ID-2 | 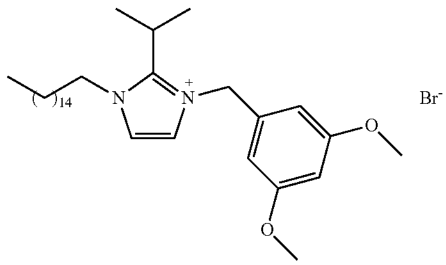 | 1H NMR (600 MHz, Chloroform-d) δ 7.60 (d, J = 2.1 Hz, 1H), 7.55 (d, J = 2.1 Hz, 1H), 6.46 (d, J = 2.2 Hz, 2H), 6.43 (t, J = 2.3 Hz, 1H), 5.58 (s, 2H), 4.30-4.21 (m, 2H), 3.80 (s, 6H), 3.76 (q, J = 7.3 Hz, 1H), 1.89 (p, J = 7.6 Hz, 2H), 1.45 (d, J = 7.3 Hz, 6H), 1.43-1.20 (m, 26H), 0.88 (t, J = 7.0 Hz, 3H). MS (ESI) m/z: 456[M + H]+. |
| ID-3 | 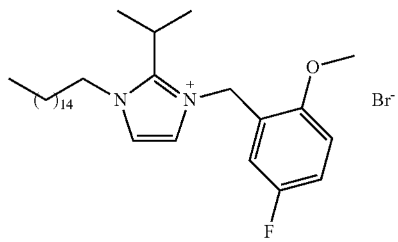 | 1H NMR (600 MHz, Chloroform-d) δ 7.63 (d, J = 2.1 Hz, 1H), 7.33 (d, J = 2.2 Hz, 1H), 7.15 (dd, J = 8.2, 3.1 Hz, 1H), 7.13-7.07 (m, 1H), 6.89 (dd, J = 9.1, 4.2 Hz, 1H), 5.50 (s, 2H), 4.34-4.24 (m, 2H), 3.82 (s, 4H), 1.94-1.85 (m, 2H), 1.51 (d, J = 7.3 Hz, 6H), 1.43-1.21 (m, 26H), 0.88 (t, J = 7.0 Hz, 3H). MS (ESI) m/z: 474[M + H]+. |
| ID-4 | 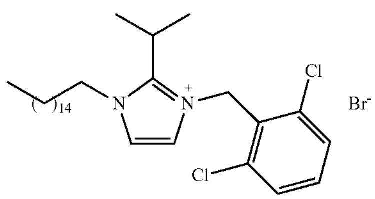 | 1H NMR (600 MHz, Chloroform-d) δ 7.85 (d, J = 2.1 Hz, 1H), 7.49-7.43 (m, 3H), 6.76 (d, J = 2.1 Hz, 1H), 5.68 (s, 2H), 4.40 (t, J = 7.7 Hz, 2H), 4.00 (p, J = 7.2 Hz, 1H), 1.89 (p, J = 7.8 Hz, 2H), 1.61 (d, J = 7.2 Hz, 6H), 1.44-1.18 (m, 26H), 0.87 (t, J = 7.0 Hz, 3H). MS (ESI) m/z: 495[M + H]+. |
| IE-1 | 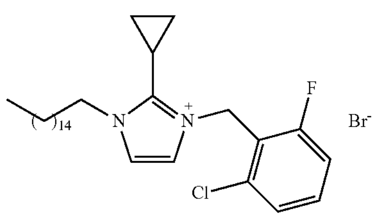 | 1H NMR (600 MHz, Chloroform-d) δ 7.54 (d, J = 2.2 Hz, 1H), 7.44 (td, J = 8.3, 6.0 Hz, 1H), 7.33 (d, J = 8.2 Hz, 1H), 7.14 (t, J = 8.8 Hz, 1H), 7.04 (d, J = 2.2 Hz, 1H), 5.68 (d, J = 1.4 Hz, 2H), 4.40-4.31 (m, 2H), 2.09-2.01 (m, 1H), 1.90 (p, J = 7.4 Hz, 2H), 1.49 (dt, J = 5.6, 2.7 Hz, 2H), 1.47-1.41 (m, 2H), 1.38-1.20 (m, 26H), 0.88 (t, J = 7.0 Hz, 3H). MS (ESI) m/z: 477[M + H]+. |
| IE-2 | 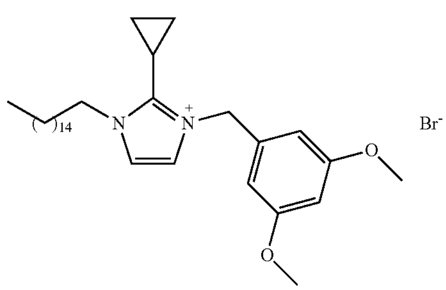 | 1H NMR (600 MHz, Chloroform-d) δ 7.30 (s, 1H), 7.26 (s, 1H), 6.45 (t, J = 2.0 Hz, 1H), 6.32 (d, J = 2.2 Hz, 2H), 5.37 (s, 2H), 4.23 (t, J = 7.6 Hz, 2H), 3.78 (s, 6H), 1.85 (d, J = 9.1 Hz, 2H), 1.40-1.23 (m, 30H), 0.89 (t, J = 7.0 Hz, 3H). MS (ESI) m/z 484[M + H]+. |
| IE-3 | 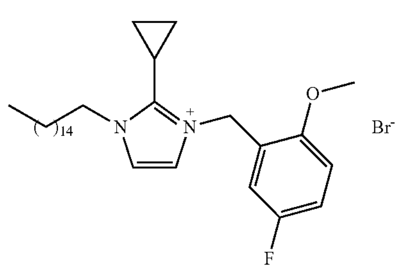 | 1H NMR (600 MHz, Chloroform-d) δ 7.27 (s, 1H), 7.14-7.08 (m, 2H), 7.01 (dd, J = 8.1, 3.1 Hz, 1H), 6.89 (dd, J = 9.0, 4.2 Hz, 1H), 5.36 (s, 2H), 4.23 (t, J = 7.6 Hz, 2H), 3.79 (s, 3H), 1.86 (dt, J = 16.1, 6.7 Hz, 3H), 1.46-1.41 (m, 2H), 1.39-1.21 (m, 26H), 1.20-1.14 (m, 2H), 0.89 (t, J = 7.0 Hz, 3H). MS (ESI) m/z: 472 [M + H]+. |

TABLE 1-continued

Structure and characterization of compounds IA-IF

| No. | Structure | 1H NMR and/or MS data |
|---|---|---|
| IE-4 | 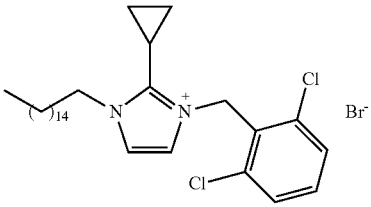 | 1H NMR (600 MHz, Chloroform-d) δ 7.58 (d, J = 2.2 Hz, 1H), 7.47 (d, J = 7.4 Hz, 2H), 7.41 (dd, J = 9.1, 6.9 Hz, 1H), 6.83 (d, J = 2.2 Hz, 1H), 5.77 (s, 2H), 4.39 (t, J = 7.5 Hz, 2H), 2.19-2.08 (m, 1H), 1.92 (p, J = 7.3 Hz, 2H), 1.52 (tt, J = 5.8, 3.3 Hz, 2H), 1.47 (ddd, J = 7.6, 5.6, 3.6 Hz, 2H), 1.40-1.20 (m, 26H), 0.88 (t, J = 7.0 Hz, 3H). MS (ESI) m/z: 493[M + H]+. |
| IF-1 | 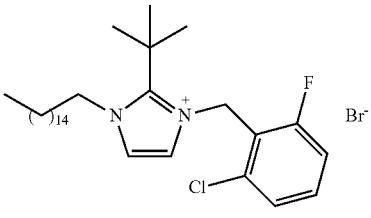 | 1H NMR (600 MHz, Chloroform-d) δ 7.64 (s, 1H), 7.50 (td, J = 8.2, 5.8 Hz, 1H), 7.39 (d, J = 8.1 Hz, 1H), 7.19 (t, J = 8.8 Hz, 1H), 6.80 (s, 1H), 5.67 (s, 2H), 4.45 (s, 2H), 1.90 (d, J = 10.7 Hz, 2H), 1.80 (s, 9H), 1.28 (m, 26H), 0.90 (t, J = 6.9 Hz, 3H). MS (ESI) m/z: 493 [M + H]+. |
| IF-2 | 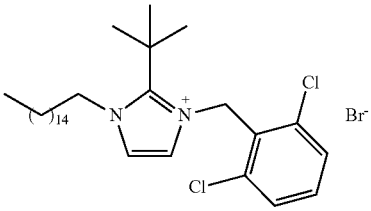 | 1H NMR (600 MHz, Chloroform-d) δ 8.04 (d, J = 2.3 Hz, 1H), 7.52 (d, J = 1.8 Hz, 1H), 7.51 (s, 1H), 7.47 (dd, J = 9.3, 6.7 Hz, 1H), 6.58 (jd, J = 2.2 Hz, 1H), 5.78 (s, 2H), 4.65-4.55 (m, 2H), 1.97-1.91 (m, 2H), 1.86 (s, 9H), 1.27 (m, 26H), 0.89 (d, J = 7.1 Hz, 3H). MS (ESI) m/z: 509 [M + H]+. |

The Compound of Formula II:

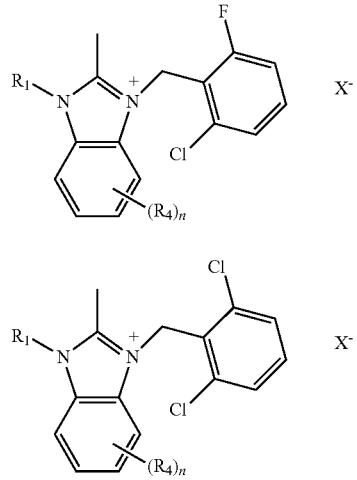

Synthetic Scheme of Compound IIA

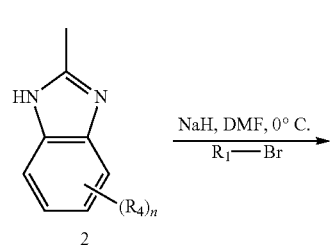

Preparation of Compound 2

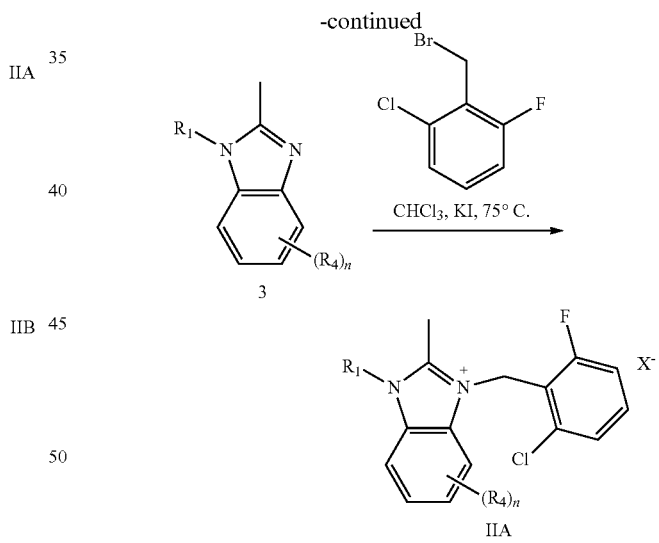

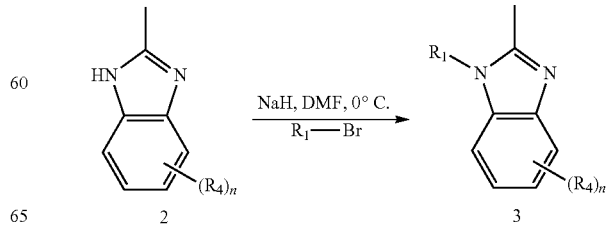

Compound 2 (2.0 mmol) was dissolved in 5 mL of N,N-dimethylformamide, stirred in an ice bath at 0° C., then sodium hydride (140 mg, 3.5 mmol) was added slowly to the solution, followed by further stirring in an ice bath for 30 min; brominated alkane (2.1 mmol) was dissolved in 1 mL of N,N-dimethylformamide, then slowly added dropwise to the above solution, followed by stirring at room temperature, until complete reaction of compound 2 (LC-MS tracking). After the reaction stopped, a large amount of water and ethyl acetate were added successively to the reaction solution, followed by extraction and liquid-liquid separation, the organic phase was washed with saturated sodium chloride solution twice, dried with anhydrous sodium sulfate, concentrated and subjected to silica gel column chromatography (dichloromethane/methanol) to obtain compound 3.

Preparation of Compound IIA

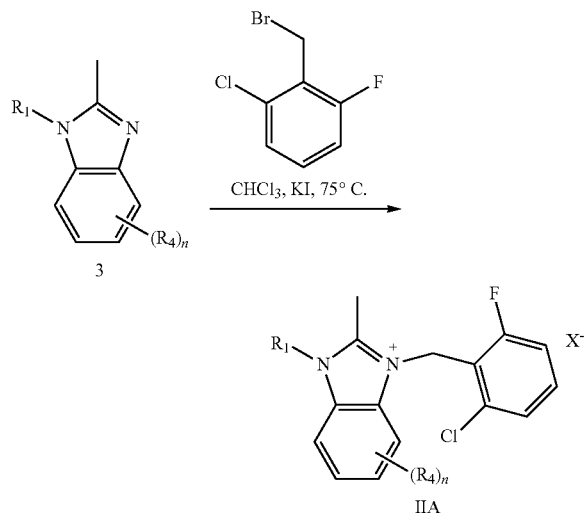

2-Chloro-6-fluorobenzyl bromide (58 mg, 0.252 mmol) and optional KI (83.6 mg, 0.5 mmol) were dissolved successively in 1.5 mL of chloroform, stirred in an oil bath at 75° C. under airtight conditions for 20 min, compound 3 (0.168 mmol) was then added to the system, followed by further stirring in an oil bath at 75° C. under airtight conditions until complete reaction (LC-MS tracking). After the reaction stopped, the system was filtered, the filtrate was concentrated, and subjected to silica gel column chromatography (dichloromethane/methanol), to obtain compound IIA.

Compound IIB could also be synthesized by a similar method.

The synthesis of example compounds is specifically described as follows.

Compound IIA-1

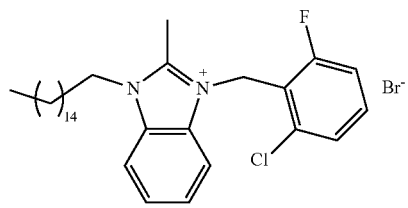

2-Methylbenzoimidazole (2.0 mmol, 264 mg) as raw material B (Appendix 1) was dissolved in 5 mL of N,N-dimethylformamide, stirred in an ice bath at 0° C., then sodium hydride (3.5 mmol, 140 mg) (CAS: 7646-69-7, Energy, Shanghai) was added slowly to the solution, followed by further stirring in an ice bath for 30 min, 1-bromohexadecane (2.1 mmol, 641 mg) as raw material A (Appendix 1) was dissolved in 1 mL of N,N-dimethylformamide, then slowly added dropwise to the above solution, followed by stirring at room temperature for 4 h. After the reaction stopped, a large amount of water and ethyl acetate were added successively to the reaction solution, followed by extraction and liquid-liquid separation, the organic phase was washed with saturated sodium chloride solution twice, dried with anhydrous sodium sulfate, concentrated and subjected to silica gel column chromatography (dichloromethane) to obtain compound

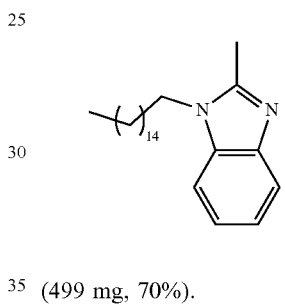

(499 mg, 70%).

2-Chloro-6-fluorobenzyl bromide (0.252 mmol, 58 mg) as raw material C (Appendix 1) and optional KI (0.5 mmol, 83.6 mg) (CAS: 7681-11-0, Energy, Shanghai) were dissolved successively in 1.5 mL of chloroform, stirred in an oil bath at 75° C. under airtight conditions for 20 min, compound

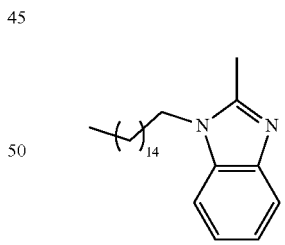

(0.168 mmol, 60 mg) was then added to the system, followed by further stirring in an oil bath at 75° C. under airtight conditions for 8 h. After the reaction stopped, the system was filtered, the filtrate was concentrated, and subjected to silica gel column chromatography (dichloromethane/methanol=50/1), to obtain compound IIA-1.

2. Compounds IIA-2~IIA-5 and IIB-1~IIIB-4 each could be synthesized by a similar method, with the corresponding raw materials listed in Appendix 1.

TABLE 2

Structure and characterization of compounds IIA, IIB

| No. | Structure | 1H NMR and/or MS data |
|---|---|---|
| IIA-1 | 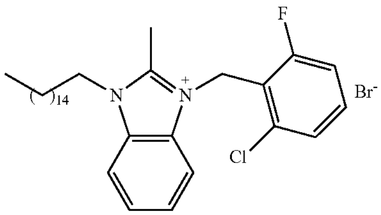 | 1H NMR (600 MHz, Chloroform-d) δ 7.73-7.67 (m, 1H), 7.57 (t, J = 7.6 Hz, 2H), 7.50 (dd, J = 8.7, 6.8 Hz, 1H), 7.39 (td, 8.3, 5.9 Hz, 1H), 7.33 (d, J = 8.2 Hz, 1 H), 7.07 (dd, J = 9.9, 8.3 Hz, 1H), 5.93 (s, 2H), 4.57 (t, J = 7.6 Hz, 2H), 3.33 (s, 3H), 1.94 (p, J = 7.6 Hz, 2H), 1.47-1.14 (m, 26H), 0.88 (t, J = 7.0 Hz, 3H). MS (ESI) m/z: 501[M + H]+. |
| IIA-2 | 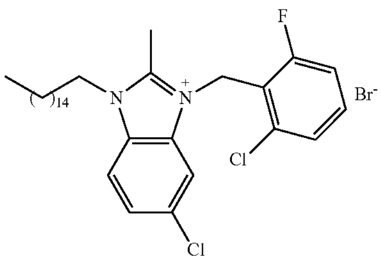 | 1H NMR (600 MHz, Chloroform-d) δ 7.69-7.62 (m, 1H), 7.59 (d, J = 1.7 Hz, 1H), 7.54 (dt, J = 8.8, 1.9 Hz, 1H), 7.45-7.39 (m, 1H), 7.36 (m, 1H), 7.15-7.06 (m, 1H), 5.91 (s, 2H), 4.53 (t, 7.6 Hz, 2H), 3.32 (s, 3H), 1.95 (qd, J = 8.2, 7.8, 3.6 Hz, 2H), 1.46-1.22 (m, 26H), 0.90 (t, J = 7.0 Hz, 3H). MS (ESI) m/z: 535[M + H]+. |
| IIA-3 | 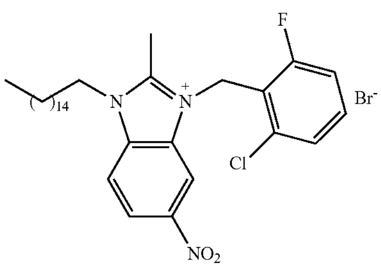 | MS (ESI) m/z: 546[M + H]+. |
| IIA-4 | 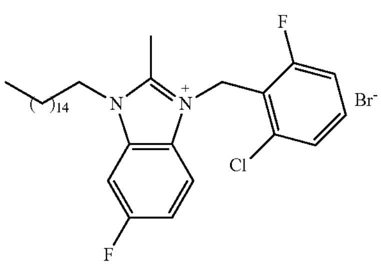 | 1H NMR (600 MHz, DMSO-$d_6$) δ 8.20-8.11 (m, 1H), 7.79 (td, J = 8.7, 3.3 Hz, 1H), 7.56 (m, 2H), 7.50 (dd, J = 8.1, 5.0 Hz, 1H), 7.37-7.31 (m, 1H), 5.92 (s, 2H), 4.49 (m, 2H), 2.87 (s, 3H), 1.76 (p, J = 7.4 Hz, 2H), 1.33-1.16 (m, 26H), 0.85 (t, J = 6.9 Hz, 3H). MS (ESI) m/z: 519[M + H]+. |
| IIA-5 | 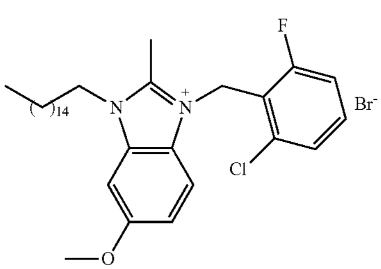 | 1H NMR (600 MHz, Chloroform-d) δ 7.55 (d, J = 9.0 Hz, 1H), 7.41-7.36 (m, 1H), 7.33 (dd, J = 11.0, 8.1 Hz, 1H), 7.13 (td, J = 4.5, 2.2 Hz, 1H), 7.07 (m, 2H), 5.88 (s, 2H), 4.53 (t, 7.5 Hz, 2H), 3.87 (s, 3H), 3.28 (s, 3H), 1.93 (m, 2H), 1.48-1.19 (m, 26H), 0.89 (t, J = 7.0 Hz, 3H). MS (ESI) m/z: 531[M + H]+. |
| IIB-1 | 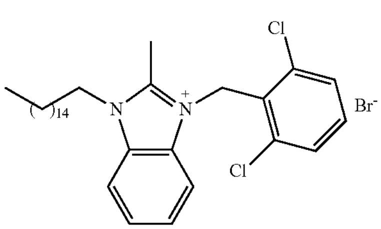 | 1H NMR (600 MHz, Chloroform-d) δ 7.71 (d, J = 8.3 Hz, 1H), 7.53 (t, J = 8.0 Hz, 1H), 7.42 (dd, J = 9.4, 7.7 Hz, 3H), 7.39-7.36 (m, 1H), 7.35 (d, J = 8.3 Hz, 1H), 5.99 (s, 2H), 4.60 (t, J = 7.4 Hz, 2H), 3.31 (s, 3H), 1.91 (p, J = 7.5 Hz, 2H), 1.44-1.13 (m, 26H), 0.86 (t, J = 7.0 Hz, 3H). MS (ESI) m/z: 517[M + H]+. |

TABLE 2-continued

Structure and characterization of compounds IIA, IIB

| No. | Structure | 1H NMR and/or MS data |
|---|---|---|
| IIB-2 | 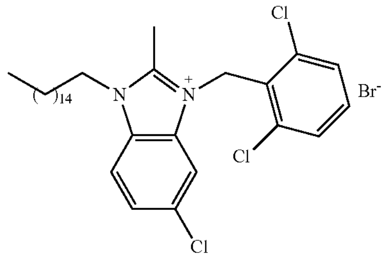 | MS (ESI) m/z: 552[M + H]+. |
| IIB-3 | 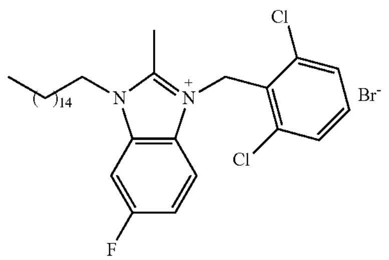 | 1H NMR (600 MHz, Chloroform-d) δ 7.67 (dd, J = 9.1, 4.1 Hz, 1H), 7.46 (t, J = 7.8 Hz, 2H), 7.42-7.38 (m, 1H), 7.38-7.34 (m, 1H), 7.34-7.17 (m, 1H), 5.89 (s, 2H), 4.47 (t, 7.4 Hz, 2H), 3.07 (d, J = 2.6 Hz, 3H), 1.88 (t, J = 7.2 Hz, 2H), 1.50-1.15 (m, 26H), 0.89 (t, J = 7.0 Hz, 3H). MS (ESI) m/z: 535[M + H]+. |
| IIB-4 | 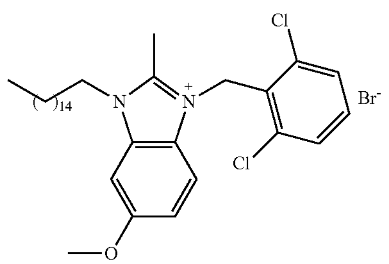 | 1H NMR (600 MHz, Chloroform-d) δ 7.52 (d, J = 9.1 Hz, 1H), 7.45 (t, J = 8.4 Hz, 2H), 7.38 (ddd, J = 8.9, 7.2, 4.3 Hz, 1H), 7.26-7.12 (m, 1 H), 7.07-6.81 (m, 1H), 5.86 (s, 2H), 4.44 (q, J = 7.9 Hz, 2H), 3.83 (s, 3H), 3.04 (s, 3H), 1.88 (t, J = 7.2 Hz, 2H), 1.43-1.17 (m, 26H), 0.89 (t, J = 7.0 Hz, 3H). MS (ESI) m/z: 547[M + H]+. |

Test Examples

Biological Activity Assay:
Activity Assay at Protein Level

The inhibition on aldolase activity of a compound was evaluated by its inhibition on the rate of aldolase-catalyzed degradation of the substrate fructose-1,6-biphosphate (FBP). Method for conjugation of triose phosphate isomerase/glycerol-3-phosphate dehydrogenase [Racker, E. (1952) J. Biol. Chem. 196, 347-351] was specifically used for biochemical activity assay (Table 3).

The specific method was as follows:

About 250 ng of aldolase A was dissolved in 30 μL of water, added to the bottom of a 96-well plate of quartz, and a compound (dissolved in DMSO, not exceeding 1% of the total reaction volume) was added to the aldolase A solution, followed by shaking and mixing, and incubation for 30 min at room temperature;

70 μL of an enzyme reaction system (its formulation was given below) was added, and immediately put into a microplate reader (SpectraMax M5, Molecular Devices), to carry out reaction at 37° C. At the same time, the absorbance at 340 nM was measured every 30 s, and a total of 61 absorbance values were obtained for each well. The absorbance value linearly changed with time, and the slope was the enzyme activity of aldolase in the well. The specific value was calculated by SoftMax Pro 5.4.1;

Enzyme Reaction System:
  enzyme reaction buffer (50 mM TEA-HCl, pH 7.4, 10 mM EDTA)
  FBP (500 μM)
  NADH (1 mM)
  triose phosphate isomerase (about 20 U)
  glycerol-3-phosphate dehydrogenase (about 2 U)
  DTE (20 mM)

Two parallel experiments were set for each group, with DMSO having a final concentration of 1% as the blank control, and the final concentration of compound being 100 μM. The inhibition rate of aldolase activity was calculated by the following equation:

Aldolase activity inhibition rate %=($V$test group−$V$blank group)/$V$blank group*100%

TABLE 3

Aldolase activity inhibition results of compounds

| No. | Inhibition rate (%) |
|---|---|
| IA-6 | 83.40 |
| IA-7 | 88.40 |
| IA-10 | 0.06 |
| IA-14 | 5.06 |
| IA-18 | 86.93 |
| IA-20 | 18.12 |
| IA-21 | 14.37 |
| IA-28 | 63.88 |
| IA-30 | 15.23 |
| IA-31 | 86.13 |
| IA-34 | 20.40 |
| IA-40 | 26.96 |

TABLE 3-continued

Aldolase activity inhibition results of compounds

| No. | Inhibition rate (%) |
| --- | --- |
| IA-41 | 75.43 |
| IA-44 | 90.70 |
| IA-45 | 86.76 |
| IA-48 | 88.64 |
| IA-49 | 78.73 |
| IA-50 | 33.14 |
| IA-56 | 49.78 |
| IA-59 | 72.57 |
| IA-61 | 23.60 |
| IA-62 | 87.40 |
| IA-63 | 8.26 |
| IA-66 | 20.68 |
| IA-69 | 81.71 |
| IA-72 | 76.93 |
| IA-87 | 51.23 |
| IA-97 | 22.45 |
| IC-1 | 47.05 |
| IC-3 | 81.36 |
| IC-4 | 2.84 |
| ID-1 | 71.39 |
| IE-3 | 49.20 |
| IF-2 | 76.77 |
| IIA-1 | 49.89 |
| IIA-2 | 44.02 |
| IIA-4 | 83.39 |
| IIA-5 | 83.90 |
| IIB-1 | 48.47 |
| IIB-2 | 86.22 |
| IIB-3 | 86.74 |
| IIB-4 | 84.16 |

*Test concentration of compound was 100 μM.

2. Activity Assay at Cell Level

The aldolase inhibitory effect of a compound in mouse embryonic fibroblasts (MEFs) could be determined by detecting the activation of AMPK in MEFs, which could be specifically carried out by detecting the phosphorylation level (p-AMPK) of threonine at the 172nd position of AMPK and the phosphorylation level (p-AGO) of serine at the 79th position of the substrate ACC1/ACC2 of AMPK (FIG. 1) by western blot.

Figure 2:
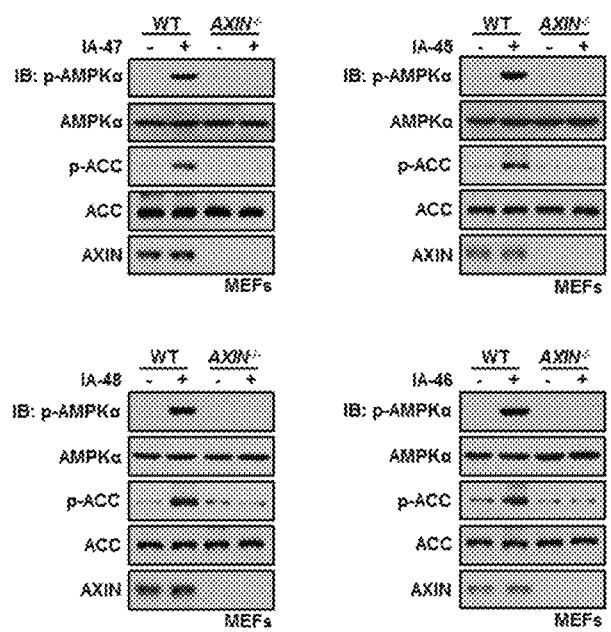
FIG. 2 shows that the compounds activate AMPK via a protein AXIN-dependent signaling pathway. In the AXIN knockout MEFs, none of the tested compounds could effectively activate AMPK (the compound concentration being 200 nM).
Figure 3:
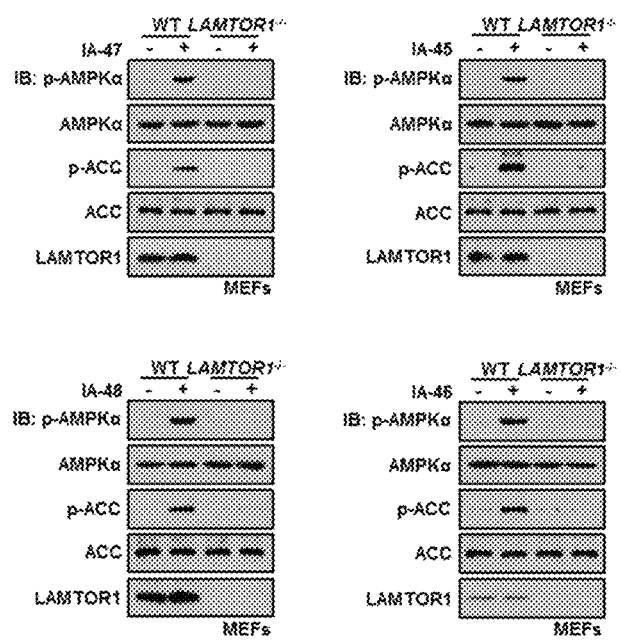
FIG. 3 shows that the compounds activate AMPK via a protein LAMTOR1-dependent signaling pathway. In the LAMTOR1 knockout MEFs, none of the tested compounds could effectively activate AMPK (the compound concentration being 200 nM).

Further experiments showed that none of the compounds could effectively activate AMPK in the proteins AXIN (FIG. 2)- and LAMTOR1 (FIG. 3)-knocked out MEFs, which proved that the tested compounds played the role of activating AMPK through the Aldolase-AXIN-LAMTOR1 signaling pathway.

The specific method was as follows:

MEFs with loxP insertion sequences or of wild-type were plated in a 6-well plate and cultured in DMEM containing 10% serum. If a gene needed to be knocked out at this time, when the density of the corresponding MEFs with loxP insertion sequences reached about 30%, an adenovirus capable of expressing cre should be added to the culture well followed by further culture for more than 24 h;

When the cell density was close to 90%, the cells were provided with fresh DMEM, at the same time, a compound (final concentration 200 NM) was added to the cells, followed by culture for 2 h, with an equal volume of DMSO as the negative control, and the cells treated with DMEM medium without glucose as the positive control;

After sucking up the culture solution, the cells were lysed with 200 μL of a cell lysate (its formulation was given below), then the cells were scraped from the culture dish, ultrasonicated, and subjected to low temperature centrifugation at 20000 g for 10 min;

The supernatant and an equal volume of 2*SDS solution (its formulation was given below) were mixed, and subjected to SDS-PAGE in a concentration of 8%, then the protein was transferred to PVDF membrane; each PVDF membrane was blocked with 25 mL of skim milk for 1 h, and then rinsed with TBST buffer (its formulation was given below) 3 times for 10 min each time;

AMPKα subunit primary antibody (Cell Signaling Technology, #2532), primary antibody of phosphothreonine at the 172nd position of AMPK (Cell Signaling Technology, #2535), ACC primary antibody (Cell Signaling Technology, #3662), primary antibody of phosphoserine at the 79th position of ACC (Cell Signaling Technology, #3661), LAMTOR1 primary antibody (Cell Signaling Technology, #8975), AXIN primary antibody (Cell Signaling Technology, #2074) or LKB1 primary antibody (Cell Signaling Technology, #3047) was diluted in a ratio of 1:1000 with a primary antibody dilution (its formulation was given below), reacted with the PVDF membrane at room temperature for 12 h, and then rinsed 3 times with TBST buffer;

A 1:1000 dilution of HRP-conjugated goat anti-rabbit secondary antibody (Jackson ImmunoResearch, 111-035-003) was added, reacted at room temperature for 1 h, and then rinsed 3 times with TBST buffer;

The PVDF membrane was dried, reacted in an ECL mixture (WesternBright ECL HRP substrate, Advansta) and subjected to exposure with medical X-ray, developed, finally rinsed, dried, and then scanned to obtain data related to AMPK activation.

The formulations of reagents used were:

Cell lysate: 20 mM Tris-base, pH 7.5, 150 mM NaCl, 1 mM EDTA, 1 mM EGTA, 2.5 mM Sodium pyrophosphate, 1 mM β-glycerolphosphate, 1% Triton X-100 (v/v);

2*SDS solution: 20% Glycerol (v/v), 4% SDS (m/v), 10% β-mercaptoethanol (v/v), 0.01% Bromophenol blue (m/v);

TBST buffer: 4.84% Tris-base (m/v), 8% NaCl (m/v), 0.1% Tween-20 (v/v);

Primary antibody dilution: TBST buffer containing 5% BSA (v/v)

3. Mouse Physiological Activity Assay

Figure 4:
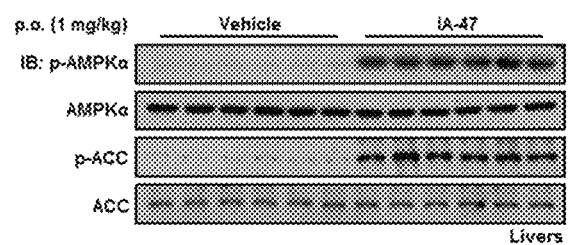
FIG. 4 shows that the compound (IA-47) activates AMPK activity in the liver of mice by inhibiting aldolase activity. In high-fat-fed obese mice, oral administration (1 mg/kg, once/day) for two weeks effectively inhibited aldolase activity and activated AMPK activity in the liver of mice.
Figure 5:
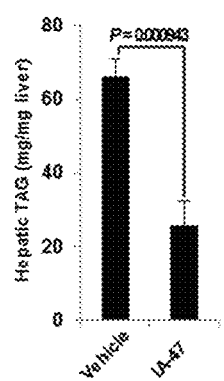
FIG. 5 shows that the compound (IA-47) lowers the level of triglyceride in mice by inhibiting aldolase activity. In high-fat-fed obese mice, oral administration (1 mg/kg, once/day) for two weeks effectively inhibited aldolase activity and decreased triglyceride level in the liver of mice.
Figure 6:
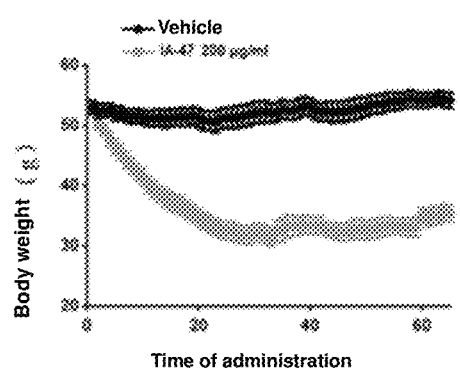
FIG. 6 shows that the compound (IA-47) significantly reduces the body weight of high-fat-fed obese mice. High-fat-fed obese mice were administered with a drug dissolved in drinking water (200 μg/ml), and after 30 days of feeding, their body weights reduced from more than 50 g to a normal level of about 30 g.
Figure 7:
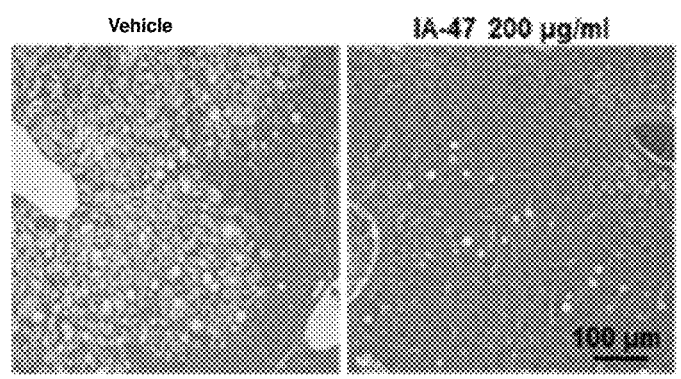
FIG. 7 shows that the compound (IA-47) is effective in the treatment of fatty liver in high-fat-fed obese mice. The liver of the mice treated according to FIG. 6 was taken and sectioned. The histological features of the liver were directly observed after HE staining. The fat content in the sections was significantly reduced, indicating that the fatty liver was effectively relieved.
Figure 8:
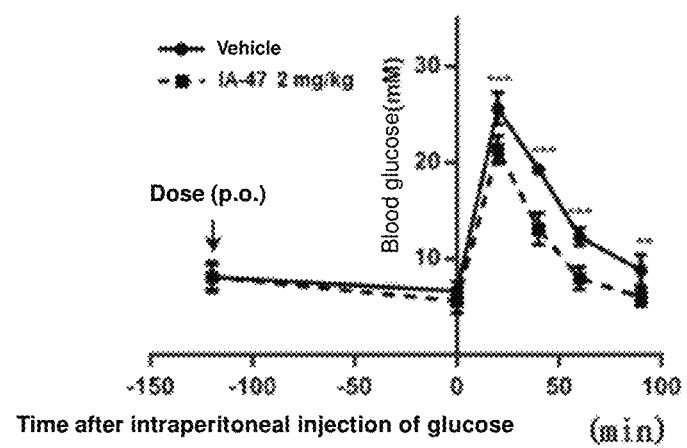
FIG. 8 shows that the compound (IA-47) significantly lowers blood sugar in iv-GTT. The fasting normal mice were intragastrically administered with 2 mg/kg of IA-47, and after 2 hours of absorption, intraperitoneally injected with glucose (1 g/kg), and the blood sugar changes were measured at the corresponding time points.

The effect of a compound to activate AMPK in liver of mice by inhibiting aldolase activity was determined by intragastric administration or by dissolving the drug in drinking water and feeding it to the mice, and then detecting triglyceride (TAG) level in the liver, and detecting the phosphorylation level of threonine at the 172nd position of AMPK and the phosphorylation level of serine at the 79th position of the substrate ACC1/ACC2 of AMPK by western blot (FIG. 4 and FIG. 5). In addition, the effect of the compound through AMPK was further illustrated by detecting the body weight of mice after administration (FIG. 6), the morphology of liver slices (FIG. 7) and the influence of intragastric administration on the blood sugar level (FIG. 8). FIG. 4 showed that the compound (IA-47) could activate AMPK activity in the liver of mice by inhibiting aldolase activity. FIG. 5 showed that the compound (IA-47) could lower the level of triglyceride in mice by inhibiting aldolase activity. FIG. 6 showed that the compound (IA-47) could significantly reduce the body weight of high-fat-fed obese mice. FIG. 7 showed that the compound (IA-47) was effective in the treatment of fatty liver in high-fat-fed obese mice.

FIG. 8 showed that the compound (IA-47) could significantly lower blood sugar in iv-GTT.

The specific method was as follows:

(1) 6-week wild-type C57BL/6J male mice were high-fat fed with 60% fat, after 10 weeks, the body weight reached 50 g, then, drug treatment was started, and the high-fat diet was maintained during the drug treatment.

(2) At 5 pm every day, the mice were weighed, and intragastrically administered with IA-47 at a concentration of 1 mg/kg, and intragastrically administered with vehicle in the same proportion.

(3) Two weeks after administration, the mice were killed by cervical dislocation, the liver of the mice was quickly taken out, placed in a 1.5 mL tube and quenched in liquid nitrogen.

(4) About 50 mg of the liver was cut, and a cell lysate (its formulation was given below) was added at a ratio of 1 mg/μL, followed by homogenization and ultrasonication, and low temperature centrifugation at 20000 g for 10 min.

(5) The supernatant and an equal volume of 2*SDS solution (its formulation was given below) were mixed, subjected to SDS-PAGE in a concentration of 8%, then the protein was transferred to PVDF membrane; each PVDF membrane was blocked with 25 mL of skim milk for 1 h, and then rinsed with TBST buffer (its formulation was given below) 3 times for 10 min each time;

(6) AMPKα subunit primary antibody (Cell Signaling Technology, #2532), primary antibody of phosphothreonine at the 172nd position of AMPK (Cell Signaling Technology, #2535), ACC primary antibody (Cell Signaling Technology, #3662), primary antibody of phosphoserine at the 79th position of ACC (Cell Signaling Technology, #3661), LAMTOR1 primary antibody (Cell Signaling Technology, #8975), AXIN primary antibody (Cell Signaling Technology, #2074) or LKB1 primary antibody (Cell Signaling Technology, #3047) was diluted in a ratio of 1:1000 with a primary antibody dilution (its formulation was given below), reacted with the PVDF membrane at room temperature for 12 h, and then rinsed 3 times with TBST buffer;

(7) A 1:1000 dilution of HRP-conjugated goat anti-rabbit secondary antibody (Jackson ImmunoResearch, 111-035-003) was added, reacted at room temperature for 1 h, and then rinsed 3 times with TBST buffer;

(8) The PVDF membrane was dried, reacted in an ECL mixture (WesternBright ECL HRP substrate, Advansta) and subjected to exposure with medical X-ray, developed, finally rinsed, dried, and then scanned to obtain data related to AMPK activation.

(9) Another 80 mg of the liver was taken, and 800 μL of a liver lysate (its formulation was given below) was added, followed by homogenization and crushing, and incubation for 5 min in boiling water.

(10) After heat centrifugation, the supernatant was transferred to a new tube.

(11) 2 μL of the supernatant was pipetted to a 96-well plate, a standard solution (Wako 290-63701) was added to the 96-well plate, and 300 μL of a color developing solution (Wako 290-63701) was added each well, to carry out reaction at 37° C. for 5 min.

(12) The absorbance at 600 nm was read with a microplate reader (SpectraMax M5, Molecular Devices), and the level of triglyceride was calculated according to the instructions.

(13) The high-fat-fed obese mice weighing more than 50 g were continuously fed with the drug dissolved in drinking water (200 μg/ml) for 70 days, weighed every day, and euthanized on the 70th day. Their livers were taken out, fixed, sectioned, and histological features thereof were directly observed after HE staining.

(14) 6-week wild-type C57BL/6J male mice started to fast at 6:00 am; after 4 h, the blood sugar (−120 min) and the body weight were measured, the mice were intragastrically administered with IA-47 at a dose of 2 mg/kg, and intragastrically administered with vehicle in the same proportion.

(15) After 2 h, the blood sugar (0 min) was measured, the mice were intraperitoneally injected with 20% (v/v) glucose solution at a concentration of 1 g/kg, and then the blood sugar was measured respectively at 20, 40, 60, and 90 min after the injection.

The formulations of reagents used were:

Cell lysate: 20 mM Tris-base, pH 7.5, 150 mM NaCl, 1 mM EDTA, 1 mM EGTA, 2.5 mM Sodium pyrophosphate, 1 mM β-glycerolphosphate, 1% Triton X-100 (v/v);

2*SDS solution: 20% Glycerol (v/v), 4% SDS (m/v), 10% β-mercaptoethanol (v/v), 0.01% Bromophenol blue (m/v);

TBST buffer: 4.84% Tris-base (m/v), 8% NaCl (m/v), 0.1% Tween-20 (v/v);

Primary antibody dilution: TBST buffer containing 5% BSA (v/v)

Liver lysate: PBS solution containing 5% Triton X-100 (v/v).

4. Nematode Lifespan Assay

Figure 9:
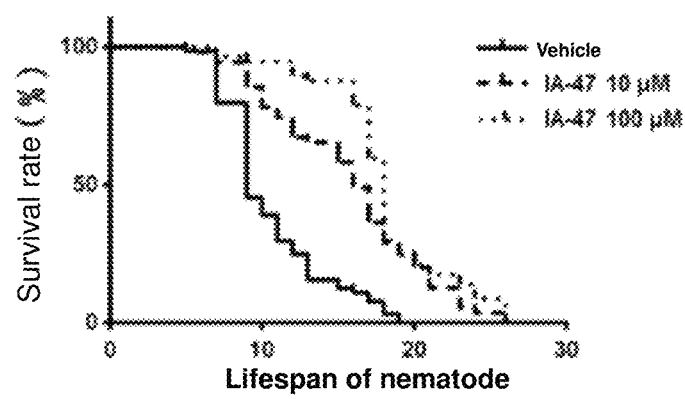
FIG. 9 shows that the compound (IA-47) is capable of extending the lifespan of nematodes.

The effect of a compound to activate AMPK in liver of mice by inhibiting aldolase activity was determined by dissolving the drug in a nematode medium, observing the number of surviving nematodes per day, and plotting survival curves (FIG. 9). FIG. 9 showed that the compound (IA-47) was capable of extending the lifespan of nematodes by inhibiting aldolase activity.

APPENDIX 1

Some commercial raw materials used for the synthesis of example compounds

Raw material A bromomethane, CAS: 74-83-9, Aladdin, Shanghai
bromoethane, CAS: 74-96-4, Macklin, Shanghai
1-bromopropane, CAS: 106-94-5, Macklin, Shanghai
2-bromopropane, CAS: 75-26-3, Macklin, Shanghai
n-bromobutane, CAS: 109-65-9, Macklin, Shanghai
bromo-n-pentane, CAS: 110-53-2, Macklin, Shanghai
bromohexane, CAS: 111-25-1, Macklin, Shanghai
1-bromoheptane, CAS: 629-04-9, Macklin, Shanghai
bromooctane, CAS: 111-83-1, Macklin, Shanghai
1-bromononane, CAS: 693-58-3, Macklin, Shanghai
cetyl bromide, CAS: 112-29-8, Macklin, Shanghai
1-bromoundecane, CAS: 693-67-4, Macklin, Shanghai
1-bromododecane, CAS: 143-15-7, Macklin, Shanghai
1-bromotridecane, CAS: 765-09-3, Macklin, Shanghai
1-bromotetradecane, CAS: 112-71-0, Macklin, Shanghai
1-bromopentadecane, CAS: 629-72-1, Macklin, Shanghai
1-bromohexadecane, CAS: 112-82-3, Macklin, Shanghai
1-bromoheptadecane, CAS: 3508-00-7, Macklin, Shanghai
1-bromooctadecane, CAS: 112-89-0, Macklin, Shanghai
1-bromoeicosane, CAS: 4276-49-7, Macklin, Shanghai
1-bromodocosane, CAS: 6938-66-5, Macklin, Shanghai Raw material B imidazole, CAS: 288-32-4, Macklin, Shanghai
2-methylimidazole, CAS: 693-98-1, Acros Organics, Belgium
2-ethylimidazole, CAS: 1072-62-4, Macklin, Shanghai
2-isopropylimidazole, CAS: 36947-68-9, Bide, Shanghai
2-t-butylimidazole, CAS: 36947-69-0, Accela ChemBio, Shanghai
2-cyclopropyl-1 H-imidazole, CAS: 89532-38-7, HWRK, Beijing
2-methylbenzoimidazole, CAS: 615-15-6, Bide, Shanghai
2-methyl-5-chlorobenzoimidazole, CAS: 2818-69-1, Accela ChemBio, Shanghai
2-methyl-5-nitrobenzoimidazole, CAS: 1792-40-1, Bide, Shanghai
5-fluoro-2-methylbenzoimidazole, CAS: 118469-15-1, Bide, Shanghai APPENDIX 1-continued Some commercial raw materials used for the synthesis of example compounds Raw material C 2-chloro-6-fluorobenzyl bromide, CAS: 68220-26-8, Bide, Shanghai
2,6-dichlorobenzyl bromide, CAS: 20443-98-5, Energy, Shanghai
5-fluoro-2-methoxybenzyl bromide, CAS: 20-3-560364, Energy, Shanghai
3,5-dimethoxybenzyl bromide, CAS: 877-88-3, Adamas, Shanghai
2-fluorobenzyl bromide, CAS: 446-48-0, Energy, Shanghai
3-fluorobenzyl bromide, CAS: 456-41-7, Energy, Shanghai
4-fluorobenzyl bromide, CAS: 459-46-1, Energy, Shanghai
2-chlorobenzyl bromide, CAS: 611-17-6, Energy, Shanghai
3-chlorobenzyl bromide, CAS: 766-80-3, Energy, Shanghai
4-chlorobenzyl bromide, CAS: 622-95-7, Energy, Shanghai
2-bromobenzyl bromide, CAS: 3433-80-5, Energy, Shanghai
3-bromobenzyl bromide, CAS: 823-78-9, Energy, Shanghai
4-bromobenzyl bromide, CAS: 589-15-1, Energy, Shanghai
2-methylbenzyl bromide, CAS: 9-92-9, Energy, Shanghai
3-methylbenzyl bromide, CAS: 620-13-3, Energy, Shanghai
4-methylbenzyl bromide, CAS: 104-81-4, Energy, Shanghai
3-methoxybenzyl bromide, CAS: 874-98-6, Energy, Shanghai
4-methoxybenzyl bromide, CAS: 2746-25-0, Energy, Shanghai
2-(trifluoromethyl)benzyl bromide, CAS: 395-44-8, Energy, Shanghai
3-(trifluoromethyl)benzyl bromide, CAS: 402-23-3, Energy, Shanghai
1-bromo-trifluoro p-xylene, CAS: 402-49-3, Energy, Shanghai
2-(trifluoromethoxy)benzyl bromide, CAS: 198649-68-2, Energy, Shanghai
3-trifluoromethoxybenzyl bromide, CAS: 159689-88-0, Energy, Shanghai
4-trifluoromethoxybenzyl bromide, CAS: 50824-05-0, Energy, Shanghai
2-cyanobenzyl bromide, CAS: 22115-41-9, Energy, Shanghai
3-cyanobenzyl bromide, CAS: 28188-41-2, Energy, Shanghai
p-cyanobenzyl bromide, CAS: 17201-43-3, Energy, Shanghai
2,6-dimethylbenzyl bromide, CAS: 83902-02-7, Energy, Shanghai
2,6-difluorobenzyl bromide, CAS: 85118-00-9, Energy, Shanghai

-continued
IA-94
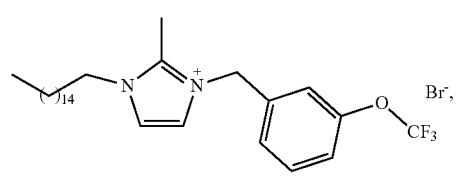
IA-95
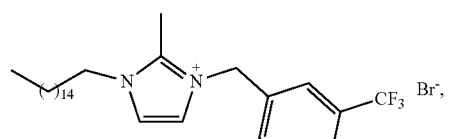
IA-96
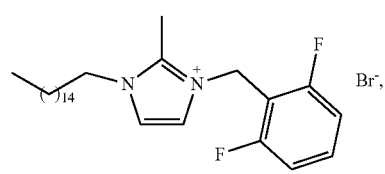
IA-97
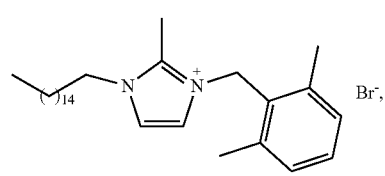
IA-98
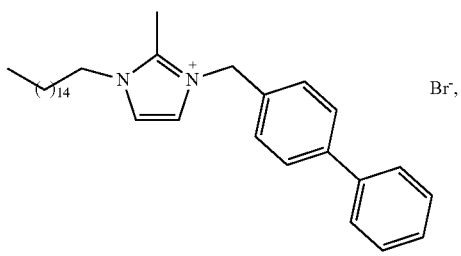
IA-99
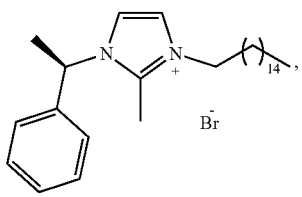
IA-100
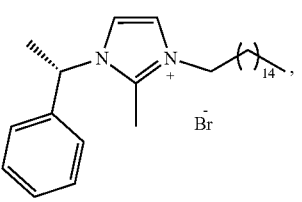
IA-101
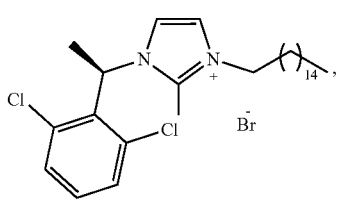
-continued
IA-102
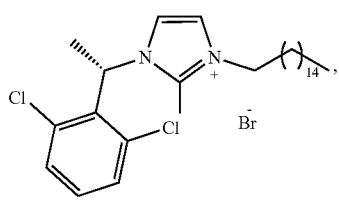
IB-1
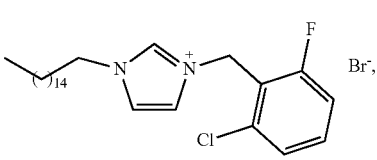
IB-2
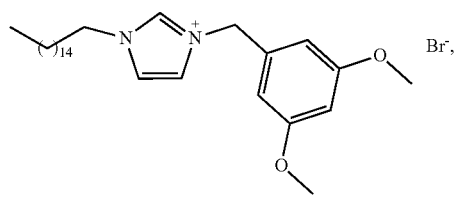
IB-3
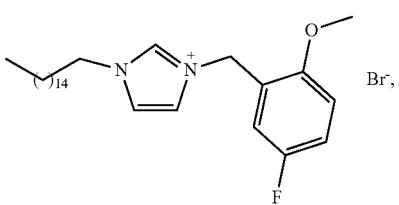
IC-1
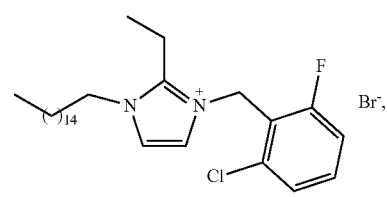
IC-2
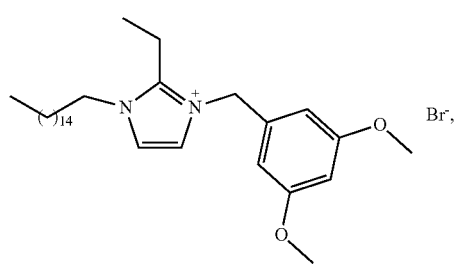
IC-3
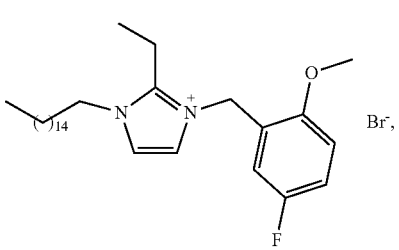

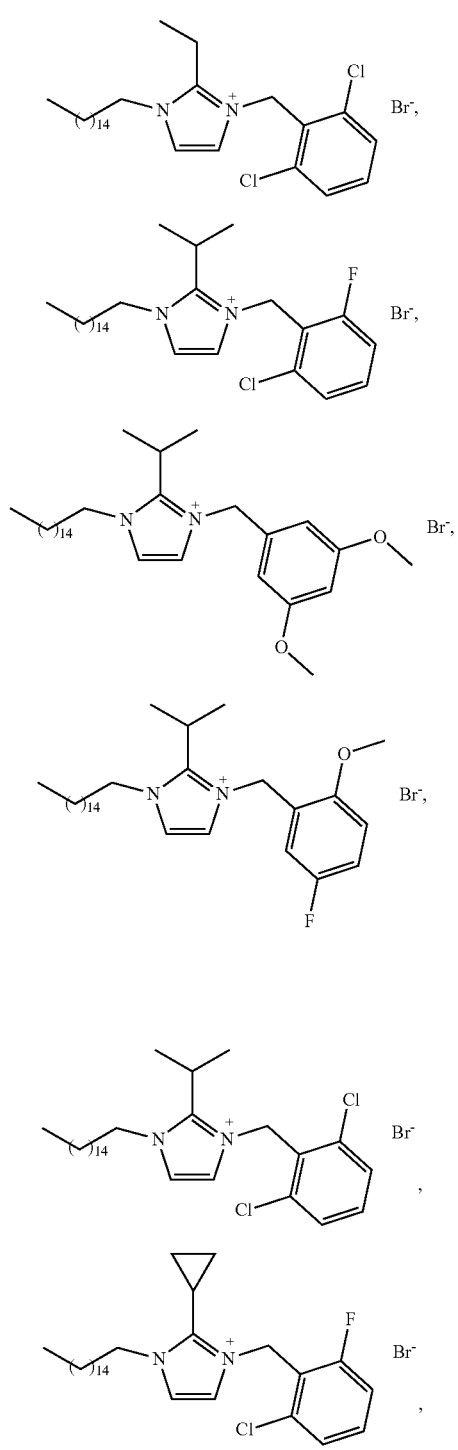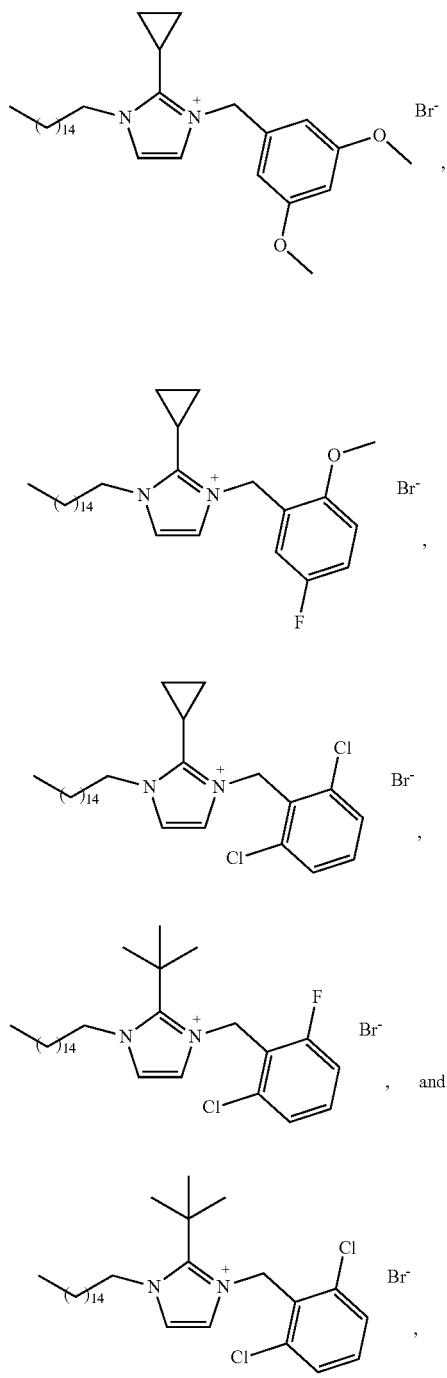

What is claimed is:

1. A method of inhibiting aldolase activity, comprising contacting the compound having the general formula

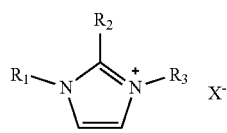

I or a stereoisomer thereof, a prodrug thereof, a pharmaceutically acceptable salt thereof or a pharmaceutically acceptable solvate thereof or a pharmaceutical composition comprising the above compound with the aldolase:
wherein
$R_1$ is C1-C22 alkyl;
$R_2$ is selected from the group consisting of H, methyl, ethyl, isopropyl, t-butyl, and cyclopropyl;
$R_3$ is selected from the group consisting of:
1) Formula (a),

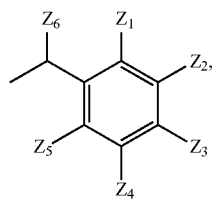

wherein any two of $Z_1$, $Z_2$, $Z_4$, $Z_5$ each are independently selected from the group consisting of:

(1) H, F, Cl, Br, and cyano; and (2) C1-C3 alkyl, C1-C3 alkoxy, C1-C3 fluorine-containing alkyl, and C1-C3 fluorine-containing alkoxy;

the rest and $Z_3$ being H;

$Z_6$ is H or methyl; and 2) formula (b),

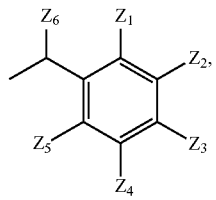

wherein for $Z_1$, $Z_2$, $Z_3$, $Z_4$, and $Z_5$:

one is independently selected from the following groups:

(1) H, F, Cl, Br, and cyano;

(2) C1-C3 alkyl, C1-C3 alkoxy, C1-C3 fluorine-containing alkyl, and C1-C3 fluorine-containing alkoxy;

the rest being H;

$Z_6$ is H or methyl;

$X^-$ is an anion of a pharmaceutically acceptable inorganic or organic acid salt.

2. The method according to claim 1, wherein
$R_3$ is formula (a),

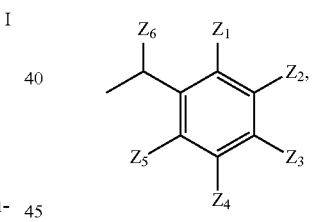

wherein for $Z_1$, $Z_2$, $Z_3$, $Z_4$, and $Z_5$:

$Z_1$, $Z_5$, or $Z_2$, $Z_4$, or $Z_1$, $Z_4$ each are independently selected from the group consisting of:

(1) H, F, Cl, Br, and cyano; and (2) C1-C3 alkyl, C1-C3 alkoxy, C1-C3 fluorine-containing alkyl, and C1-C3 fluorine-containing alkoxy;

$Z_6$ is H or methyl.

3. The method according to claim 1, wherein the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, a-ketoglutarate, a-glycerophosphate, alkyl sulfonate or aryl sulfonate; or, said alkyl sulfonate is methyl sulfonate or ethyl sulfonate; said aryl sulfonate is benzenesulfonate or p-toluenesulfonate.

4. The method according to claim 1, wherein

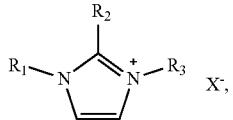

is selected from the group consisting of:

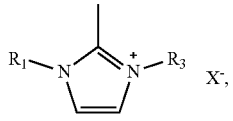  IA

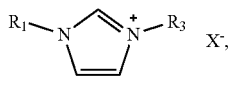  IB

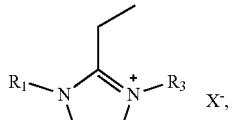  IC

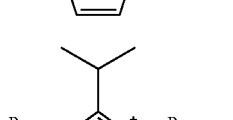  ID

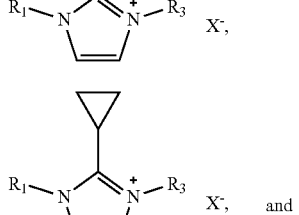  IE  and

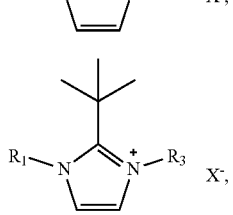  IF wherein $R_1$, $R_3$ and $X^-$ are as defined in claim 1.

5. A method of inhibiting aldolase activity, comprising contacting a compound or a stereoisomer thereof, a prodrug thereof, a pharmaceutically acceptable salt thereof or a pharmaceutically acceptable solvate thereof or a pharmaceutical composition comprising the above compound, wherein the compound is selected from the group consisting of:

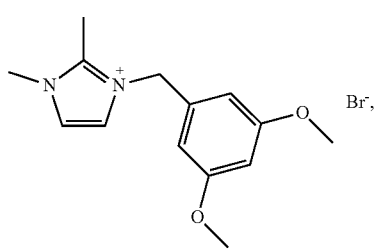  IA-1

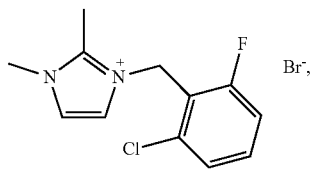  IA-2

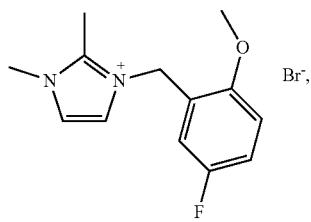  IA-3

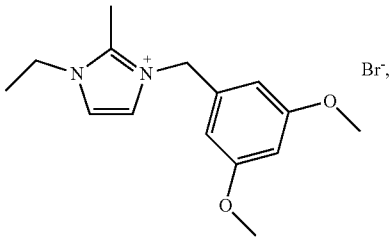  IA-4

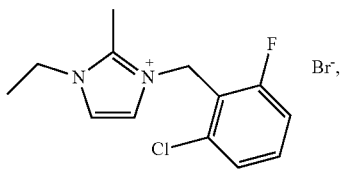  IA-5

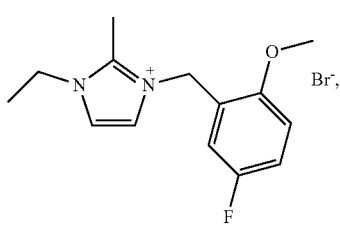  IA-6

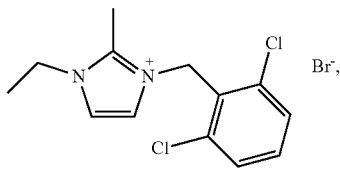  IA-7

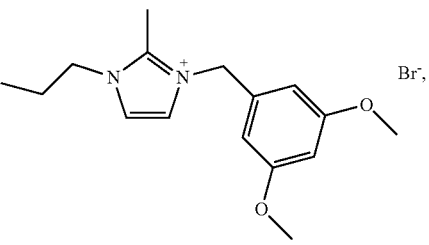  IA-8

IA-9
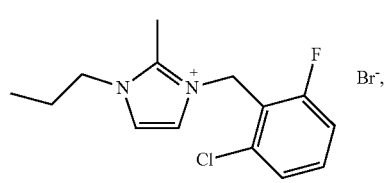
IA-10
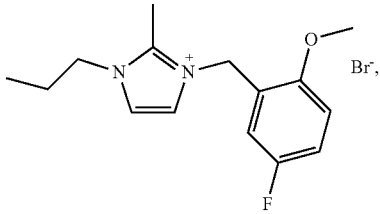
IA-11
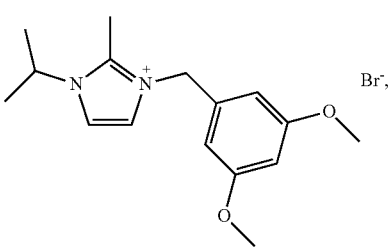
IA-12
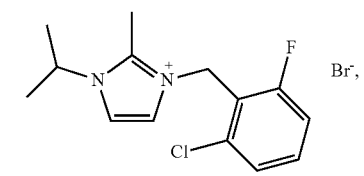
IA-13
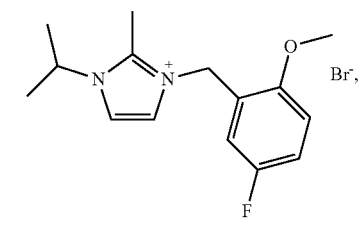
IA-14
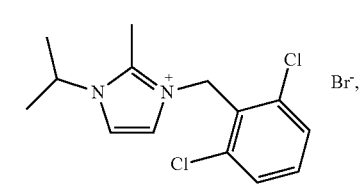
IA-15
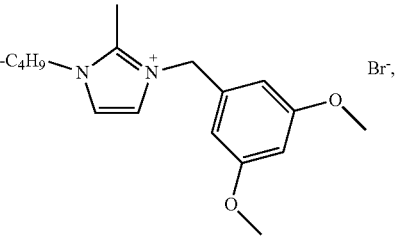
IA-16
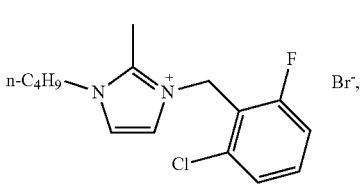
IA-17
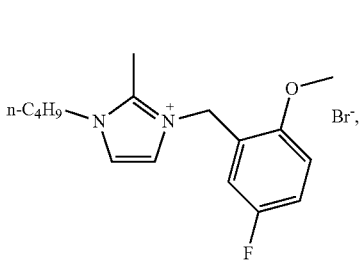
IA-18
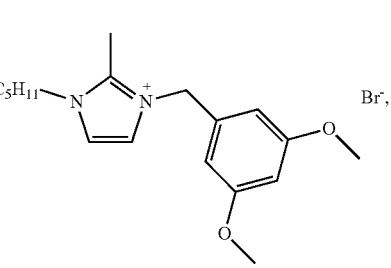
IA-19
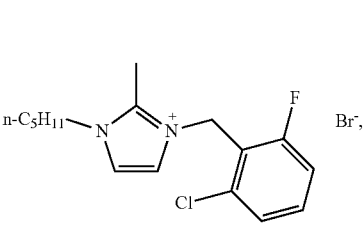
IA-20
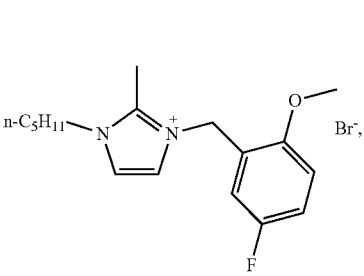
IA-21
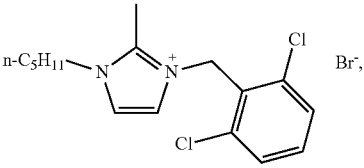
IA-22
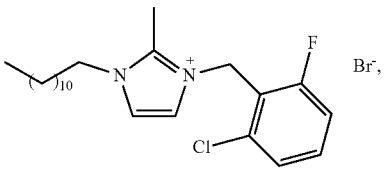

-continued
IA-23
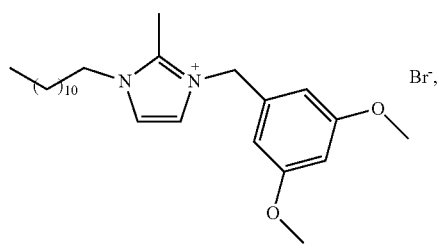
IA-24
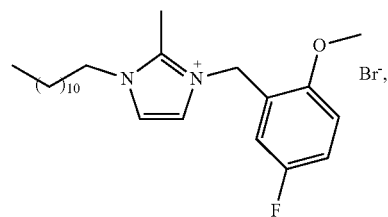
IA-25
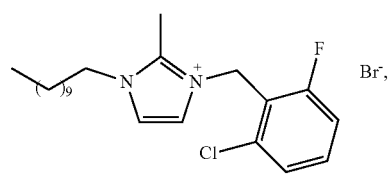
IA-26
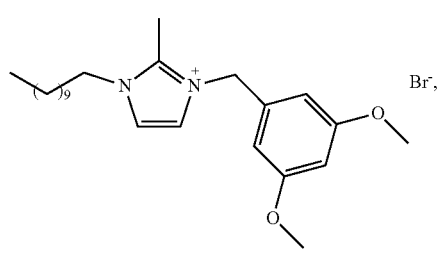
IA-27
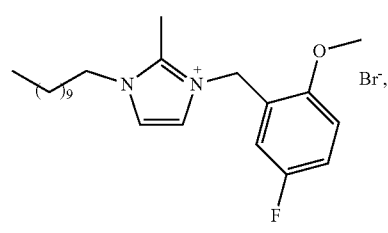
IA-28
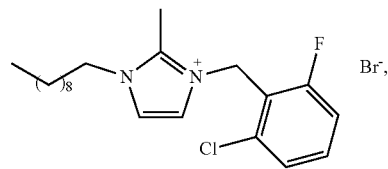
IA-29
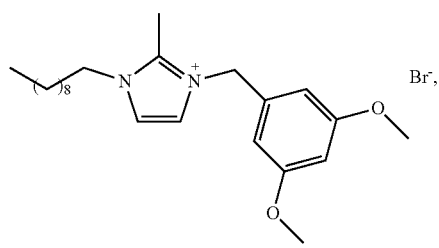
-continued
IA-30
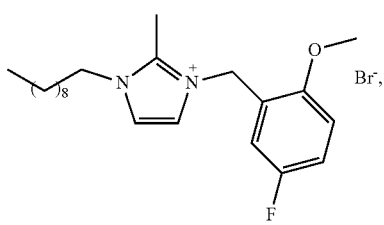
IA-31
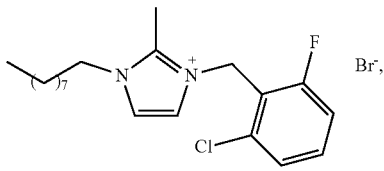
IA-32
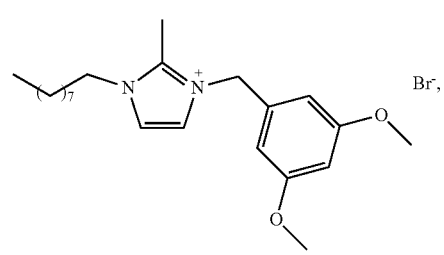
IA-33
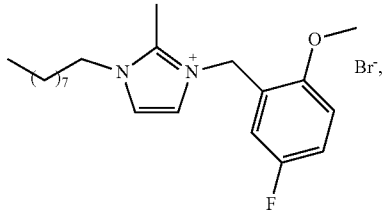
IA-34
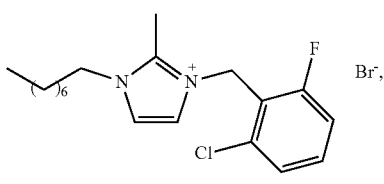
IA-35
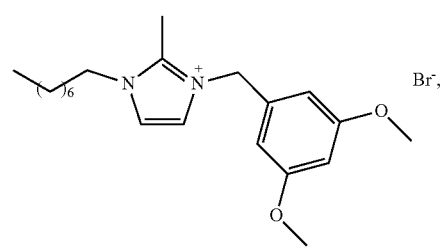
IA-36
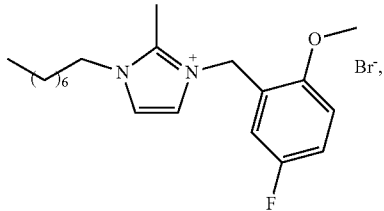

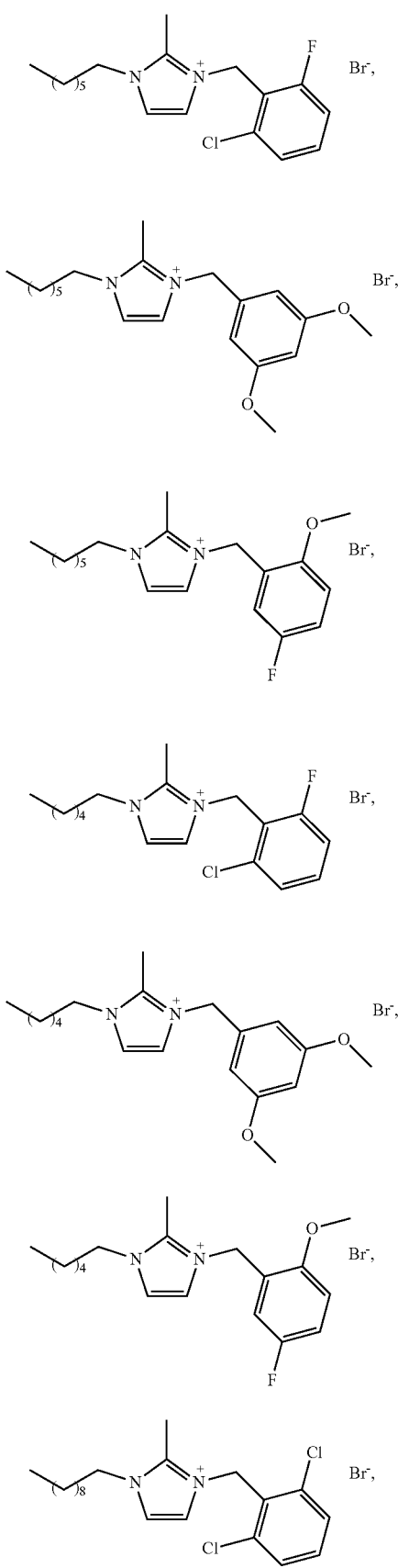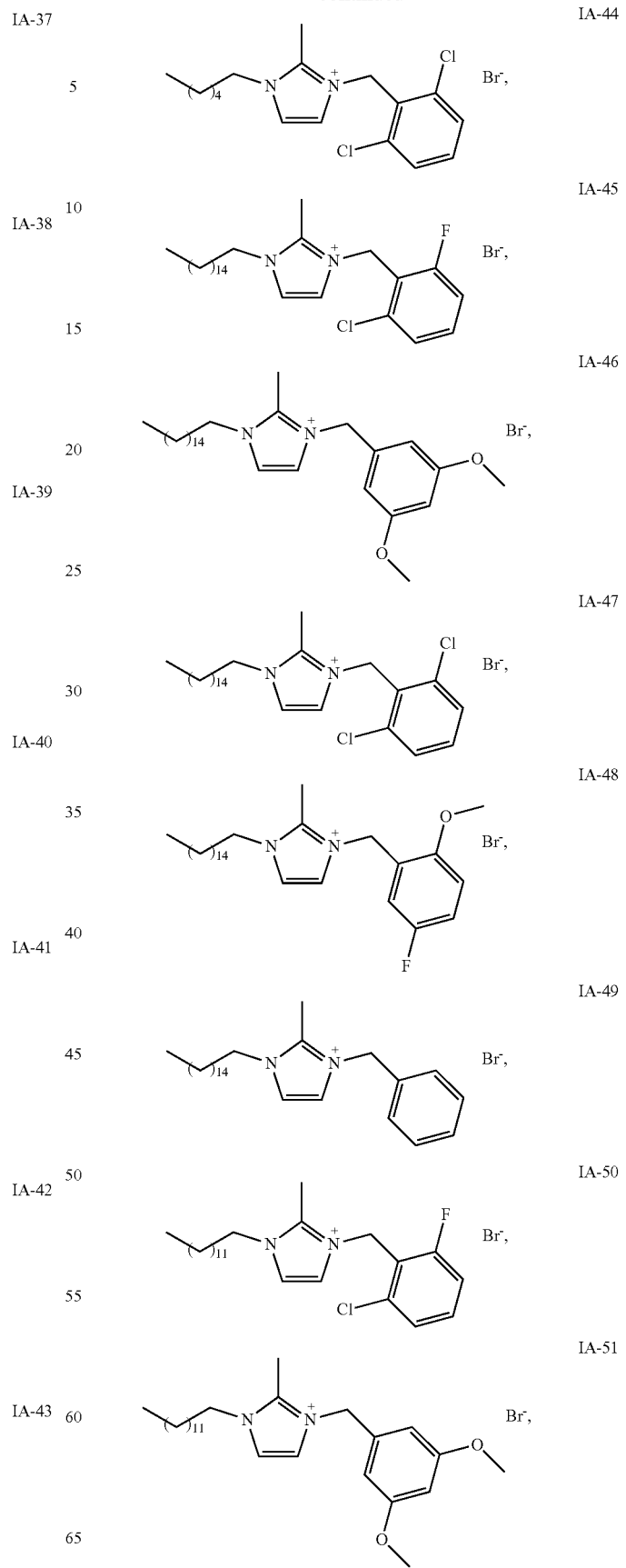

IA-52 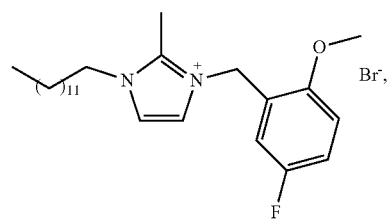
IA-53 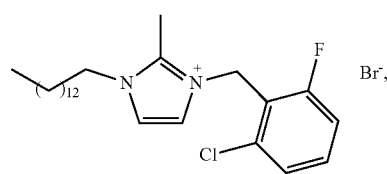
IA-54 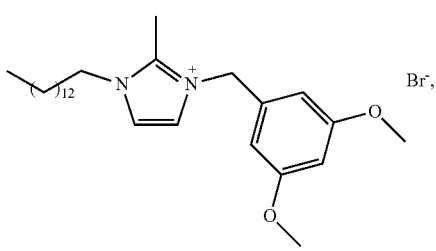
IA-55 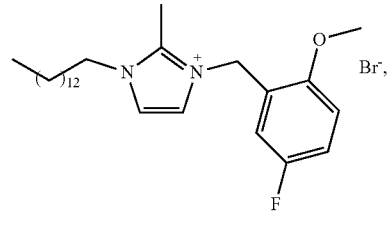
IA-56 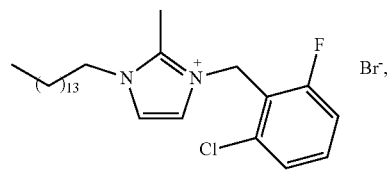
IA-57 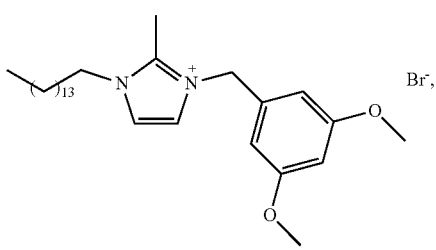
IA-58 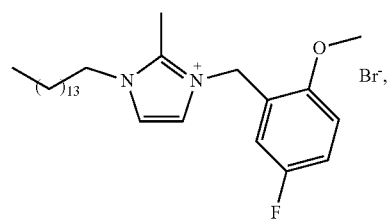
IA-59 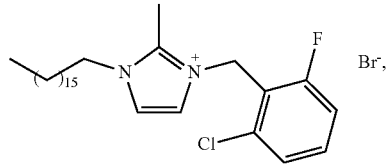
IA-60 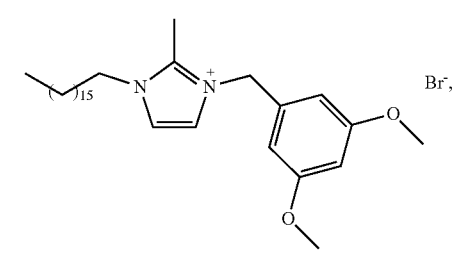
IA-61 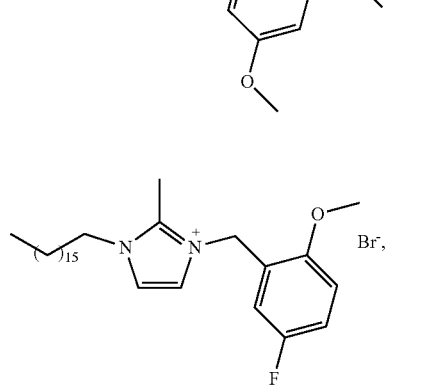
IA-62 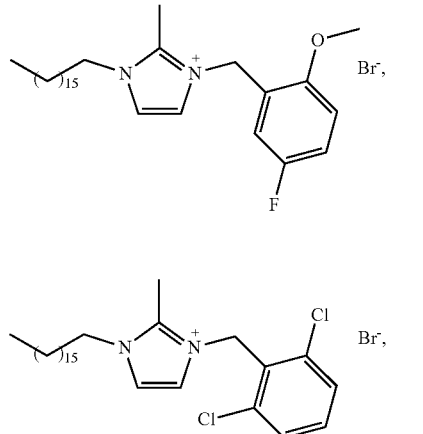
IA-63 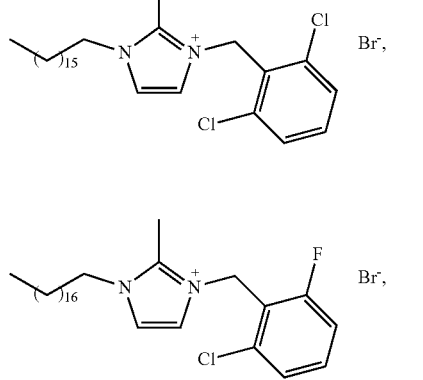
IA-64 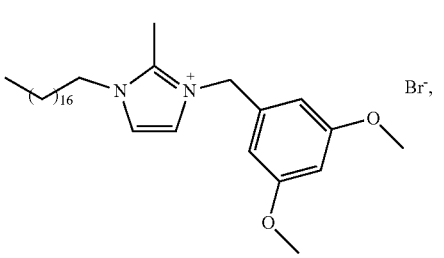
IA-65 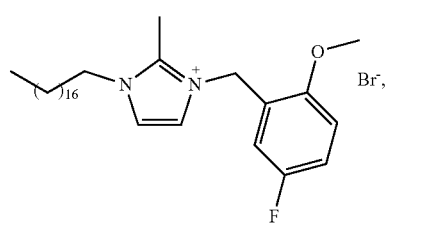

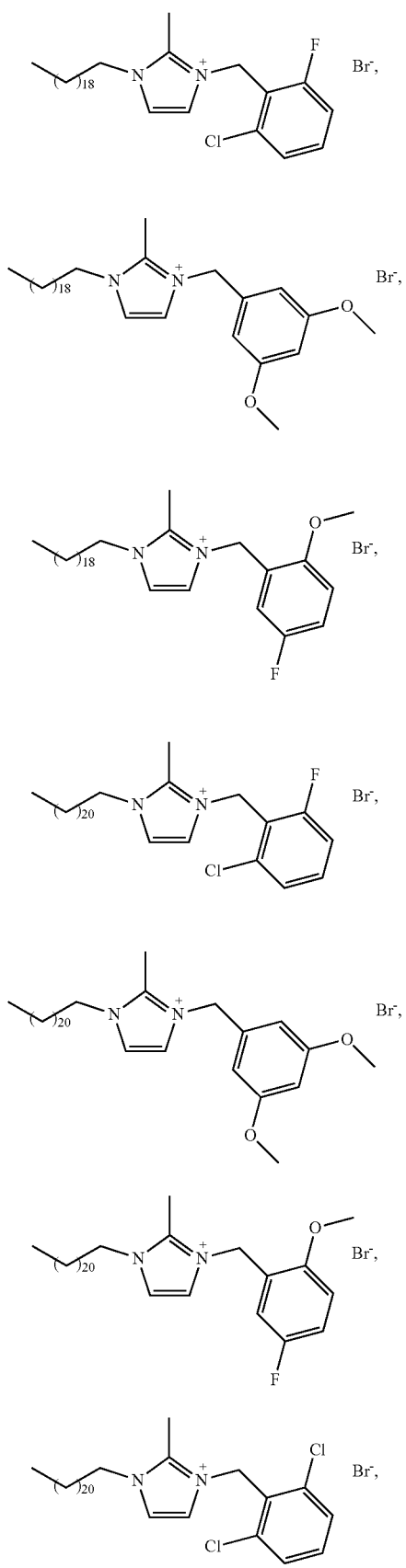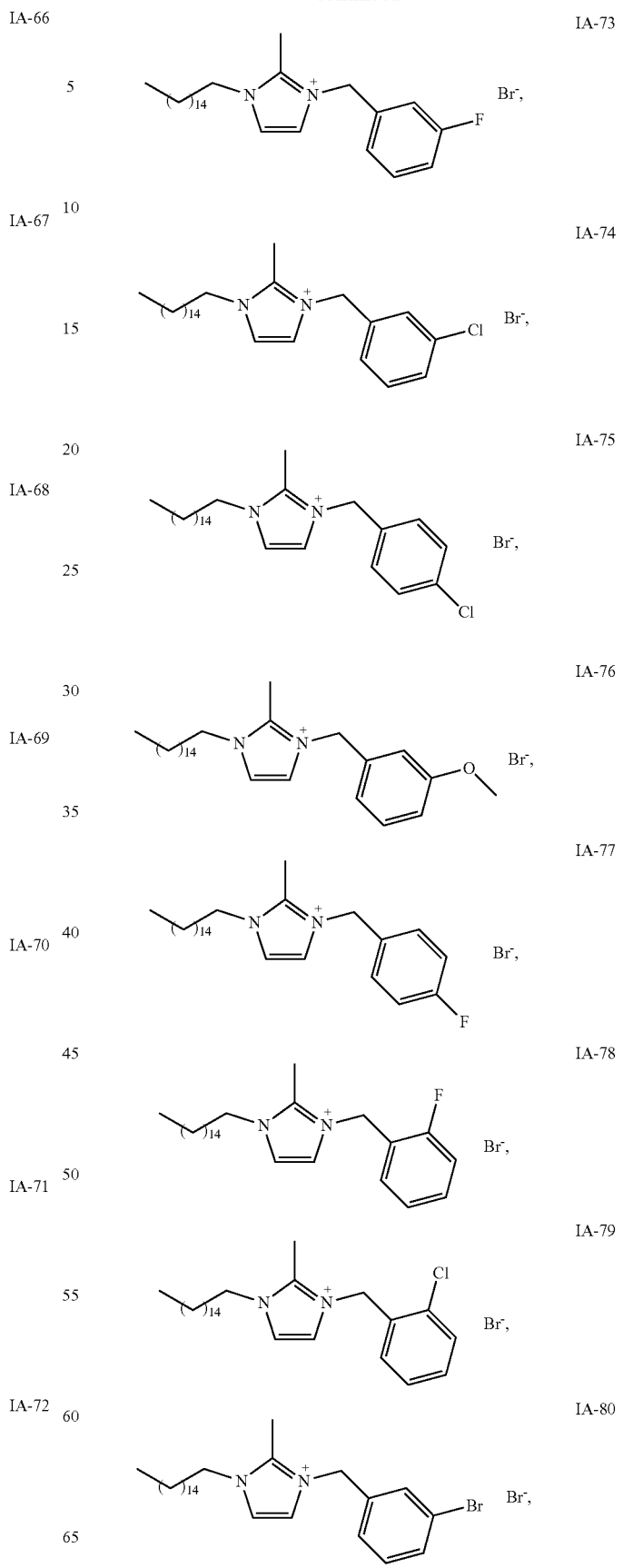

IA-81
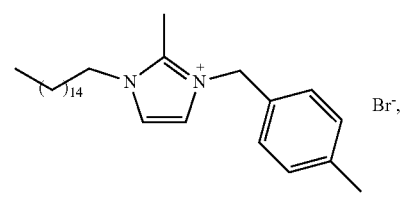
IA-82
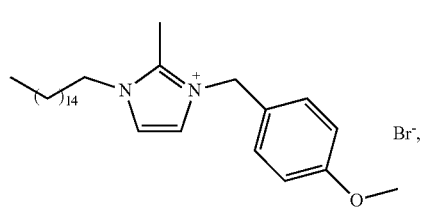
IA-83
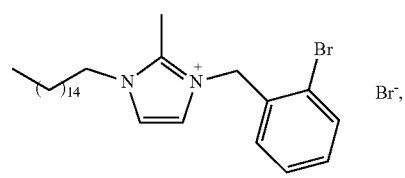
IA-84
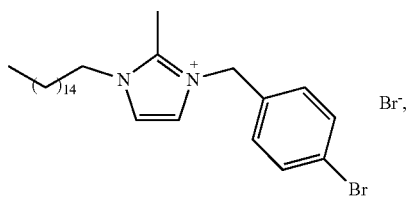
IA-85
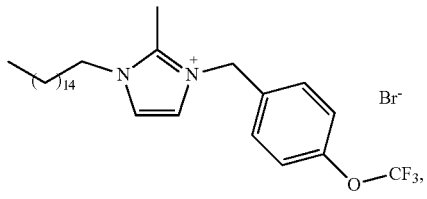
IA-86
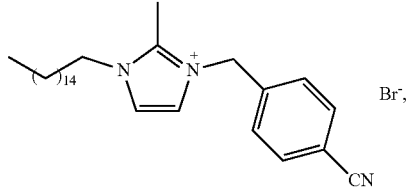
IA-87
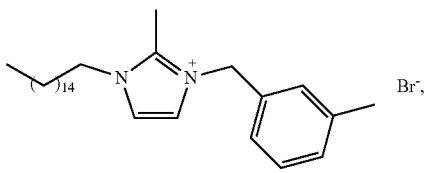
IA-88
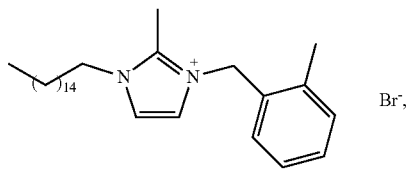
IA-89
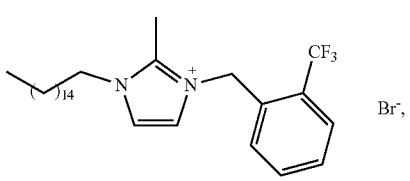
IA-90
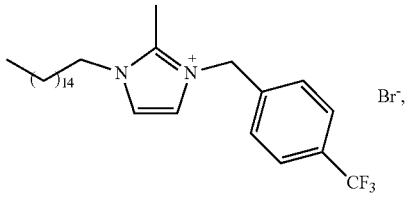
IA-91
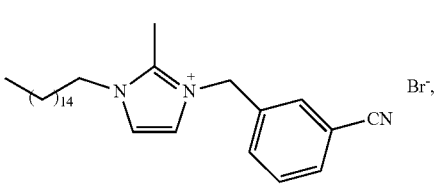
IA-92
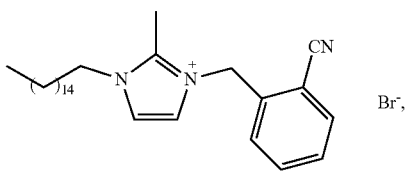
IA-93
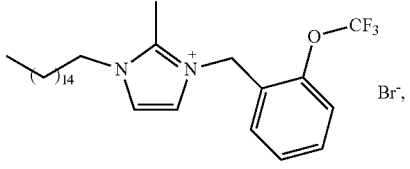
IA-94
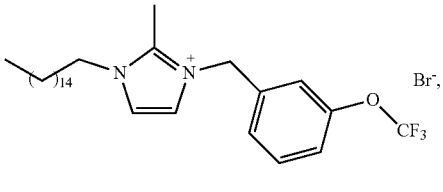
IA-95
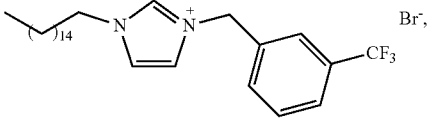
IA-96
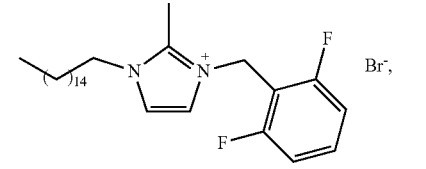

IA-97
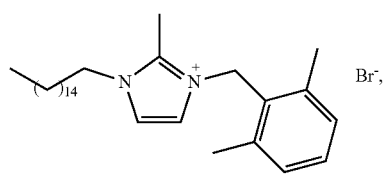
IA-98
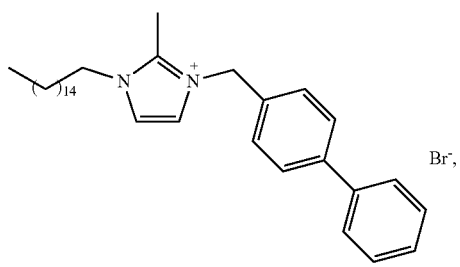
IA-99
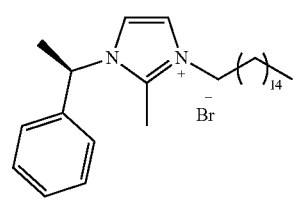
IA-100
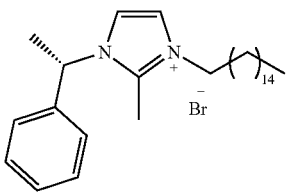
A-101
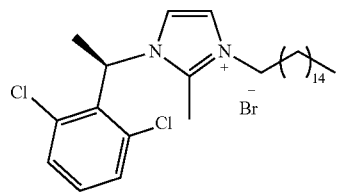
IA-102
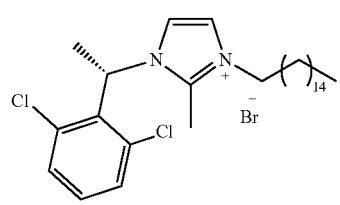
IB-1
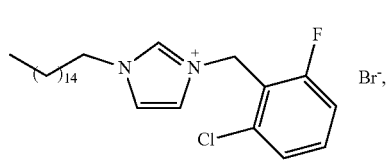
IB-2
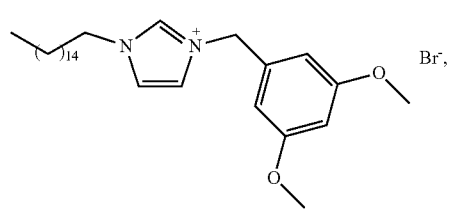
IB-3
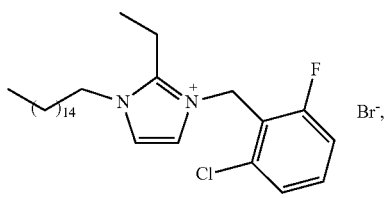
IC-1
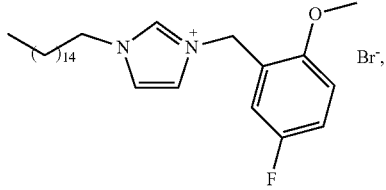
IC-2
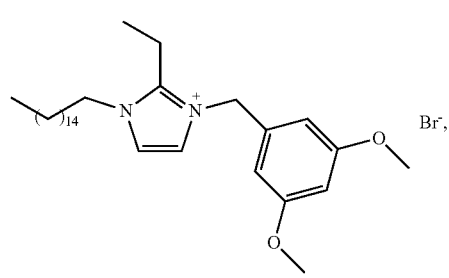
IC-3
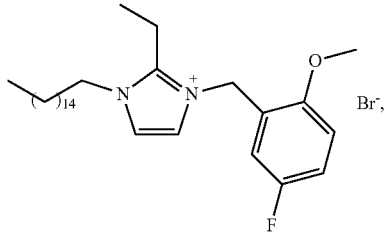
IC-4
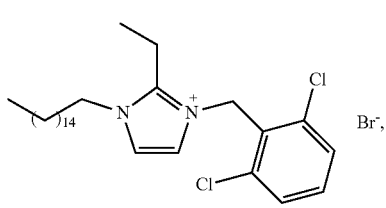
ID-1
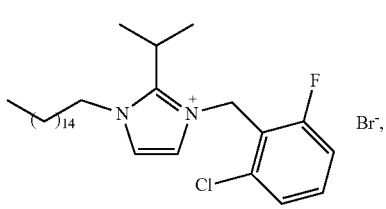

-continued

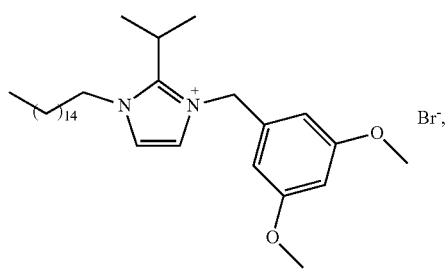
ID-2

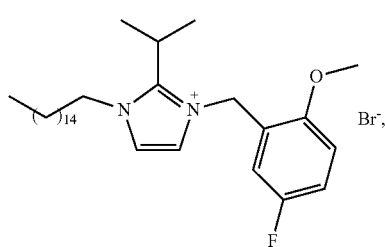
ID-3

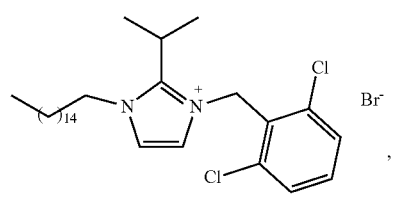
ID-4

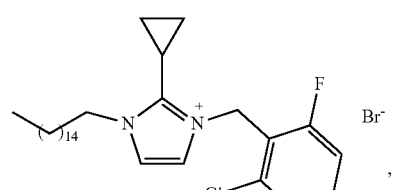
IE-1

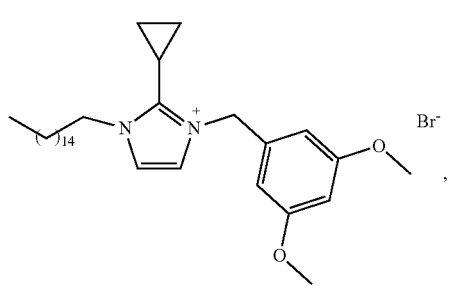
IE-2

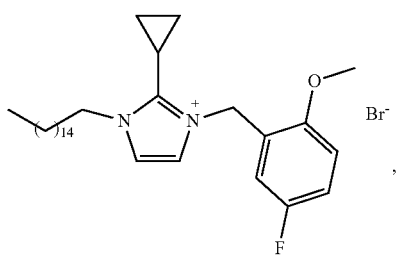
IE-3

-continued

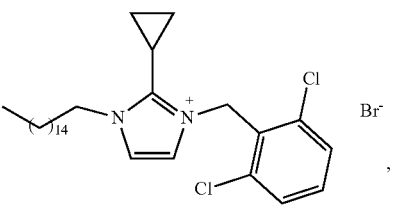
IE-4

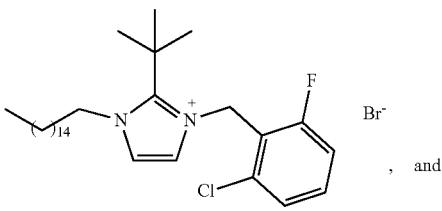
IF-1

, and

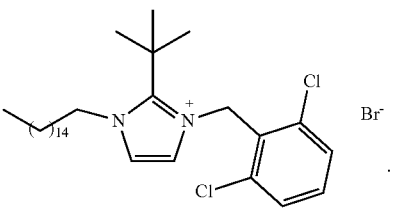
IF-2

.

6. A method for inhibiting triglyceride synthesis, for treating obesity and type II diabetes, for treating fatty liver, for treating tumor, for treating Parkinson's disease, for treating Alzheimer's disease or for prolonging the lifespan of mammals, comprising administrating the compound having the general formula

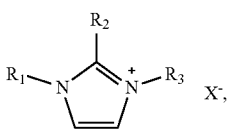

I or a stereoisomer thereof, a prodrug thereof, a pharmaceutically acceptable salt thereof or a pharmaceutically acceptable solvate thereof; or a pharmaceutical composition comprising the above compound to the subject in need thereof:
wherein
$R_1$ is C1-C22 alkyl;
$R_2$ is selected from the group consisting of H, methyl, ethyl, isopropyl, t-butyl, and cyclopropyl;
$R_3$ is selected from the group consisting of:
formula (a),

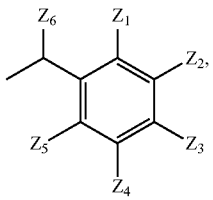

wherein any two of $Z_1$, $Z_2$, $Z_4$, $Z_5$ each are independently selected from the group consisting of:

(1) H, F, Cl, Br, I, nitro, and cyano; and
(2) C1-C3 alkyl, C1-C3 alkoxy, C1-C3 fluorine-containing alkyl, and C1-C3 fluorine-containing alkoxy;
the rest and $Z_3$ being H;
$Z_6$ is H or methyl; and
2) formula (b),

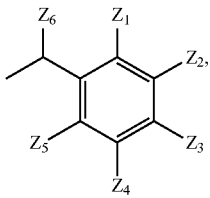

wherein for $Z_1$, $Z_2$, $Z_3$, $Z_4$, and $Z_5$:
one is independently selected from the consisting of:
(1) H, F, Cl, Br, I, nitro, and cyano; and
(2) C1-C3 alkyl, C1-C3 alkoxy, C1-C3 fluorine-containing alkyl, and C1-C3 fluorine-containing alkoxy;
the rest being H;
$Z_6$ is H or methyl;
$X^-$ is an anion of a pharmaceutically acceptable inorganic or organic acid salt.

7. The method according to claim 6, wherein $R_3$ is formula (a),

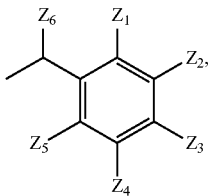

wherein for $Z_1$, $Z_2$, $Z_3$, $Z_4$, and $Z_5$:
$Z_1$, $Z_5$, or $Z_2$, $Z_4$, or $Z_1$, $Z_4$ each are independently selected from the group consisting of:
(1) H, F, Cl, Br, I, nitro, and cyano; and
(2) C1-C3 alkyl, C1-C3 alkoxy, C1-C3 fluorine-containing alkyl, and C1-C3 fluorine-containing alkoxy;
$Z_6$ is H or methyl.

8. The method according to claim 6, wherein the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, a-ketoglutarate, a-glycerophosphate, alkyl sulfonate or aryl sulfonate; or, said alkyl sulfonate is methyl sulfonate or ethyl sulfonate; said aryl sulfonate is benzenesulfonate or p-toluenesulfonate.

9. The method according to claim 6, wherein

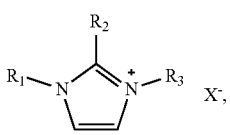

is selected from the group consisting of:

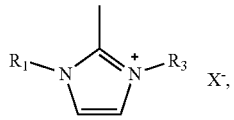  IA

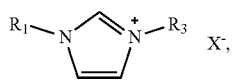  IB

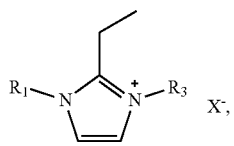  IC

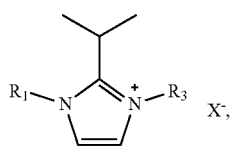  ID

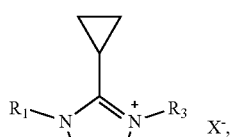  IE

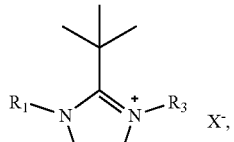  and  IF wherein $R_1$, $R_3$ and X are as defined in claim 6.

10. A method for inhibiting triglyceride synthesis, for treating obesity and type II diabetes, for treating fatty liver, for treating tumor, for treating Parkinson's disease, for treating Alzheimer's disease or for prolonging the lifespan of mammals, comprising administrating a compound or a stereoisomer thereof, a prodrug thereof, a pharmaceutically acceptable salt thereof or a pharmaceutically acceptable solvate thereof or a pharmaceutical composition comprising the above compound to the subject in need thereof: wherein the compound is selected from the group consisting of:

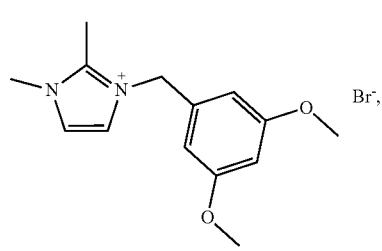  IA-1

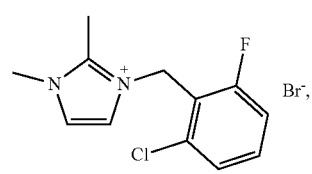  IA-2

-continued
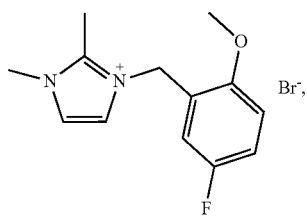
IA-3
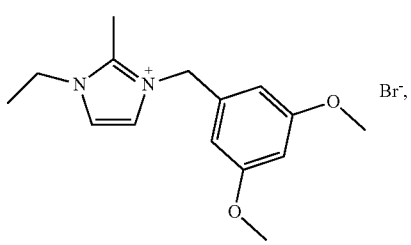
IA-4
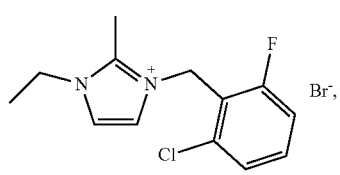
IA-5
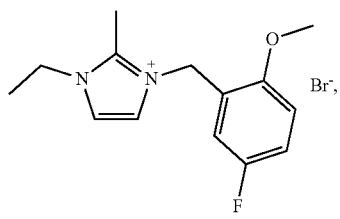
IA-6
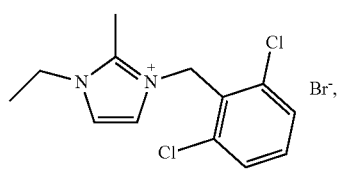
IA-7
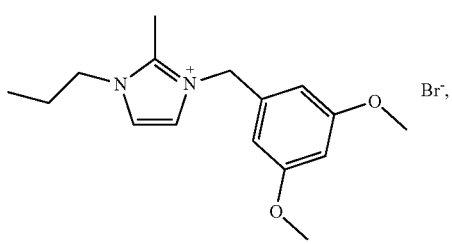
IA-8
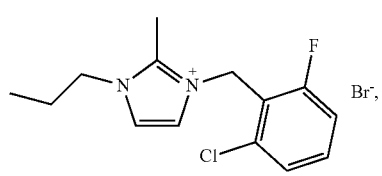
IA-9
-continued
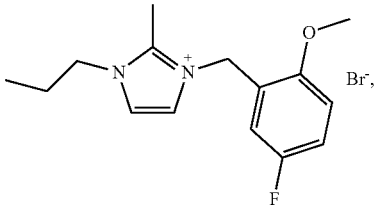
IA-10
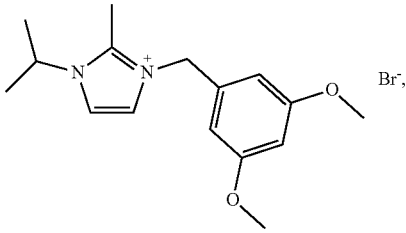
IA-11
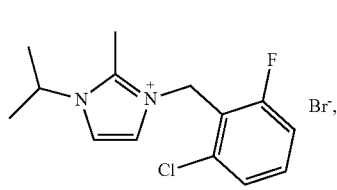
IA-12
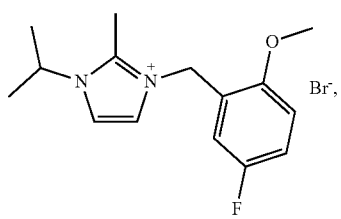
IA-13
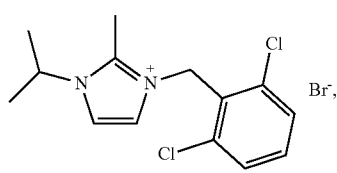
IA-14
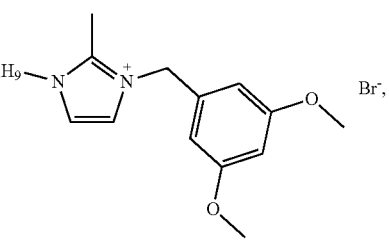
IA-15
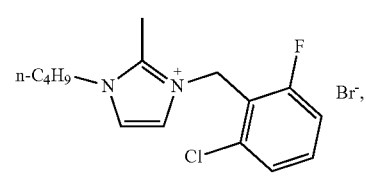
IA-16

IA-17
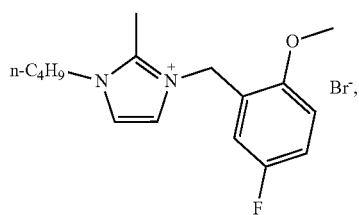
IA-18
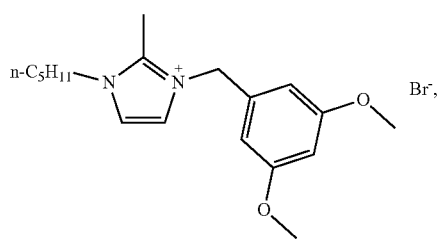
IA-19
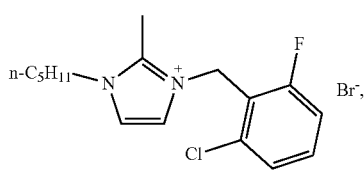
IA-20
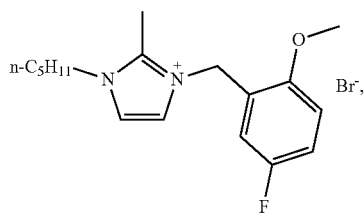
IA-21
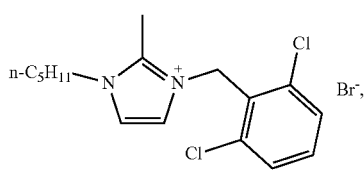
IA-22
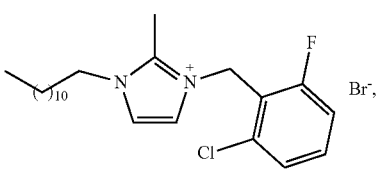
IA-23
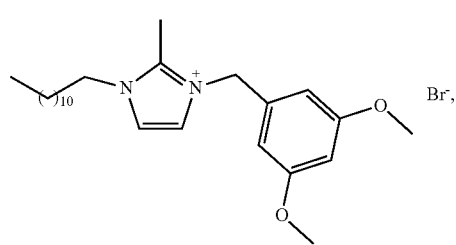
IA-24
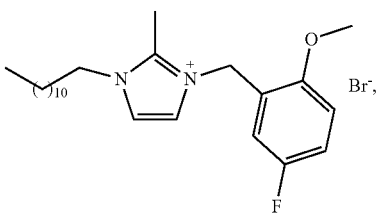
IA-25
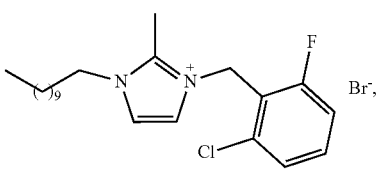
IA-26
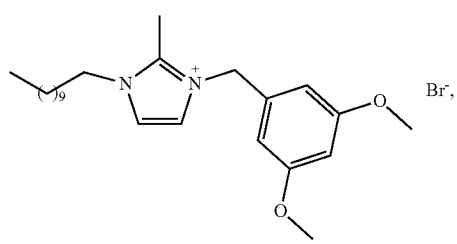
IA-27
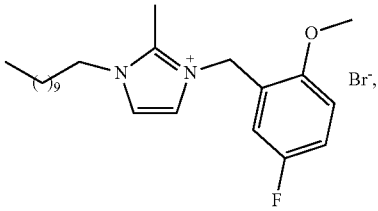
IA-28
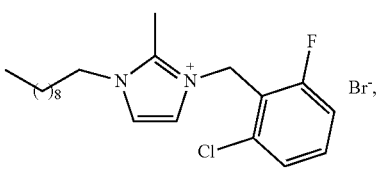
IA-29
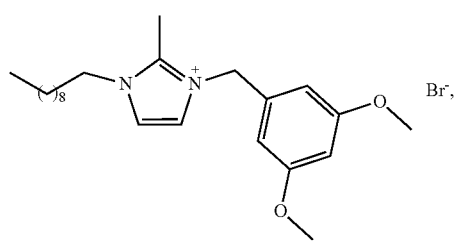
IA-30
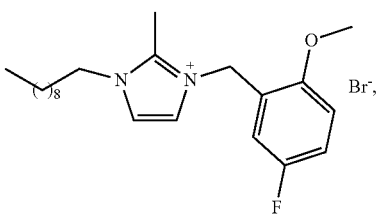

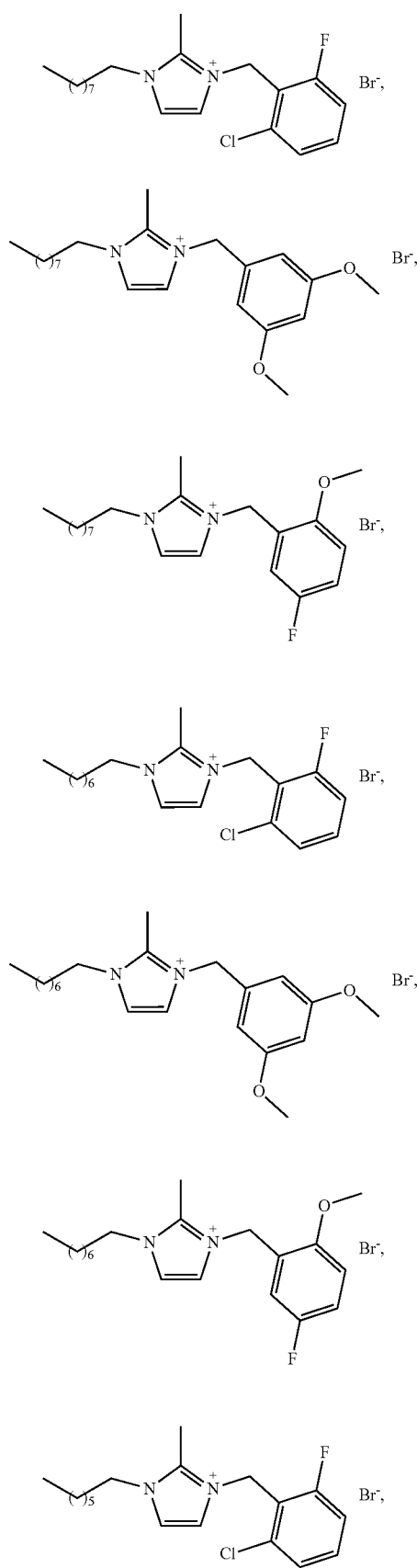

IA-46
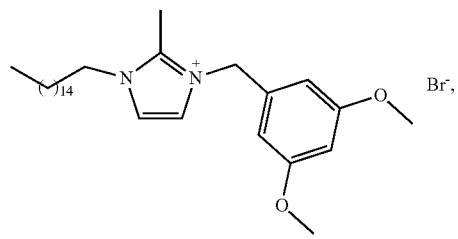
IA-47
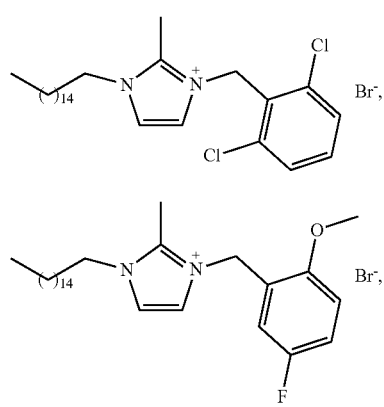
IA-48
IA-49
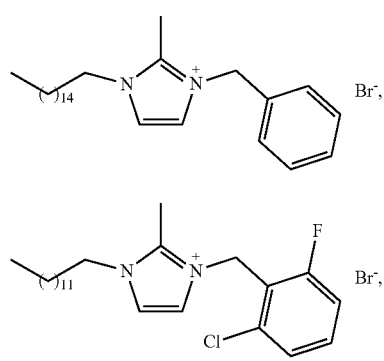
IA-50
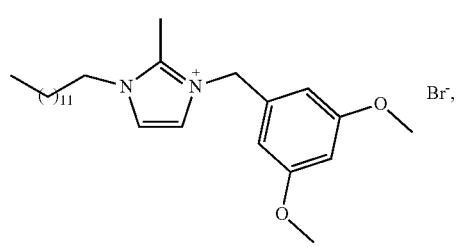
IA-51
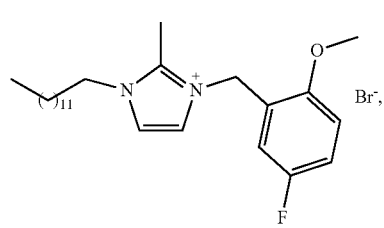
IA-52
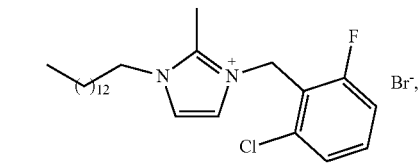
IA-53
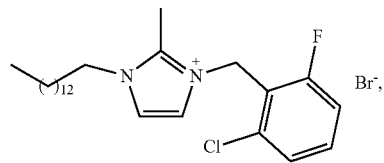
IA-54
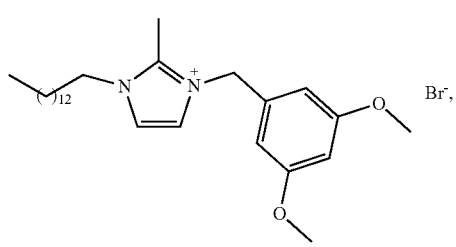
IA-55
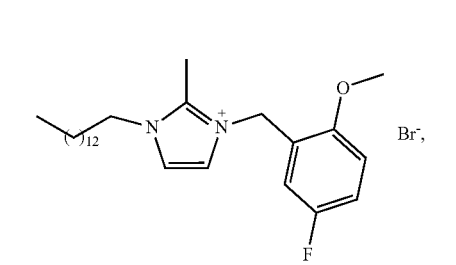
IA-56
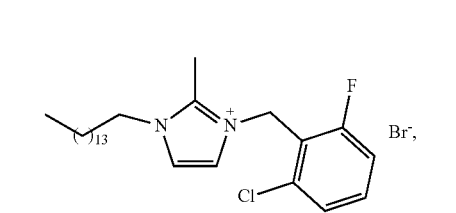
IA-57
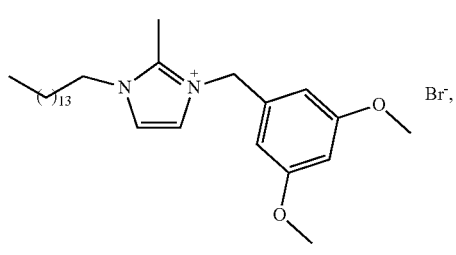
IA-58
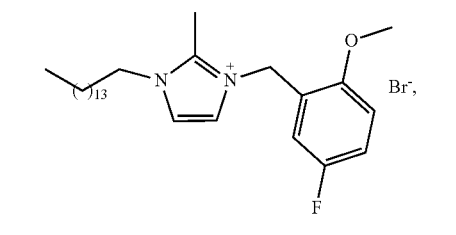
IA-59
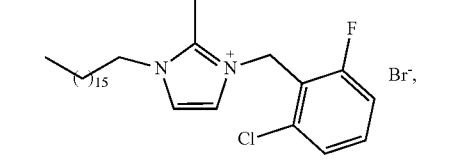
IA-60
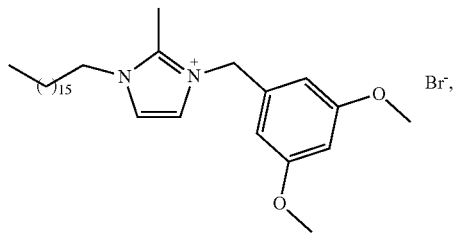

-continued
IA-61
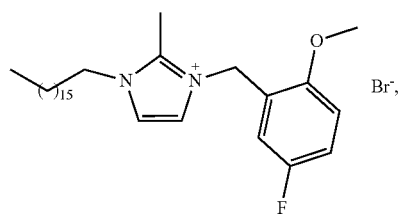
IA-62
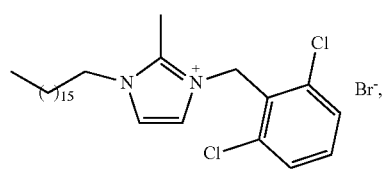
IA-63
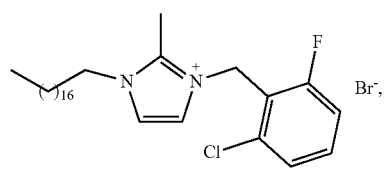
IA-64
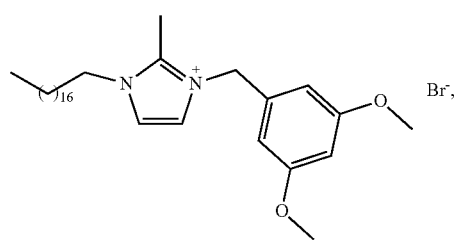
IA-65
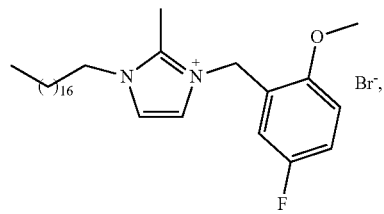
IA-66
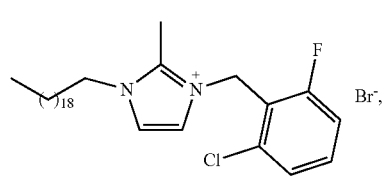
IA-67
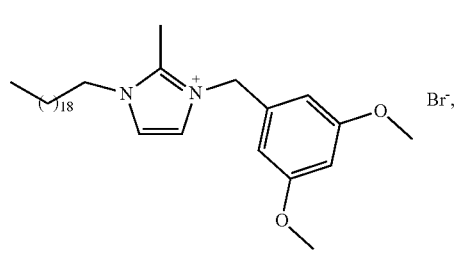
-continued
IA-68
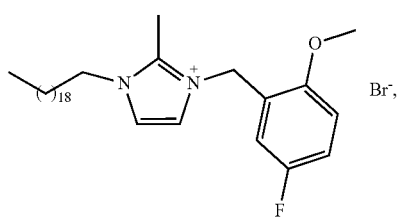
IA-69
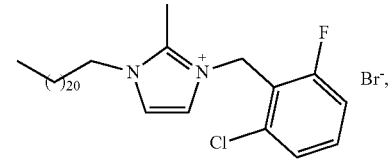
IA-70
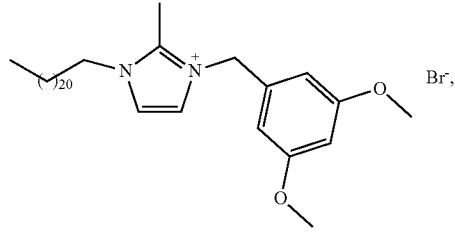
IA-71
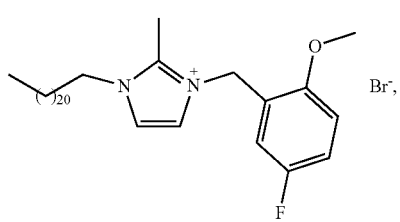
IA-72
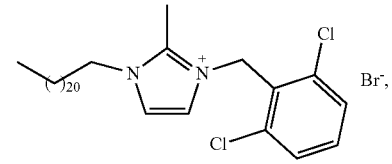
IA-73
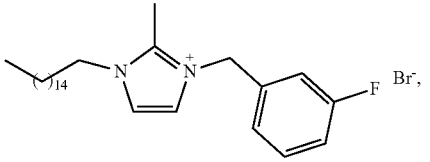
IA-74
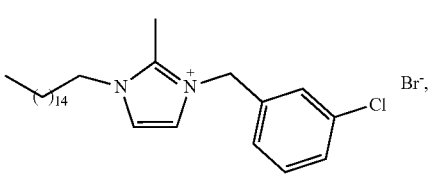
IA-75
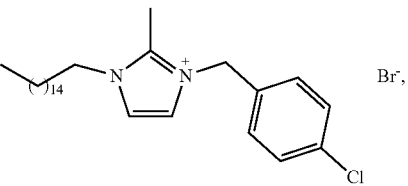

-continued
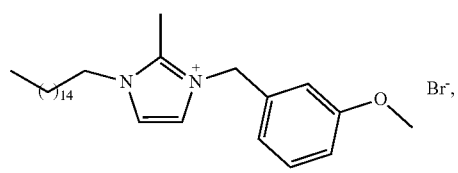 IA-76
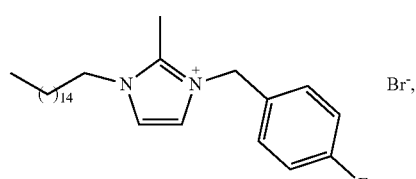 IA-77
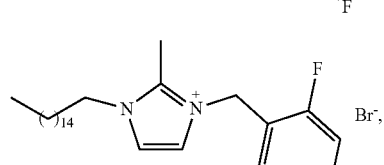 IA-78
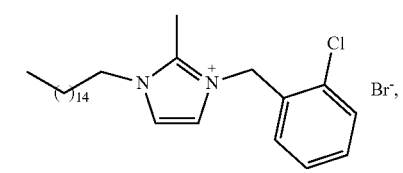 IA-79
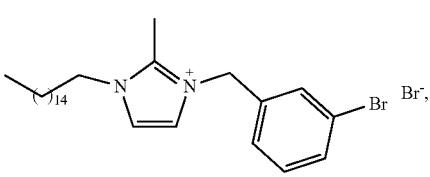 IA-80
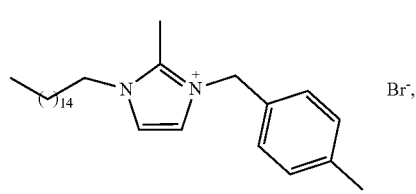 IA-81
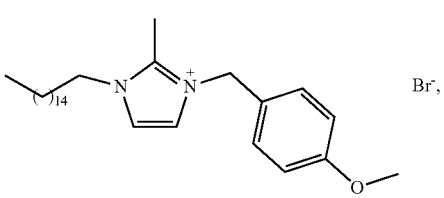 IA-82
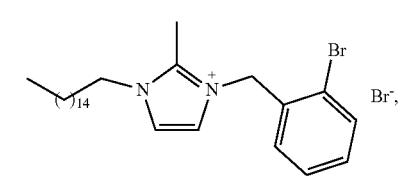 IA-83
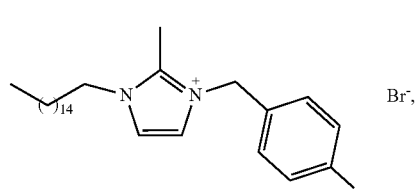 IA-84
-continued
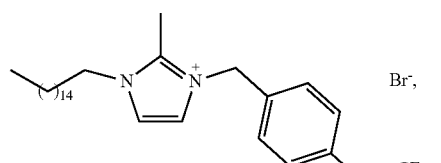 IA-85
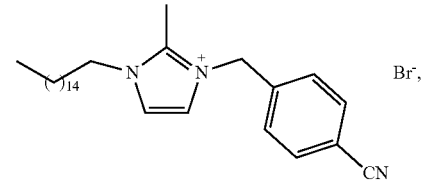 IA-86
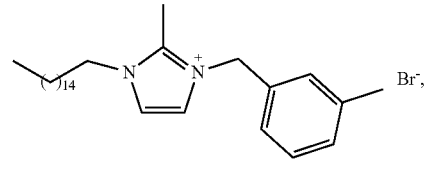 IA-87
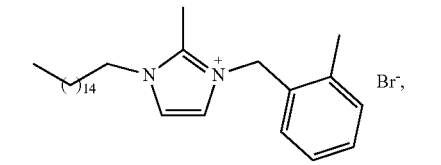 IA-88
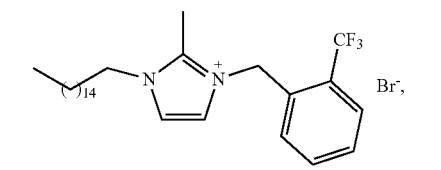 IA-89
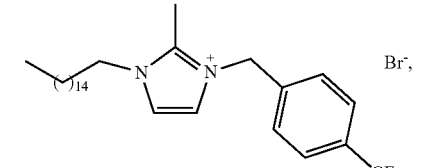 IA-90
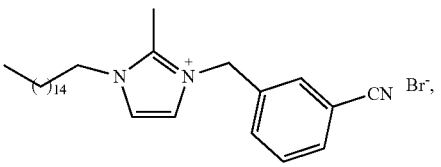 IA-91
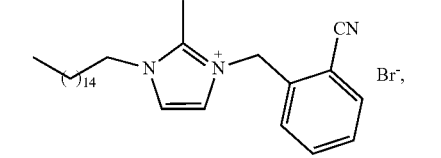 IA-92
IA-93